United States Patent [19]
Lowenthal et al.

[11] Patent Number: 6,083,724
[45] Date of Patent: Jul. 4, 2000

[54] RECOMBINANT AVIAN INTERFERON-GAMMA (IFN-γ)

[75] Inventors: John William Lowenthal, Croydon North; Jennifer Joy York, Clifton Hill; Terri Ellen O'Neil, Flemington; Stephen Rhodes, Blackburn; Matthew Robert Digby, Wurzberg, all of Australia

[73] Assignee: Commonwealth Scientific and Industrial Research Organization, Australian Capital Territory, Australia

[21] Appl. No.: 08/765,381

[22] PCT Filed: Mar. 5, 1996

[86] PCT No.: PCT/AU96/00114

§ 371 Date: Apr. 25, 1997

§ 102(e) Date: Apr. 25, 1997

[87] PCT Pub. No.: WO96/27666

PCT Pub. Date: Sep. 12, 1996

[30] Foreign Application Priority Data

Mar. 6, 1995 [AU] Australia ............... PN1542/95

[51] Int. Cl.[7] ............... C12N 15/23; C07K 14/57; A61K 38/21
[52] U.S. Cl. ............... 435/69.51; 435/203.1; 435/365; 435/252.3; 435/252.33; 435/254.11; 536/23.52; 530/351; 424/85.5; 424/198.1; 424/185.1; 424/442
[58] Field of Search ............... 435/320.1, 69.51, 435/325, 252.3, 252.33, 254.11, 6, 365; 536/23.52; 424/85.5, 442, 185.1, 198.1; 530/351

[56] References Cited

U.S. PATENT DOCUMENTS

| | | | |
|---|---|---|---|
| 4,456,748 | 6/1984 | Goeddel | 536/23.4 |
| 4,935,233 | 6/1990 | Bell et al. | |
| 5,641,656 | 6/1997 | Sekellick et al. | 435/69.51 |

FOREIGN PATENT DOCUMENTS 0 088 540  9/1983  European Pat. Off. .
4036855  5/1992  Germany .

OTHER PUBLICATIONS

Schultz, et al., *Eur. J. of Immunology*, vol. 25, pp. 847–851 (1995) "Recombinant chicken interferon: a potent antiviral agent that lacks intrinsic macrophage activating factor activity".

Schultz, et al. *Eur. J. of Biochemistry*, vol. 229, pp. 73–76 (1995) "Recombinant chicken interferon from *Escherichia coli* and transfected COS cells is biologically active".

Weiler, H., et al. (1987) *Avian Pathol.* 16 : 439–52.

Frederickson, T. L., et al. (1987) *Prog. Clin. Biol. Res.* 23:145–56.

Digby, M. R., et al. (1995) *J. IFN Cytobine Res.* 15 : 939–45.

Gray, et al., (1982) "Expression of human immune interferon cDNA in E. coli and monkey cells," *Nature*, 295:503–508.

Lillehoj, et al., (1993) "Avian Interleukin–2 and Interferon," *Colloques De L'Inra (Avian Immunology In Progress)*, 62:105–111.

Lillehoj, et al., (1993) "Biochemical and functional characterizations of avian gamma–Interferon and Interleukin–2," *Colloques De L'Inra (Avian Immunology In Progress)*, 62:131–136.

Lowenthal, et al., (1995) "Production of Interferon–gamma by chicken T cells," *Journal of Interferon and Cytokine Research*, 15:933–938.

Sekkellick, et al., (1994) "Chicken Interferon gene: Cloning, expression and analysis," *Journal of Interferon Research*, 14:71–79.

Weinig, et al, (1996) "Biological properties of recombinant chicken Interferon–gamma," *European Journal of Immunology*, 26:2440–2447.

*Primary Examiner*—David L. Fitzgerald
*Attorney, Agent, or Firm*—Scully, Scott, Murphy & Presser

[57] ABSTRACT

A cDNA corresponding to the chicken interferon-γ (IFN-γ) gene has been isolated. The invention thus provides avian IFN-γ polypeptides, nucleic acids encoding them, and their recombinant production. The nucleic acids and polypeptides are useful as therapeutic agents and as adjuvants for the treatment of birds.

27 Claims, 51 Drawing Sheets

5' -- -97 AGAAGACATAACTATTA
GAAGCTGAAGCTCACTGAGCTTATATCTGACATCTCCCAGAAGCTATCTGAGCATTGAACTGAGCCATCACCAAGAAG

```
    Met Thr Cys Gln Thr Tyr Asn Leu Phe Val Leu Ser Val Ile Met Ile Tyr Tyr Gly
    ATG ACT TGC CAG ACT TAC AAC TTG TTT GTT CTG TCT GTC ATC ATG ATT TAT GGA
1                                       10                                  20
His Thr Ala Ser Ser Leu Asn Leu Val Gln Leu Gln Asp Asp Lys Asp Lys Leu Lys Ala
CAT ACT GCA AGT AGT CTA AAT CTT GTT CAA CTT CAA GAT GAT AAA GAC AAA CTG AAA GCT
21                                      30                                  40
Asp Phe Asn Ser Ser His Ser Asp Val Ala Asp Gly Gly Pro Ile Ile Val Glu Lys Leu
GAC TTT AAC TCA AGT CAT TCA GAT GTA GCT GAC GGT GGA CCT ATT ATT GTA GAG AAA CTG
41                                      50                                  60
Lys Asn Trp Thr Glu Arg Asn Glu Lys Arg Ile Ile Leu Ser Gln Ile Val Ser Met Tyr
AAG AAC TGG ACA GAG AGA AAT GAG AAA AGG ATC ATA CTG AGC CAG ATT GTT TCG ATG TAC
61                                      70                                  80
Leu Glu Met Leu Glu Asn Thr Asp Lys Ser Lys Pro His Ile Lys His Ile Ser Glu Glu
TTG GAA ATG CTT GAA AAC ACT GAC AAG TCA AAG CCG CAC ATC AAA CAC ATA TCT GAG GAG
81                                      90                                  100
Leu Tyr Thr Leu Lys Asn Asn Leu Pro Asp Gly Val Lys Lys Val Lys Asp Ile Met Asp
CTC TAT ACT CTG AAA AAC AAC CTT CCT GAT GGC GTG AAG AAG GTG AAA GAT ATC ATG GAC
```

Figure 12a

```
101
    Leu Ala Lys Leu Pro Met Asn Asp Leu Arg Ile Gln Arg Lys Ala Ala Asn Glu Leu Phe
    CTG GCC AAG CTC CCG ATG AAC GAC TTG AGA ATC CAG CGC AAA GCC GCG AAT GAA CTC TTC
                                    110                                  120
121
    Ser Ile Leu Gln Lys Leu Val Asp Pro Ser Phe Lys Arg Lys Ser Gln Ser Gln
    AGC ATC TTA CAG AAG CTG GTG GAT CCT TCC AGT TTC AAA AGG AAA AGG AGC CAG TCT CAG
                                    130                                  140
141                 145
    Arg Arg Cys Cys Asn Cys  ***
    AGG AGA TGC TGC AAT TGC  492  TAATGGCATCTTATGACCTCCCTGTGCTCAACTATTTAAATTTTACAATGCACAA

TTTTTATGTTGTGATTTTTAACTGAGTTTATATACATTTATTTATTAAGTATTTAAATAATTATTTATAT
TAAAAAAAAACCAGGCAAACAATGAAAGTATTTATACCTCCTACTGCTGTGTAAGAAACGGATTGTGTCTTAAATAC
TGTCTATCTGTGTGTGGGTTGACTGGTTGACTGAATGGATGTTTACCAGTTTCTGTGTGGGAAATACTGA
ATTGGAGGTGGATCTGTACTCAAGAAACCCACTCATCCGGTCAGTCTAGTATTCTAAATCCAAATCAAGGAGTGGC
TTGTTTAAAGGGAAAAAAATGTGAGCACTCTCTGACTGGGTCTTAGAGATTTTACTGATGGTTTGGCATGACTAAGAATT
TAGG    943     ---3'
```

Figure 12b

```
avian              MTCQTYNL-FVLSVIMIYYGHTASSLNLVQLQDDIDKLKADFNSSHSDVADGGPIIVEKL
bovine             MKYTSYFLALLLCGLLGFSG----SYGQGQFFREIENLKEYFNASSPDVAKGGPLFSEIL
nonhuman primate   MKYTSYILAFQLCVVLGSLG----CYCQDPYVKEAENLKKYFNAGDSDVADNGTLFLDIL
nonhuman primate   MKYTSYILALQLCVLLGFSG----SYGQGPFFKEIENLKEYFNASNPDVAEGGPLFIEIL
canine             -------SL------G------CYCQAMFFKEIENLKEYFNASNPDVSDGGSLFVDIL
human              MKYTSYILAFQLCIVLGSLG----CYCQDPYVKEAENLKKYFNAGHSDVADNGTLFLGIL
murine             MNATHCILALQLF-LMAVSG----CYCHGTVIESLESLNNYFNSSGID-VEEKSLFLDIW
porcine            MSYTTYFLAFQLCVTLCFSG----SYCQAPFFKEITILKDYFNASTSDVPNGGPLFLEIL
rat                MSATRRVLVLQLC-LMALSG----CYCQGTLIESLESLKNYFNSSSMDAMEGKSLLLDIW
ovine              MKYTSSFLALLLCVLLGFSG----SYGQGPFFKEIENLKEYFNASNPDVAKGGPLFSEIL
equine             MNYTSFILAFQLCAIL---GS-STYYCQAAFFKEIENLKEYFNASNPDVGDGGPLFLDIL
                            *              *            *. **..*         .

avian              KNWTERNEKRIILSQIVSMYLEMLE---NTDKSKPHIKHISEELYTLKNNLPDGVKKVKD
bovine             KNWKDESDKKIIQSQIVSFYFKLFENLKDNQVIQRSMDIIKQDMFQ--KFLNGSSEKLED
nonhuman primate   RTWREEGDRKIMQSQIISFYFKLFKNFKDNQSIQKSMETIKEDMNV--KFFNSNKRKQDD
nonhuman primate   KNWKEESDRKIIQSQIVSFYFKLFENFKDNQVIQRSVDIIKQDMFQ--KFLNGSSEKLED
canine             KKWREESDKTIIQSQIVSFYFKLFDNFKDNQIIQRMSDTIKEDMLG--KFLNSSTSKRED
human              KNWKEESDRKIMQSQIVSFYFKLFKNFKDDQSIQKSVETIKEDMNV--KFFNSNKKKRDD
murine             RNWQKDGDMKILQSQIISFYLRLFEVLRLFKFFEIFKDNQAISNNISVIESHLIT--TFFSNSKAKKDA
porcine            KNWKEESDKKIIQSQIVSFYFKFFEIFKDNQAIQRSMDVIKQDMFQ--RFLNGSSGKLND
rat                RNWQKDGNTKILESQIISFYFKLFKLFENLKDNQAISNNISVIESHLIT--NFFSNSKAKKDA
ovine              KNWKEESDKKIIQSQIVSFYFKLFENLKDNQVIQRSMDIIKQDMFQ--KFLNGSSEKLED
equine             KNWKEDSDKKIIQSQIVSFYFKLFENLKDNQVIQKSMDTIKEDLFV--KFFNSSTSKLED
                     *            *. ****.**          *         *
```

Figure 13a

```
avian              IMDLAKLPMNDLRIQRKAANELFSILQKLVDPPSF-KRKRSQSQ--RRCNC
bovine             FKKLIQIPVDDLQIQRKAINELIKVMNDLSPKSNLRKRKRSQNLFRGRRAST
nonhuman primate   FERLTNYSVNDLNVQRKAIHELIQVMAELSPAPKIGKRRRSQTLFRGRRASQ
nonhuman primate   FKKLIQISVDDMQIQRKAINELIKVMNDLSPKSNLIKRKRSQNLFRGRRASM
canine             FLKLIQIPVNDLQVQRKAINELIKVMNDLSPRSNLRKRKRSQNLFRGRRASK
human              FEKLTNYSVTDLNVQRKAIHELIQVMAELSPAAKTGKRKRSQMLFQGRRASQ
murine             FMSIAKFEVNNPQVQRQAFNELIRVVHQLLPESSLRKRKRSRC--------
porcine            FEKLIKIPVDNLQIQRKAISELIKVMNDLSPRSNLRKRKRSQNLFRGRRASK
rat                FMSIAKFEVNNPQIQHKAVNELIRVIHQLSPESSLRKRKRSRC--------
ovine              FKRLIQIPVDDLQIQRKAINELIKVMNDLSPKSNLRKRKRSQNLFRGRRASM
equine             FQKLIQIPVNDLKVQRKAISELIKVMNDLSPKANLRKRKRSQNPFRGRRALQ
                   .   . .      *.*   . ** .. .* *            ** .*.
```

Figure 13b

```
Human  MKYTSYILAFQLCIVLGSLG---CYCQDPYVKEAENLKKYFNAGHSDVADNGTLFLGIL
Avian  MTCQTYNL-FVLSVIMIYYGHTASSLNLVQLQDDIDKLKADFNSSHSDVADGGPIIVEKL
         *  *   *        *      **  ** *  ******  *

Human  KNWKEESDRKIMQSQIVSFYFKLFKNFKDDQSIQKSVETIKEDMNV--KFFNSNKKKRDD
Avian  KNWTERNEKRIILSQIVSMYLEMLEN---TDKSKPHIKHISEELYTLKNNLPDGVKKVKD
       ***  * ***  ****** *                *            *    ** *

Human  FEKLTNYSVTDLNVQRKAIHELIQVMAELSPAAKTGKRKRSQMLFRGRRASQ
Avian  IMDLAKLPMNDLRIQRKAANELFSILQKLVDPPSF-KRKRSQSQ---RRCNC
         **    *** ***** ***  *                ******   **
```

Figure 14

```
GAMMA     MTCQT-------YNLFVLSVIMIYYGHTAS------------SLNLVQLQDDIDKLKADF
TYPE 1    MAVPASPQHPRGYGILLLTLLLKALATTASACNHLRPQDATFSHDSLQLLRDMAPTLPQL
          *.  .       * ...*....   . ***            * . .**  *.    ...

GAMMA     NSSHSDVADGGPIIVEKLKNWTERNEKRIILSQIVSMYLEMLENTDKSKPHIKHISEELY
TYPE 1    CPQHNASCSFNDTILDTSNTRQADKTTHDILQHLFKILSSPSTPAHWNDSQRQSLLNRIH
           . *.        *..  . .   .  . ** ..  .       .. . .. . . . .

GAMMA     TLKNNLPDGVKKVKDIMDLAKLPMN-DLRIQRKAANELFSILQKLVDPPSFK---RKRSQ
TYPE 1    RYTQHLEQCLDS-SDTRSRTRWPRNLHLTIKKH-----FSCLHTFLQDNDYSACAWEHVR
             ..* . .    *    .. * * .* *..      ** *. ...   .    . . .

GAMMA     SQRRC------------NC
TYPE 1    LQARAWFLHIHNLTGNTRT
           * *
```

RECOMBINANT AVIAN INTERFERON-GAMMA (IFN-γ)

The present invention relates generally to recombinant polypeptides having avian cytokine properties or avian cytokine-like properties and to genetic sequences encoding same. More particularly, the present invention is directed to recombinant avian Type II interferon polypeptides and specifically to avian interferon-γ (IFN-γ) and derivatives, homologues and analogues thereof and uses of same as an immune response modulator and as a growth enhancing agent.

Bibliographic details of the publications referred to in this specification by author are collected at the end of the description. Sequence Identity Numbers (SEQ ID NOs.) for the nucleotide and amino acid sequences referred to in the specification are defined following the bibliography.

Throughout this specification and the claims that follow, unless the context requires otherwise, the word "comprise", or variations such as "comprises" or "comprising" will be understood to imply the inclusion of a stated element or integer or group of elements or integers, but not the exclusion of any other element or integer or group of elements or integers.

The rapidly increasing sophistication of recombinant DNA technology is greatly facilitating research into the medical and veterinary fields. Cytokine research is of particular importance, especially as these molecules regulate the proliferation, differentiation and function of a great variety of cells, such as cells involved in mediating an immune response. Administration of recombinant cytokines or regulating cytokine function and/or synthesis is becoming, increasingly, the focus of medical research into the treatment of a range of disease conditions in humans and animals.

In mammals, interferons (IFN) represent a family of cytokines that share the capacity to inhibit viral replication and to exert effects on immune function. There are two distinct types of IFN. Type I IFN is produced by a variety of cell types in response to viral infection and includes IFN-α and -β. Typically, IFN-α is produced by leukocytes such as monocytes and macrophages while fibroblasts and epithelial cells are the major source of IFN-β. Type I IFNs share a high degree of amino acid homology, bind to the same cell surface receptor and there biological functions are resistant to heat and low pH treatment. (Weissmann and Weber, 1986)

In contrast, the production of Type II IFN-γ in mammals is restricted to activated T cells and NK cells and is encoded by a gene that is unrelated to those which express IFN-α or IFN-β. Features that distinguish IFN-γ from -α/β include their binding to different cell surface receptors and that the former is exquisitely sensitive to heat and low pH treatment (Weissmann and Weber, 1986). Another distinction is the ability of IFN-γ, but not IFN-α or IFN-β, to stimulate macrophages to produce reactive nitrogen intermediates such as nitric oxide, nitrate and nitrite (Fast et al, 1993; Huang et al, 1993).

Chicken T cells produce IFN following stimulation with antigen or mitogen (Prowse and Pallister, 1989; Lowenthal et al, 1993; Pusztai et al, 1986; Weiler and von Bulow, 1987; Dijkmans et al, 1990) as measured by the ability to protect chick embryonic fibroblasts (CEF) from virus-mediated lysis. There has been controversy as to whether this IFN activity is the Type I or Type II equivalent of mammalian IFN (Lillehoj et al, 1992). In fact, the existence of IFN-γ in avian species has been questioned (Dijkmans et al, 1990).

The gene for chicken Type I IFN (ChIFN-α) has recently been cloned (Sekellick et al, 1994) and when the protein was compared to mammalian IFNs it was shown to have 20–24% amino acid sequence identity to Type I IFNs, whereas it was unrelated to known mammalian IFN-γ polypeptides. Furthermore, recombinant ChIFN-α was shown to have antiviral activity, but lacked macrophage activating function in that it was unable to induce nitrite secretion in monocytes (Schultz et al, 1995), consistent with the properties of mammalian Type I IFN.

In work leading up to the present invention, the inventors have generated several unique chicken T cell lines from reticuloendothelinsis virus (REV)-transformed spleen cell cultures (Lowenthal et al, 1995a,b). These T cell lines were cloned from single cells that expressed the T cell markers CD3 and CD4/CD8. The inventors have shown that some of these T cell clones constitutively produce high levels of an interferon having the properties of IFN-γ as determined by the ability of their supernatants to prevent virus-mediated lysis of chicken embryonic fibroblasts (CEF), lability of the IFN activity to heat and low pH and the ability of these supernatants to induce nitrite production by chicken macrophages.

The inventors have generated a cDNA library from one of the cloned T cell lines producing an interferon-γ activity and successfully isolated and sequenced a nucleic acid molecule which encodes, or is complementary to a nucleic acid molecule which encodes avian IFN-γ (hereinafter referred to as "ChIFN-γ"). Recombinant genetic constructs comprising the isolated nucleic acid molecule of the present invention have been produced and expressed in transformed cells and immunoreactive molecules, in particular polyclonal and monoclonal antibodies have been produced to the recombinant IFN-γ polypeptide produced therefrom. Surprisingly, the IFN-γ of the present invention possesses many useful features, including the ability to promote growth of an avian species or to prevent weight loss during pathogenic infections when administered thereto by any means, in addition to the ability to act as an immunomodulatory molecule across species boundaries.

Accordingly, one aspect of the present invention provides an isolated nucleic acid molecule which encodes, or is complementary to a nucleic acid molecule which encodes, an avian cytokine polypeptide or a functional or immunologically-interactive homologue, analogue or derivative thereof, wherein said polypeptide is a Type II interferon or a Type II interferon-like molecule.

The term "avian" means a member of the class of vertebrates commonly referred to as birds. As used herein, the term "avian" includes both sexes and all developmental stages of poultry species, domestic birds and game birds selected from the list comprising chickens, turkeys, bantams, quails, guinea fowl, ducks, geese, ostriches, emus, pigeons, canaries, budgerigars, parrots and finches, amongst others.

Hereinafter the term "cytokine polypeptide" shall be taken to refer to a polypeptide molecule comprising at least one subunit of a biologically-active protein which possesses one or more of the characteristic biological features of a cytokine, in particular the ability to affect the functions of a cell which functions in the immune system of an animal.

Hereinafter the term "Type II interferon polypeptide" or "Type II interferon-like polypeptide" shall be taken to refer to a cytokine polypeptide as hereinbefore defined wherein said cytokine possesses at least one, preferably at least two, more preferably at least three, even more preferably at least four, still even more preferably at least five and most preferably six of the following characteristic properties:

(i) It is capable of preventing virus-mediated lysis of an avian cell such as, but not limited to a chicken embryonic fibroblast cell or a turkey embryonic fibroblast cell;

(ii) It is sensitive to treatment comprising high temperature, preferably temperatures of at least 50° C., more preferably at least 60° C.;

(iii) It is sensitive to exposure to low pH, preferably pH values between 1 and 6, more preferably pH values between 1 and 3, in particular a pH value of 2.0;

(iv) It is capable of inducing macrophages to secrete reactive nitrogen intermediates such as nitrite, nitrate or nitric oxide, amongst others;

(v) It functions as an immunomodulatory molecule in an avian species; and (vi) It functions as a growth-enhancing or growth-promoting agent in an avian species.

A Type II interferon-like molecule will further possess characteristics not normally associated with an avian Type II interferon molecule as defined herein, however possesses sufficient similarity to a Type II interferon molecule to be immunologically cross-reactive thereto, or to be at least 40% similar thereto at the amino acid sequence level.

References herein to "Type II interferon polypeptide" or "Type II interferon-like polypeptide" shall also be taken to include all possible fusion molecules between a said polypeptide as hereinbefore defined and another polypeptide, in particular a Type I interferon molecule such as IFN-α or IFN-β or, alternatively, a second Type II interferon or Type III interferon-like molecule. In a preferred embodiment however, references contained herein to "Type II interferon polypeptide" or "Type II interferon-like polypeptide" indicate an avian IFN-γ polypeptide or a fusion molecule comprising same or a derivative, homologue or analogue thereof.

As used herein, the term "immunomodulatory molecule" shall be taken to refer to a polypeptide, protein or other substance which is at least capable of altering the immune response of an animal to a disease-promoting agent such as an infectious agent or a cancer-inducing agent, amongst others. Accordingly, the present invention is particularly directed to avian Type II interferon polypeptides which are at least capable of altering an immune response in a bird or alternatively a fusion molecule comprising same which is at least capable of altering an immune response in a bird or mammal to an antigen or infectious agent such as, but not limited to infectious bronchitis virus, avian infectious laryngeotracheitis virus, infectious bronchitis virus, Newcastle disease virus, Marek's Disease virus, chicken anemia virus, avian influenza virus, E. coli, Salmonella ssp., Eimeria ssp. or Mycoplasma ssp. amongst others, to alleviate symptoms associated therewith, in particular reduced growth performance.

As used herein, the term "growth-enhancing or growth promoting agent" or similar term shall be taken to refer to the capability of a substance to lead to increased weight in an avian species or to prevent weight losses normally detectable during or following pathogenic infection of an avian species, when administered thereto, either in any form such as a vaccine, adjuvant, recombinant polypeptide, synthetic polypeptide, pharmaceutical composition or therapeutic foodstuff, amongst others.

In a preferred embodiment, the present invention provides an isolated nucleic acid molecule which encodes, or is complementary to a nucleic acid molecule which encodes, an avian cytokine polypeptide a functional or immunologically-interactive homologue, analogue or derivative thereof, wherein said polypeptide is a Type II interferon or a Type II interferon-like molecule and wherein said avian is a species of poultry selected from the list comprising chickens, ducks, geese, turkeys, bantams, quails or guinea fowl, amongst others.

In a particularly preferred embodiment, the nucleic acid molecule of the present invention is derived from chickens.

As used herein, the term "derived from" shall be taken to indicate that a particular integer or group of integers has originated from the species specified, but has not necessarily been obtained directly from the specified source.

In a more particularly preferred embodiment, the present invention provides an isolated nucleic acid molecule which encodes, or is complementary to a nucleic acid molecule which encodes, a chicken IFN-γ or IFN-γ-like polypeptide or a functional or inmunologically-interactive homologue, analogue or derivative thereof.

The nucleic acid molecule of the present invention most preferably comprises a sequence of nucleotides substantially the same as or complementary to the nucleotide sequence set forth in SEQ ID NO:1 or a homologue, analogue or derivative thereof including any single or multiple nucleotide substitutions, deletions and/or additions thereto.

For the present purpose, "homologues" of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example carbohydrates, radiochemicals including radionucleotides, reporter molecules such as, but not limited to DIG, alkine phosphatase or horseradish peroxidase, amongst others.

"Derivatives" of a nucleotide sequence set forth herein shall be taken to refer to any isolated nucleic acid molecule which contains significant sequence similarity to said sequence or a part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in its place.

For the purposes of nomenclature, the nucleotide sequence set forth in SEQ ID NO: 1 relates to the chicken IFN-γ cDNA sequence, referred to hereinafter as the "ChIFN-γ gene", which is expressed in activated T cells and NK cells to produce a polypeptide which is capable of stimulating macrophages to produce reactive nitrogen intermediates such as nitric oxide, nitrate or nitrite.

Reference herein to a "gene", including the "ChIFN-γ gene", is to be taken in its broadest context and includes:

(i) a classical genomic gene consisting of transcriptional and/or translational regulatory sequences and/or a coding region and/or non-translated sequences (i.e. introns, 5'- and 3'- untranslated sequences); and/or (ii) mRNA or cDNA corresponding to the coding regions (i.e. exons) optionally comprising 5'- or 3'-untranslated sequences of the gene.

The term "gene" is also used to describe synthetic or fusion molecules encoding all or part of a functional product. Synthetic ChIFN-γ genes may be derived from a naturally-occurring ChIFN-γ gene by standard recombinant techniques. Generally, an a ChIFN-γ gene may be subjected to mutagenesis to produce single or multiple nucleotide substitutions, deletions and/or additions. Nucleotide insertional derivatives of the ChIFN-γ cytokine gene of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence although random insertion is also possible with suitable screening of the resulting product. Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, substituents are designed to alter one amino acid for another similar acting amino acid, or amino acid of like charge, polarity, or hydrophobicity.

The present invention extends to the isolated nucleic acid molecule when integrated into the genome of a cell as an addition to the endogenous cellular complement of cytokine genes. Optionally, the integrated nucleic acid molecule contains a promoter sequence derived from the same or another gene, which regulates the expression of the IFN-γ gene sequence contained therein.

The subject invention clearly contemplates a related Type II interferon gene or interferon-like gene derived from an avian source in addition to chickens, such as but not limited to, any poultry species, domestic bird or game bird selected from the list comprising turkeys, bantams, quails, guinea fowl, ducks, geese, ostriches, emus, pigeons, canaries, budgerigars, parrots and finches, amongst others. The present invention extends further to said avian Type II interferon genes or Type II interferon-like genes derived from embryo tissues or cultured cells of avian origin.

Preferably, the related avian Type II interferon gene, or Type II interferon-like gene, has utility in therapeutic foodstuffs or vaccine compositions as an immunomodulatory molecule or growth-enhancing agent for the treatment of animals such as, but not limited to birds, mammals, or humans.

Those skilled in the relevant art will easily be able to isolate one or more related Type II interferon or Type II interferon-like gene sequences without undue experimentation, when provided with the nucleotide sequence set forth in SEQ ID NO: 1.

As a consequence, the present invention extends to any avian Type II interferon genes or interferon-like genes and any functional genes, mutants, derivatives, parts, fragments, homologues or analogues thereof or non-functional molecules but which are at least useful as, for example, genetic probes, or primer sequences in the enzymatic or chemical synthesis of said gene, or in the generation of immunologically interactive recombinant molecules, subject to the proviso that said avian Type II interferon gene or interferon-like gene is at least 40% related to the nucleotide sequence set forth in SEQ ID NO:1.

The present invention clearly encompasses a genomic clone equivalent of the nucleic acid molecule set forth in SEQ ID NO:1 wherein said genomic clone comprises at least a part of the ChIFN-γ gene.

Accordingly, an alternative embodiment of the present invention provides an isolated nucleic acid molecule which comprises a sequence of nucleotides corresponding or complementary to the sequence of nucleotides set forth in SEQ ID NO:1, or having at least about 40%, preferably at least about 55%, still more preferably at least about 65%, yet still more preferably at least about 75–80% and even still more preferably at least about 85–95% nucleotide similarity to all or a part thereof.

In a particularly preferred embodiment, the present invention provides an isolated nucleic acid molecule which encodes or is complementary to a nucleic acid molecule which encodes an avian cytokine polypeptide or a functional or immunologically-interactive homologue, analogue or derivative thereof, wherein said polypeptide is a Type II interferon or a Type II interferon-like molecule and wherein said nucleic acid molecule further comprises a sequence of nucleotides which is at least 40% identical to the nucleotide sequence set forth in SEQ ID NO:1.

In a most preferred embodiment of the invention, said Type II interferon molecule is IFN-γ, in particular ChIFN-γ.

In an alternative embodiment, the present invention provides an isolated nucleic acid molecule which encodes, or is complementary to a nucleic acid molecule which encodes, an avian Type II interferon or avian Type-II interferon-like polypeptide and which is capable of hybridising under at least low stringency conditions to the nucleic acid molecule set forth in SEQ ID NO:1, or to a complementary stand thereof.

Preferably, said nucleic acid molecule is capable of hybridising under at least moderate stringency conditions, even more preferably under at least high level stringency conditions.

In a most preferred embodiment of the invention, said Type II interferon is IFN-γ, in particular ChIFN-γ.

For the purposes of defining the level of stringency, a low stringency is defined herein as being a hybridisation and/or a wash carried out in 6×SSC buffer, 0.1% (w/v) SDS at 28° C. A moderate stringency is defined herein as being a hybridisation and/or wash carried out in 2×SSC buffer, 0.1% (w/v) SDS at a temperature in the range 45° C. to 65° C. A high stringency is defined herein as being a hybridisation and/or wash carried out in 0.1×SSC buffer, 0.1% (w/v) SDS at a temperature of at least 65° C.

Generally, the stringency is increased by reducing the concentration of SSC buffer, and/or increasing the concentration of SDS and/or increasing the temperature of the hybridisation and/or wash. Those skilled in the art will be aware that the conditions for hybridisation and/or wash may vary depending upon the nature of the hybridisation membrane or the type of hybridisation probe used. Conditions for hybridisations and washes are well understood by one normally skilled in the art For the purposes of clarification of the parameters affecting hybridisation between nucleic acid molecules, reference is found in pages 2.10.8 to 2.10.16. of Ausubel et al. (1987), which is herein incorporated by reference.

In a further alternative embodiment, the present invention provides an isolated nucleic acid molecule which encodes or is complementary to a nucleic acid molecule which encodes an avian cytokine polypeptide or a functional or immunologically-interactive homologue, analogue or derivative thereof, wherein:

(i) said polypeptide is a Type II interferon or a Type II interferon-like molecule;

(ii) said nucleic acid molecule comprises a sequence of nucleotides which is at least 40% identical to the nucleotide sequence set forth in SEQ ID NO:1; and (iii) said nucleic acid molecule is capable of hybridising under at least low stringency conditions to the nucleic acid molecule set forth in SEQ ID NO:1, or to a complementary strand thereof.

Preferably, said Type II interferon molecule is IFN-γ, in particular ChIFN-γ.

A second aspect of the present invention provides a method for identifying an avian Type II interferon genetic sequence, or avian Type II interferon-like genetic sequence or a homologue, analogue or derivative thereof.

In one embodiment, said method comprises contacting genomic DNA, or mRNA, or cDNA with a hybridisation effective amount of a Type II interferon genetic sequence, or a functional part thereof, and then detecting said hybridisation.

The related genetic sequence may be in a recombinant form, in a virus particle, bacteriophage particle, yeast cell, animal cell, or a plant cell. Preferably, the related genetic sequence originates from an avian species. More preferably, the related genetic sequence originates from an avian species selected from the list comprising chickens, turkeys, bantams, quails, guinea fowl, ducks, geese, ostriches, emus, pigeons, canaries, budgerigars, parrots and finches, amongst others. In a particularly preferred embodiment the related genetic sequences originate from chickens.

Preferably, the avian Type II interferon genetic sequence (i.e. probe or latter genetic sequence) comprises a sequence of nucleotides or at least 50 nucleotides, more preferably at least 100 nucleotides and even more preferably at least 500 nucleotides derived from the nucleotide sequence set forth in SEQ ID NO:1or its complement or a homologue, analogue or derivative thereof.

Preferably, the latter genetic sequence is labelled with a reporter molecule capable of giving an identifiable signal (e.g. a radioisotope such as $^{32}$P or $^{35}$S or a biotinylated molecule).

An alternative embodiment of the present invention provides a method for identifying an avian Type II interferon genetic sequence, or avian Type II interferon-like genetic sequence or a homologue, analogue or derivative thereof comprising contacting two non-complementary nucleic acid "primer molecules" of at least 12 nucleotides in length derived from the nucleotide sequence of an avian Type II cytokine gene with a nucleic acid template molecule comprising nucleotide sequences related to the primer molecule sequences and amplifying specific nucleic acid molecule copies of the template molecule in a polymerase chain reaction.

According to this embodiment, the first primer molecule is preferably derived from the sense stand of an avian IFN-γ gene such as the ChIFN-γ gene and in particular from the nucleotide sequence set forth in SEQ ID NO:1 or a homologue, derivative or analogue thereof and the second primer molecule is preferably derived from the antisense strand of an avian IFN-γ gene such as the ChIFN-γ gene and in particular from the complement of the nucleotide sequence set forth in SEQ ID NO:1 or a homologue, derivative or analogue thereof. Accordingly, both primers hybridise to said template molecule such that, in the presence of a DNA polymerase enzyme, a cofactor and appropriate substrate, DNA synthesis occurs in the 5' to 3' direction from each primer molecule towards the position on the DNA where the other primer molecule is hybridised, thereby amplifying the intervening DNA.

The nucleic acid primer molecule may further consist of a combination of any of the nucleotides adenine, cytidine, guanine, thymidine, or inosine, or functional analogues or derivatives thereof, capable of being incorporated into a polynucleotide molecule provided that it is capable of hybridising under at least low stringency conditions to the nucleic acid molecule set forth in SEQ ID NO:1.

The nucleic acid primer molecules may further be each contained in an aqueous pool comprising other nucleic acid primer molecules. More preferably, the nucleic acid primer molecule is in a substantially pure form.

The nucleic acid template molecule may be in a recombinant form, in a virus particle, bacteriophage particle, yeast cell, animal cell, or a plant cell. Preferably, the related genetic sequence originates from an avian cell, tissue, or organ. More preferably, the related genetic sequence originates from a chicken cell, tissue or organ.

A third aspect of the present invention provides a genetic construct comprising a nucleic acid molecule which encodes or is complementary to a nucleic acid molecule which encodes an avian cytokine polypeptide or a homologue, analogue or derivative thereof, wherein said polypeptide is a Type II interferon or a Type II interferon-like molecule.

In a preferred embodiment, said polypeptide is IFN-γ.

In a particularly preferred embodiment, the present invention provides a genetic construct comprising the nucleotide sequence set forth in SEQ ID NO:1 or a homologue, analogue or derivative thereof.

The genetic constructs of the present invention are particularly useful for the production of the recombinant cytokine polypeptide encoded therein, when introduced into a cell line or a virus particle and under conditions suitable for gene expression to occur. Such conditions will depend upon the cell line and the expression vector used in each case and would be well-known to the person skilled in the art.

Any number of expression vectors can be employed depending on whether expression is required in a eukaryotic or prokaryotic cell or a virus particle. Furthermore, it is well-known in the art that the promoter sequence used in the expression vector will also vary depending upon the level of expression required and whether expression is intended to be constitutive or regulated.

For expression in eukaryotic cells, the genetic construct generally comprises, in addition to the nucleic acid molecule of the invention, a promoter and optionally other regulatory sequences designed to facilitate expression of said nucleic acid molecule. The promoter may be derived from a genomic clone encoding an avian Type II interferon molecule, in particular ChIFN-γ or, alternatively, it may be a heterologous promoter from another source. Promoter sequences suitable for expression of genes in eukaryotic cells are well-known in the art. In a preferred embodiment, the promoter is capable of expression in an avian cell.

Examples of eukaryotic cells contemplated herein to be suitable for expression include avian, mammalian, yeast, insect, plant cells or cell lines such as COS, VERO, HeLa, mouse C127, Chinese hamster ovary (CHO), WI-38, baby hamster kidney (BHK) or MDCK cell lines. Such cell lines are readily available to those skilled in the art.

In connection with this invention, a nucleic molecule comprising the nucleotide sequence set forth in SEQ ID NO:1 has been cloned into the plasmid vector pCDNA3, which is suitable for expression in eukaryotic COS cells, to produce the plasmid pCDNA3/avian G-IFN. Isolated COS cells containing the pCDNA3/avian G-IFN genetic construct have been deposited on Feb. 28, 1995 pursuant to and in satisfaction of the Budapest Treaty on the International Recognition of the Deposit of Microorganisms for the Purposes of Patent Procedure, with the Australian Government Analytical Laboratories (AGAL), 1 Suakin Street, Pymble, New South Wales 2073, Australia, under AGAL Accession No. N95/12388.

The prerequisite for producing intact polypeptides in *E. coli* is the use of a strong promoter with an effective ribosome binding site. Typical promoters suitable for expression in bacterial cells such as *E. coli* include, but are not limited to, the lacz promoter, temperature-sensitive $\lambda_L$ or $\lambda_R$ promoters, T7 promoter or the IPTG-inducible tac promoter. A number of other vector systems for expressing the nucleic acid molecule of the invention in *E. coli* are well-known in the art and are described for example in Ausubel et al (1987) or Sambrook et al (1989).

Numerous plasmids with suitable promoter sequences for expression in bacteria and efficient ribosome binding sites have been described, such as for example, pKC30 ($\lambda_L$: Shimatake and Rosenberg, 1981), pKK173-3 (tac: Amanm and Brosius, 1985), pET-3 (T7: Studier and Moffat, 1986) or the pQE series of expression vectors (Qiagen, CA), amongst others.

Suitable prokaryotic cells include corynebacterium, salmonella, *Escherichia coli,* Bacillus sp. and Pseudomonas sp, amongst others. Bacterial strains which are suitable for the present purpose are well-known in the relevant art (Ausubel et al, 1987; Sambrook et al, 1989).

In connection with this invention, a nucleic molecule comprising the nucleotide sequence set forth in SEQ ID NO:1 has been cloned into a plasmid vector suitable for expression in a bacterial cell and transformed into the bacterium *Escherichia coli* to produce *E. coli* strain pQE ChIFN-γ. The *E. coli* strain pQE ChIFN-γ has been deposited on Feb. 16, 1996 pursuant to and in satisfaction of the Budapest Treaty on the International Recognition of the Deposit of Microorganisms for the Purposes of Patent Procedure, with the Australian Government Analytical Laboratories (AGAL), 1 Suakin Street, Pymble, New South Wales 2073, Australia, under AGAL Accession No. N96/9464.

In an alternative embodiment, the present invention extends to a genetic construct comprising a nucleic acid molecule which encodes or is complementary to a nucleic acid molecule which encodes an avian cytokine polypeptide or a homologue, analogue or derivative thereof, wherein said polypeptide is a fusion polypeptide between a Type II interferon or Type II interferon-like molecule and either a second Type II interferon or interferon-like molecule or a Type I interferon selected from the list comprising IFN-α, IFN-β, Ch IFN-α or Ch IFN-β, amongst others.

Preferably, said Type II interferon is IFN-γ, in particular Ch IFN-γ.

In order to produce a fusion polypeptide, the nucleic acid molecule which encodes a first coding region comprising an avian cytokine polypeptide or a homologue, analogue or derivative thereof is cloned adjacent to a second coding region, optionally separated by a spacer nucleic acid molecule such that the first coding region and the second coding region are in the same open reading frame, with no intervening stop codons between the two coding regions. When translated, the polypeptide thus produced comprises a fusion between the polypeptide products of the first and second coding regions. A genetic construct which encodes a fusion polypeptide further comprises at least one start codon and one stop codon, capable of being recognised by the cell's translational machinery in which expression is intended. Methods for the production of a fusion polypeptide are well-known to those skilled in the art.

A still further aspect of the present invention provides a recombinant avian cytokine polypeptide or a functional or immunologically-interactive homologue, analogue or derivative thereof, wherein said polypeptide is a Type II interferon or a Type II interferon-like molecule.

By "recombinant avian cytokine" or related term "recombinant molecule" is meant a glycosylated or unglycosylated polypeptide molecule, including a fusion polypeptide, with or without other associated molecules (eg. lipids) produced by recombinant means such as presence of a DNA molecule in an expression vector in the correct reading frame relative to a promoter and introducing the resultant recombinant expression vector into a suitable host and growing said host under conditions appropriate for expression and, if necessary, transportation of ale recombinant protein or its derivative from said host and then purifying the recombinant molecule.

In a particularly preferred embodiment of the present invention, there is provided a recombinant polypeptide comprising a sequence of amino acids which is substantially the same as the amino acid sequence set forth in SEQ ID NO:2 or is at least 40% identical to same. The present invention extends to any derivatives of the avian cytokine polypeptide set forth in SEQ ID NO:2.

For the purposes of nomenclature, the amino acid sequence set forth in SEQ ID NO:2 is chicken IFN-γ (ChIFN-γ) polypeptide which is expressed in activated T cells and NK cells to produce a polypeptide which is capable of stimulating macrophages to produce reactive nitrogen intermediates such as nitric oxide, nitrate or nitrite.

Derivatives of an avian Type II interferon polypeptide or interferon-like polypeptide include single or multiple amino acid substitutions, deletions and/or additions to the molecule. Conveniently, these are prepared by first making single or multiple nucleotide substitutions, deletions and/or additions to the nucleic acid molecule encoding the avian cytokine. Alternatively, once the amino acid sequence is known, amino acids can be chemically added by established techniques and in any sequence required to give the desired mutant. All such derivatives are encompassed by the present invention.

Amino acid insertional derivatives of the avian Type II interferon or interferon-like polypeptide of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with Table 1.

Where a derivative avian cytokine is produced by amino acid substitution, the amino acids are generally replaced by other amino acids having like properties, such as hydrophobicity, hydrophobicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues and a corresponding insertion of two residues.

For convenience and by way of shorthand notation, reference herein to an avian cytokine, in particular an avian Type II interferon such as IFN-γ, Ch IFN-γ or an avian interferon-like polypeptide includes reference to any derivatives thereof as contemplated above.

TABLE 1

Suitable residues for amino acid substitutions

| Original Residue | Exemplary Substitutions |
|---|---|
| Ala | Ser |
| Arg | Lys |
| Asn | Gln; His |
| Asp | Glu |
| Cys | Ser |
| Gln | Asn; Glu |
| Glu | Asp |
| Gly | Pro |
| His | Asn; Gln |
| Ile | Leu; Val |
| Leu | Ile; Val |
| Lys | Arg; Gln; Glu |
| Met | Leu; Ile; Val |
| Phe | Met; Leu; Tyr |
| Ser | Thr |
| Thr | Ser |
| Trp | Tyr |
| Tyr | Trp; Phe |
| Val | Ile; Leu; Met |

The amino acid variants referred to above may be readily made using synthetic peptide techniques well known in the art, such as solid phase peptide synthesis and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Azzabell et al (1987) or Sambrook et al (1989).

Other examples of recombinant or synthetic mutants and derivatives of the avian Type II interferon polypeptide of the present invention include single or multiple substitutions, deletions and/or additions of any molecule associated with the enzyme such as carbohydrates, lipids and/or proteins or polypeptides.

A further aspect of the invention provides a method of producing a recombinant avian Type II interferon or Type II interferon-like molecule in a cell comprising expressing in said cell a nucleic acid molecule which encodes or is complementary to a nucleic acid molecule which encodes said avian cytokine.

In a related embodiment, the present invention provides a method of producing a recombinant avian Type II interferon or interferon-like molecule in a cell comprising the steps of:

(i) introducing into said cell a genetic construct comprising a nucleic acid molecule which encodes or is complementary to a nucleic acid molecule which encodes said avian cytokine, placed under the control of a suitable promoter sequence;

(ii) culturing said cell for a time and under conditions sufficient for said nucleic acid molecule to be expressed; and (iii) optionally isolating from said cell said recombinant cytokine molecule.

In a further related embodiment, the present invention extends to a method of producing a recombinant avian cytokine molecule in a cell comprising introducing into said cell a genetic construct comprising a nucleic acid molecule which encodes or is complementary to a nucleic acid molecule which encodes an avian cytokine polypeptide or a homologue, analogue or derivative thereof, wherein said polypeptide is a fusion polypeptide between a first Type II interferon or Type II interferon-like molecule and a second Type II interferon or a Type I interferon select from the list comprising IFN-α, IFN-β, Ch IFN-α or Ch IFN-β, amongst others.

Preferably, said method further comprises the step of introducing said genetic construct into said cell prior to the step of obtaining expression thereof.

According to the foregoing embodiments described in this aspect of the invention, the recombinant cytokine or Type II interferon or interferon-like molecule is preferably an IFN-γ polypeptide molecule or a fusion molecule comprising same. In a particularly preferred embodiment, the cytokine is the ChIFN-γ polypeptide set forth in SEQ ID NO:2 or a homologue, analogue or derivative thereof or a fusion molecule comprising same.

For optimum expression in a particular tissue or under specified conditions, the nucleic acid molecule may be placed operably under the control of a promoter sequence such as those discussed supra. Suitable cells and virus particles for this purpose are also discussed supra. Promoter sequences and culture conditions for cells or virus particles which produce high levels of expression will be well-known to those skilled in the relevant art.

A further aspect of the invention provides an isolated cell which expresses an endogenous or recombinant avian cytokine polypeptide or a functional or immunologically-interactive homologue, analogue or derivative thereof, wherein said polypeptide is a Type II interferon or a Type II interferon-like molecule.

In a preferred embodiment, the present invention provides an isolated cell which expresses an avian cytokine, wherein said cytokine is a Type II interferon or a Type II interferon-like molecule.

More preferably, said cytokine is a recombinant molecule, for example a fusion polypeptide between a Type II interferon molecule and a second cytokine molecule.

In a most preferred embodiment, the Type II interferon molecule according to this aspect of the invention is IFN-γ, in particular Ch IFN-γ or a homologue, analogue or derivative thereof.

The isolated cell may be an isolated eukaryotic cell which expresses a non-recombinant form of said cytokine, Type II interferon or Type II interferon-like molecule.

In connection with this invention, an isolated T-cell clone designated as CC8.1h which expresses the ChIFN-γ gene has been deposited on Oct. 10, 1994 pursuant to and in satisfaction of the Budapest Treaty on the International Recognition of the Deposit of Microorganisms for the Purposes of Patent Procedure, with the Australian Government Analytical Laboratories (AGAL), 1 Suakin Street, Pymble, New South Wales 2073, Australia, under the Accession No. N94/46035.

Alternatively, the isolated cell may be a transformed eukaryotic or prokaryotic cell which expresses a recombinant cytokine, Type II interferon or Type II interferon-like molecule from a genetic construct, such as those discussed supra, which has been introduced thereto. Means for introducing genetic constructs into a cell will be well-known to those skilled in the art.

Accordingly, by way of example, there is provided in a most particularly preferred embodiment, an isolated bacterial cell expressing recombinant ChIFN-γ, wherein said cell has been deposited with the Australian Government Analytical Laboratory on Feb. 16, 1996 under AGAL Accession No. N96/9464.

Also by way of example, the present invention provides an isolated eukaryotic cell expressing recombinant ChIFN-γ, wherein said cell has been deposited with the Australian Government Analytical Laboratory on Feb. 28, 1995 under AGAL Accession No. N95/12388.

In a further embodiment, the present invention extends to an isolated cell comprising a genetic construct as hereinbefore defined.

Means for isolating a cell which expresses an endogenous or recombinant avian cytokine such as a Type II interferon or interferon-like molecule will be well-known to those skilled in the art.

The cells of the present invention are useful as a source of purified avian cytokines, in particular Type II interferon molecules or interferon-like molecules.

The recombinant avian Type II interferon or interferon-like molecules contemplated herein or cells expressing same, will find particular application in the intensive livestock industries such as the live animal export trade, feedlots and intensive rearing industries. In particular, livestock such as poultry, domestic birds and game birds are highly susceptible to infectious diseases, such as those transmitted by viruses, bacteria or mycoplasma. Important viral infectious agents include infectious bursal disease virus, avian infectious bronchitis virus, avian infectious laryngeotracheitis virus, infectious bronchitis virus, Newcastle disease virus, Marek's Disease virus, chicken anemia virus or avian influenza virus, amongst others. Important bacterial agents include E. coli, Salmonella ssp. or Eimeria ssp., amongst others.

Whilst not being bound by any theory or mode of action, avian cytokines such as Type II interferons or interferon-like molecules, in particular ChIFN-γ induce macrophages to become activated, as measured by the increased expression of Class II molecules on their surfaces and/or the increased secretion of active nitrogen intermediates such as nitrites, thereby increasing the capacity of the immune system to destroy invading pathogens and to enhance the immune response thereto.

Accordingly, in a further aspect of the present invention there is provided a method of treatment or prophylaxis of poultry, domestic birds or game birds exposed to or infected with a pathogenic organism, said method comprising administering to said animal an immunomodulatingly effective amount of an avian cytokine or a derivative thereof for a time and under conditions sufficient to maintain, stimulate or enhance the immunoresponsiveness of said animal.

Preferably, said avian cytokine is a recombinant molecule.

As used herein, the term "immunomodulatingly effective amount" is an amount of cytokine sufficient to effect immunomodulation in a target animal, i.e. to enhance the ability of the immune system to develop an effective immune response or to enhance the immunocompetence of the animal or immunogenicity of an antigen administered thereto.

According to the foregoing embodiment, it is particularly preferred that said avian cytokine is a Type II interferon molecule or Type II interferon-like molecule, in particular IFN-γ.

In a most particularly preferred embodiment, said avian cytokine is ChIFN-γ, such as the ChIFN-γ polypeptide molecule set forth in SEQ ID NO:2 or a homologue, analogue or derivative thereof.

The term "poultry, domestic bird or game bird" as used herein extends to chickens, turkeys, bantams, quails, guinea fowl, ducks, geese, ostriches, emus, pigeons, canaries, budgerigars, parrots and finches, amongst others, provided that the avian cytokines are effective in those animals. Particularly preferred poultry, domestic bird or game birds are chickens and related species.

The present invention is of particular use in the treatment or prophylaxis of poultry, domestic birds or game birds against infection by pathogens selected from the list comprising infectious bursal disease virus, avian infectious bronchitis virus, avian infectious laryngeotracheitis virus, infectious bronchitis virus, Newcastle disease virus, Marek's Disease virus, chicken anemia virus, avian influenza virus, E. coli, Salmonella ssp., Eineria ssp. or Mycoplasma ssp. amongst others.

The avian cytokine of the present invention may be administered throughout the life cycle of a bird for which treatment or prophylaxis is indicated. The developmental stage of the bird during which treatment or prophylaxis is most effective will vary depending upon the nature of the pathogen against which protection is sought, including its mode of transmission and period of highest infectivity. By "period of highest infectivity" is meant the developmental stage of the host during which it is most vulnerable to attack by a particular pathogen and/or during which there is a greater probability of incurring livestock losses or reduced productivity as a result of the pathogen infection. The parameters affecting optimum developmental stages of animals for administration of the subject cytokines will be well-known to those skilled in the art.

Accordingly, the method of treatment or prophylaxis of the present invention extends to administration of the subject avian cytokine at any developmental stage in the life cycle of poultry, domestic or game birds for which treatment or prophylaxis is indicated.

The cytokine of the invention may be administered by any means including for example, by injection either in ovo or post-hatching by injection such as intra-peritoneal, intra-dermal, intramuscular, intra-ocular, intra-venous, sub-cutaneous or other injection means, by ingestion as a medicated foodstuff or therapeutic foodstuff or by introducing to said avian an isolated nucleic acid molecule which encodes or is complementary to a nucleic acid molecule which encodes said cytokine or, alternatively, a vector comprising a genetic construct capable of expressing said cytokine in vivo or in ovo, for example a live recombinant viral vector, live recombinant bacterial vector.

Wherein the cytokine of the invention is administered via the introduction of an isolated nucleic acid molecule encoding said cytokine, such as a DNA or RNA molecule, or a vector comprising a genetic construct capable of expressing said cytokine, the nucleic acid molecule or genetic construct must be transcribed and translated to produce the biologically-active cytokine molecule following its administration to an appropriate avian subject.

In an alternative embodiment, the present invention provides a method of treatment or prophylaxis of poultry, domestic birds or game birds exposed to or infected with a pathogenic organism, said method comprising administering to said animal an immunoresponsive effective amount of a first avian cytokine comprising a Type II interferon or Type II interferon-like molecule in combination with a second avian cytokine molecule, for a time in combination and under conditions sufficient to maintain, stimulate or enhance the immunoresponsiveness of said animal.

Preferably, said first avian cytokine is an IFN-γ molecule in particular Ch IFN-γ. It is also preferred that said second avian cytokine be selected from the list comprising Type I interferons such as, but not limited to, IFN-α, IFN-β, ChIFN-α, ChIFN-β, or a Type II interferon or any other cytokine or cytokine-like molecule.

In a most preferred embodiment, said first avian cytokine and said second avian cytokine are a fusion molecule.

According to this embodiment of the invention, the fire and second avian cytokines interact with the immune system of an animal to further stimulate or enhance the immunoresponsiveness of the immune system against pathogen attack.

Another important application of the cytokines of the present invention is as natural adjuvants for vaccines, particularly for subunit or synthetic peptide vaccines produced by recombinant DNA technology.

The term "adjuvant" as used herein shall be taken to mean a substance that, when administered to an animal in combination with a second substance or antigen, enhances the production of immunointeractive molecules, such as antibodies, which recognise the second substance or antigen molecule. An adjuvant may be used therapeutically to produce antibodies against small amounts of antigen or to prolong the period of antibody production or to increase the amount of antibody produced. Whilst not wishing to be bound by any theory or mode of action, adjuvants work by inducing a local influx of antibody-forming cells to the site of administration.

Accordingly, a further aspect of the present invention provides an adjuvant comprising an avian cytokine molecule, wherein said cytokine is a Type II interferon or interferon-like molecule or a fusion molecule between said Type II interferon molecule and a second cytokine molecule and optionally, a pharmaceutically-acceptable carrier, excipient or diluent.

Preferably, said avian Type II interferon molecule is IFN-γ, in particular ChIFN-γ. In a most particularly preferred embodiment, said ChIFN-γ molecule comprises an amino acid sequence which is substantially the same as the amino acid sequence set forth in SEQ ID NO:2 or at least 40% identical thereto.

Wherein said avian cytokine is a fusion molecule, said second cytokine may be any cytokine molecule which is functional in avian species, in particular IFN-α, IFN-β, ChIFN-α, ChIFN-γ or a Type II inferon molecule or any other cytokine or cytokine-like molecule.

In accordance with the present invention, an avian cytokine such as a Type II interferon or interferon-like molecule, in particular ChIFN-γ, is used in vaccines to enhance the immunogenicity of antigens, particularly in subunit vaccines, leading to increased antibody titre in individual birds, increased protection of birds that are immunised against a specific antigen (i.e. enhanced flock immunity) and/or increased persistence of protective antibodies in immunised birds. A further advantage provided by the present invention is a reduction in the quantity of specific antigen required to effectively immunise animals, thereby leading to reduced production costs.

A still further aspect of the present invention provides a method of enhancing and/or stimulating an immune response to one or more antigens in an animal, said method comprising administering to said animal an immunoresponsive effective amount of an avian cytokine.

In a related embodiment, there is contemplated a vaccine composition for the prophylactic treatment of an avian species comprising an antigen and recombinant avian cytokine or a derivative thereof as described herein. The vaccine may also comprise one or more pharmaceutically acceptable carriers and/or diluents. The carriers and/or diluents are also required to be acceptable for veterinary use.

According to this embodiment of the invention, said prophylactic treatment is intended to vaccinate said avian against a viral or bacterial pathogen selected from the list comprising infectious bursal disease virus, avian infectious bronchitis virus, avian infectious laryngeotracheitis virus, infectious bronchitis virus, Newcastle disease virus, Marek's Disease virus, chicken anemia virus, avian influenza virus, *E. coli*, Salmonella ssp. or Eimeria ssp., amongst others.

According to the foregoing embodiments, it is particularly preferred that said avian cytokine is a Type II interferon molecule or interferon-like molecule, in particular IFN-γ or a fusion polypeptide between avian Type II interferon molecule and a second cytokine. In a most particularly preferred embodiment, said avian cytokine is ChIFN-γ, such as the ChIFN-γ polypeptide molecule set forth in SEQ ID NO:2 or a homologue, analogue or derivative thereof.

The cytokine or vaccine of the invention described according to these embodiments may be administered by any means including for example, by injection either in ovo or post-hatching by injection such as intra-peritoneal, intradermal, intramuscular, intra-ocular, intra-venous, subcutaneous or other injection means, by ingestion as a medicated foodstuff or therapeutic foodstuff.

Advances in slow-release technology and the development of live non-pathogenic bacteria and viruses as delivery vectors for these molecules will ensure their cost-effectiveness when administered to poultry, domestic birds or game birds. They may also be used in nucleic acid vaccination. Accordingly, the avian cytokine or vaccine of the present invention may also be delivered by genetic means. For example, recombinant avian ChIFN-γ may be encoded by a genetic construct present in a delivery system such as a virus, yeast, bacterium, protozoan, insect, avian or mammalian cell. The expression of such a delivery system in a target animal will enable delivery of the recombinant avian cytokine.

According to this embodiment, there is contemplated a genetic construct comprising:

(i) a first nucleotide sequence encoding an avian Type II interferon or interferon-like molecule or a fusion cytokine molecule between said Type II interferon and a second cytokine, placed operably under the control of a first promoter sequence;

(ii) a second nucleotide sequence defining an antigen against which immunisation is required, placed operably under the control of a second promoter sequence; and (iii) a delivery vehicle comprising genetic sequences which facilitate replication of said genetic construct in a delivery cell such as a bacterial, yeast, insect, a protozoan animal or a mammalian cell.

Preferably, said Type II interferon is IFN-γ, in particular ChIFN-γ. It is also preferred that said second cytokine be selected from the list comprising Type I interferons such as IFN-α, IFN-β, ChIFN-α, ChIFN-β or, alternatively, a Type II interferon or interferon-like molecule or any other cytokine or cytokine-like molecule.

According to this embodiment, the delivery cell would not in normal use be harmful or pathogenic to the target animal. Conveniently, attenuated delivery cells are employed. Particularly useful delivery vectors are attenuated viruses and recombinant viral and bacterial vectors.

For example, an attenuated viral vector is used as a live vaccine. The genetic sequence encoding an avian cytokine such as ChIFN-γ or a derivative thereof is cloned into the viral sequence and the recombinant virus used to infect target animals. The recombinant virus causes infection and replicates in the animal cells resulting in production of the recombinant cytokine. The infecting recombinant virus may subsequently be eliminated after production of an immunomodulatingly effective amount of the recombinant cytokine. A similar protocol is adopted with live bacterial carriers. Alternatively, a non-replicating, non-infectious viral vector may be used. A non-replicating viral vector provides a means of introducing a genetic sequence which is transiently capable of expression of the desired cytokine because the non-replicating viral vector is not capable of cell-to-cell transmission.

The present invention provides an opportunity to enhance an immune response in animals and in particular poultry, domestic birds or game birds (such as those described above) by the administration of an avian cytokine, in particular a Type II interferon such as ChIFN-γ or a derivative thereof, either directly or via the expression of recombinant genetic sequences. This is of particular importance since most subunit and synthetic peptide vaccines are only weakly antigenic. The administration of the cytokines may be alone, in combination with an antigen or as a fusion molecule. Administration may be via an attenuated virus, recombinant viral vector or bacterial vector or may be by administration of the cytokine by, for example, injection or oral ingestion (e.g. in medicated foodstuff).

The present invention extends to a veterinary pharmaceutical composition for use in poultry, domestic bird or game birds such as to enhance the immune system or accelerate its maturation or improve its immunocompetence or to facilitate immunomodulation in said birds, said composition comprising a recombinant avian Type II interferon or interferon-like molecule or a fusion molecule between a Type II interferon and a second cytokine fused to an antigen or genetic sequences encoding same and one or more carriers and/or diluents acceptable for veterinary use.

Preferably, where the composition comprises a recombinant avian cytokine as hereinbefore defined, the composition is injected in ovo or post-hatching, or administered via aerosol or ingestion. Where the composition comprises genetic material, it is administered as part of a viral vector, bacterial vector or as a nucleic acid molecule.

Conditions in poultry, domestic bird or game birds for which treatment might be required include infectious disease induced by any viral or bacterial agent such as those discussed supra, cancer, immunosuppression, allergy and to enhance or suppress reproductive systems. Conditions would also include situations where animals are in an immunocompromised state such as during or following stress, due to overcrowding and transport process, changes in climate.

The bird to be treated and the cytokine in the composition might be "homologous" in the sense that both are of the same species, or may be "heterologous" where the avian cytokine is effective in another bird species than the species from which it has been derived. The compositions may also contain other active molecules such as antibiotics or antigen molecules. Combinations of cytokine molecules with antigen molecules may increase the efficacy of vaccines.

The present invention, therefore, extends to a veterinary pharmaceutical composition comprising an immunomodulatingly effective amount of an avian Type II interferon or Type II interferon-like molecule or a fusion molecule between an avian Type II interferon or interferon-like molecule and a second cytokine or genetic sequences capable of expressing same and one or more carriers and/or diluents acceptable for veterinary use.

In a preferred embodiment, said Type II interferon is IFN-γ, in particular ChIFN-γ. Wherein said pharmaceutical composition comprises a fusion molecule, said fusion is preferably a fusion between ChIFN-γ or a homologue, analogue or a derivative thereof and a second cytokine selected from the list comprising Type I interferons such as IFN-α, IFN-β, ChIFN-α, ChIFN-β or a Type II interferon or interferon-like molecule or any other cytokine or cytokine-like molecule.

The active ingredient(s) of the pharmaceutical composition is/are contemplated to exhibit excellent activity in stimulating, enhancing or otherwise facilitating an immune response in an animal species and in particular a poultry, domestic bird or game bird when administered in an amount which depends on the particular case. The variation depends, for example, on the cytokine and, in some cases, the antigen involved in stimulating the immune response. For example, from about 0.5 μg to about 20 mg of a particular cytokine which may be combined with other cytokines, per kilogram of body weight per day may be required. Dosage regimen may be adjusted to provide the optimum therapeutic response. For example, several divided doses may be administered in one or more of daily, weekly or monthly or in other suitable time intervals or the dose may be proportionally reduced as indicated by the exigencies of the situation. The active compound may be administered by injection either in ovo or post-hatching or by oral ingestion in any convenient manner or may be administered via a genetic sequence such as in a viral or bacterial vector.

The active compounds may also be administered in dispersions prepared in glycerol liquid polyethylene glycols, and/or mixtures thereof and in oils. Under ordinary conditions of storage and use, these preparations contain a preservative to prevent the growth of microorganisms.

The pharmaceutical forms suitable for parenteral administration include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, antibiotics, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example.

Sterile injectable solutions are prepared by incorporating the active compounds in the required amount in the appropriate solvent with various of the other ingredients enumerated above, as required, followed by filter sterilisation. Generally, dispersions are prepared by incorporating the various sterilised active ingredient(s) into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Carriers and/or diluents suitable for veterinary use include any and all solvents, dispersion media, aqueous solutions, coatings, antibacterial and antifungal agents, isotonic and absorption delaying agents, and the like. The use of such media and agents for pharmaceutically active substances is well known in the art. Except insofar as any conventional media or agent is incompatible with the active ingredient, use thereof in the composition is contemplated. Supplementary active ingredients can also be incorporated into the compositions. The latter is particularly contemplated as far as the present invention extends to multivalent vaccines or multi-component cytokine molecules.

The pharmaceutical veterinary compositions of the present invention may comprise in addition to an avian Type II interferon or interferon-like molecule or a fusion molecule comprising same, one or more other active compounds such as antigens and/or immune stimulating compounds.

The cytokine may also be delivered by a live delivery system such as using a bacterial expression system to express the cytokine protein in bacteria which can be incorporated into gut flora. Alternatively, a viral expression system can be employed or incorporated into a recombinant vaccine. In this regard, one form of viral expression is the administration of a live vector generally by spray, feed or water where an infecting effective amount of the live vector (e.g. virus or bacterium) is provided to the animal. Another form of viral expression system is a non-replicating virus vector which is capable of infecting a cell but not replicating therein. The non-replicating viral vector provides a means of introducing genetic material for transient expression into a cytokine. The mode of administering such a vector is the same as a live viral vector.

The cytokine molecule of the present invention, in particular ChIFN-γ, is also useful as a growth-enhancing or growth-promoting agent and/or maturation-promoting agent when administered to an avian species such as a species of poultry, domestic bird or a game bird. The present invention is particularly useful as a growth performance enhancer and, as the inventors have demonstrated in the Examples described herein, administration of ChIFN-γ to immature birds leads to significant increases in weight, addition to the prevention of weight loss usually associated with various disease states.

Accordingly, a further aspect of the invention provides a method of enhancing growth performance of an avian species comprising administering to an avian a Type II interferon or interferon-like molecule.

By enhancing growth performance is meant to increase the weight of an avian species or to prevent weight losses therein normally detectable during or following pathogenic infection of an avian species.

Preferably, said Type II interferon molecule is IFN-γ. In a particularly preferred embodiment, said IFN-γ molecule is the ChIFN-γ molecule set forth in SEQ ID NO:2 or a homologue, analogue or derivative thereof.

The avian species may be a healthy or diseased bird selected from the list comprising chickens, turkeys, bantams, quails, guinea fowl, ducks, geese, ostriches, emus, pigeons, canaries, budgerigars, parrots and finches, amongst others.

Methods for the administration of the cytokine of the invention for the purpose of promoting growth or enhancing growth of an avian species are similar to the methods discussed supra for the administration of a vaccine, adjuvant or veterinary pharmaceutical composition.

The recombinant avian Type II interferon or interferon-like molecule of the present invention or a homologue, analogue or derivative thereof, in particular ChIFN-γ, is also useful in the production of immunological interactive molecules such as antibodies or functional derivatives thereof including Fabs or SCABS (single-chain antibodies), antibodies conjugated to an enzyme, radioactive or fluorescent tag, the only requirement being that said immunologically interactive molecules are able to bind to an avian Type II interferon or interferon-like molecule described herein.

Accordingly, a further aspect of the present invention provides an immunologically-interactive molecule which binds to an avian Type II interferon molecule or Type II interferon-like molecule, or a homologue, analogue or derivative thereof.

Preferably, said avian Type II interferon or interferon-like molecule is IFN-γ.

More preferably, said avian Type II interferon or interferon-like molecule is ChIFN-γ.

In an even more preferred embodiment, said inmunologically-interactive molecule binds to a Type II interferon or interferon-like molecule or a homologue, analogue or derivative thereof comprising at least 10 amino acid residues, preferably at least 20 amino acid residues and more preferably at least 50 amino acid residues contained within the amino acid sequence set forth in SEQ ID NO:2 or having at least 40% similarity thereto.

In a most preferred embodiment, said immunologically interactive molecule is an antibody molecule. The antibody molecule may be monoclonal or polyclonal and may be used for developing enzyme-immunosorbent assays for the rapid diagnosis of infectious diseases of poultry, domestic birds or game birds.

According to this embodiment, there is provided an antibody preparation comprising antibodies or derivatives thereof, immunointeractive with either an avian Type II interferon or Type II interferon-like molecule or a derivative thereof or with a fusion molecule between an avian Type II interferon and a second cytokine.

In a preferred embodiment, said Type II interferon is IFN-γ, in particular ChIFN-γ. Said second cytokine may be a Type I interferon molecule selected from the list comprising IFN-α, IFN-β, ChIFN-α, ChIFN-β or, alternatively, a Type II interferon other than ChIFN-α.

Immunoassays are useful in detecting the presence of a cytokine in a target animal, particularly birds, in particular to detect an immune response in which the level of said avian cytokine is altered, for example following infection with a pathogen. As a consequence, such an immunoassay is of particular use in determining whether a bird has been exposed to a pathogen or is currently infected with a pathogen or has a prolonged low-grade pathogenic infection. Immunoassays are also useful for the quantitation of cytokines, in particular for screening genetic stocks for high cytokine-expressing lines with improved disease-resistance to a pathogen. The invention described herein extends to all such uses of immunointeractive molecules and diagnostic assays which require said immunoassays for their performance.

A wide range of immunoassay techniques may be such as those described in U.S. Pat. Nos. 4,016,043, 4,424,279 and 4,018,653. These methods may be employed for detecting a Type II interferon or interferon-like molecule related to ChIFN-γ. By way of example only, an antibody raised against ChIFN-γ is immobilised onto a solid substrate to form a first complex and a biological sample from an animal to be tested for the presence of cytokine brought into contact with the bound molecule. After a suitable period of incubation, for a period of time sufficient to allow formation of an antibody-cytokine secondary complex, a second ChIFN-γ antibody labelled with a reporter molecule capable of producing a detectable signal is then added and incubated, allowing sufficient time for the formation of a tertiary complex of antibody-cytokine-labelled antibody. Any unreacted material is washed away, and the presence of the tertiary complex is determined by observation of a signal produced by the reporter molecule. The results may either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of minor variations will be readily apparent. The antibodies used above may be monoclonal or polyclonal.

The solid substrate is typically glass or a polymer, the most commonly used polymers being cellulose, polyacrylamide, nylon, polystyrene, polyvinyl chloride or polypropylene. The solid supports may be in the form of tubes, beads, discs or microplates, or any other surface suitable for conducting an immunoassay. The binding processes are well-known in the art and generally consist of cross-linking covalently binding or physically adsorbing the molecule to the insoluble carrier.

By "reporter molecule", as used in the present specification, is meant a molecule which, by its chemical nature, produces an analytically identifiable signal which allows the detection of antigen-bound antibody. Detection may be either qualitative or quantitative. The most commonly used reporter molecule in this type of assay are either enzymes, fluorophores or radionuclide containing molecules (i.e. radioisotopes). In the case of an enzyme immunoassay, an enzyme is conjugated to the second antibody, generally by means of glutaraldehyde or periodate. As will be readily recognised, however, a wide variety of different conjugation techniques exist which are readily available to one skilled in the art. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable colour change. It is also possible to employ fluorogenic substrates, which yield a fluorescent product.

Alternatively, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining complex is then exposed to the light of the appropriate wavelength, the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed. It will be readily apparent to the skilled technician how to vary the procedure to suit the required purpose.

The immunologically-interactive molecule is also useful in purifying the recombinant avian cytokine of the present invention. Methods for the affinity purification of proteins using antibodies are well-known to those skilled in the art.

The present invention is further described by reference to the following non-limiting Figures and Examples.

In the Figures:

FIG. 1 is a graphical representation showing sensitivity of chicken IFN to heat and low pH treatment. Supernatant from CEF cultured for 24 hr with Semliki Forest virus was used as a source of IFN-β. Adherent (spleen cells depleted of non-adherent cells), non-adherent (spleen cells depleted of plastic-adherent cells) and whole (unseparated spleen cells), spleen cell populations were cultured for 24 hr with concanavalin A (ConA). Supernatants were heated to 60° C. for 1 hr, exposed to pH2 for 8 hr or kept at 4° C. (control) and then assayed for IFN activity using the CEF assay as described.

Figure 4:
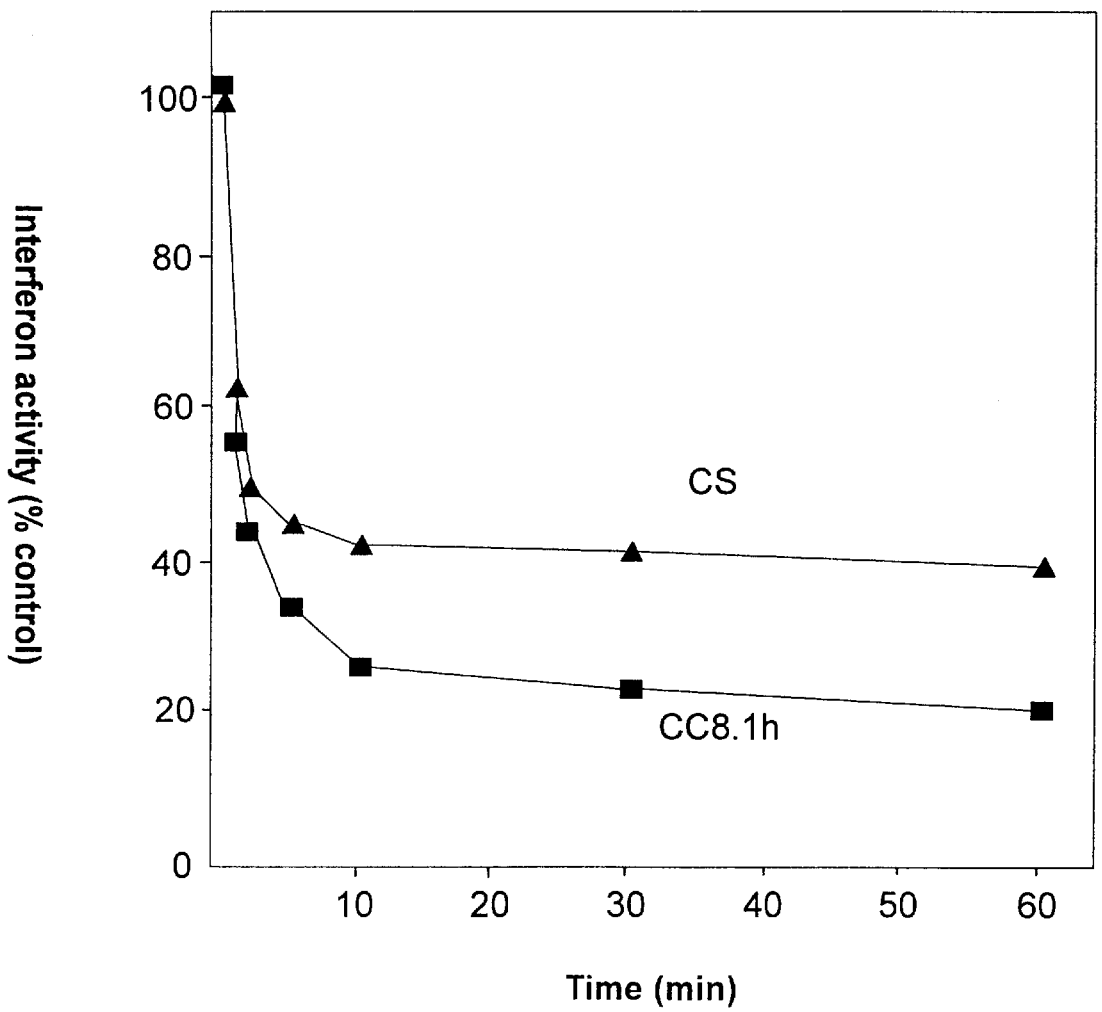

FIG. 4 is a graphical representation showing sensitivity of ChIFN-γ activity to heat Supernatants from CC8.1h (AGAL Accession No. N94/46035) and ConA activated spleen cells (CS) were heated to 60° C. for various periods of time. Residual (heat resistant) IFN activity was measured using the CEF assay.

Figure 5:
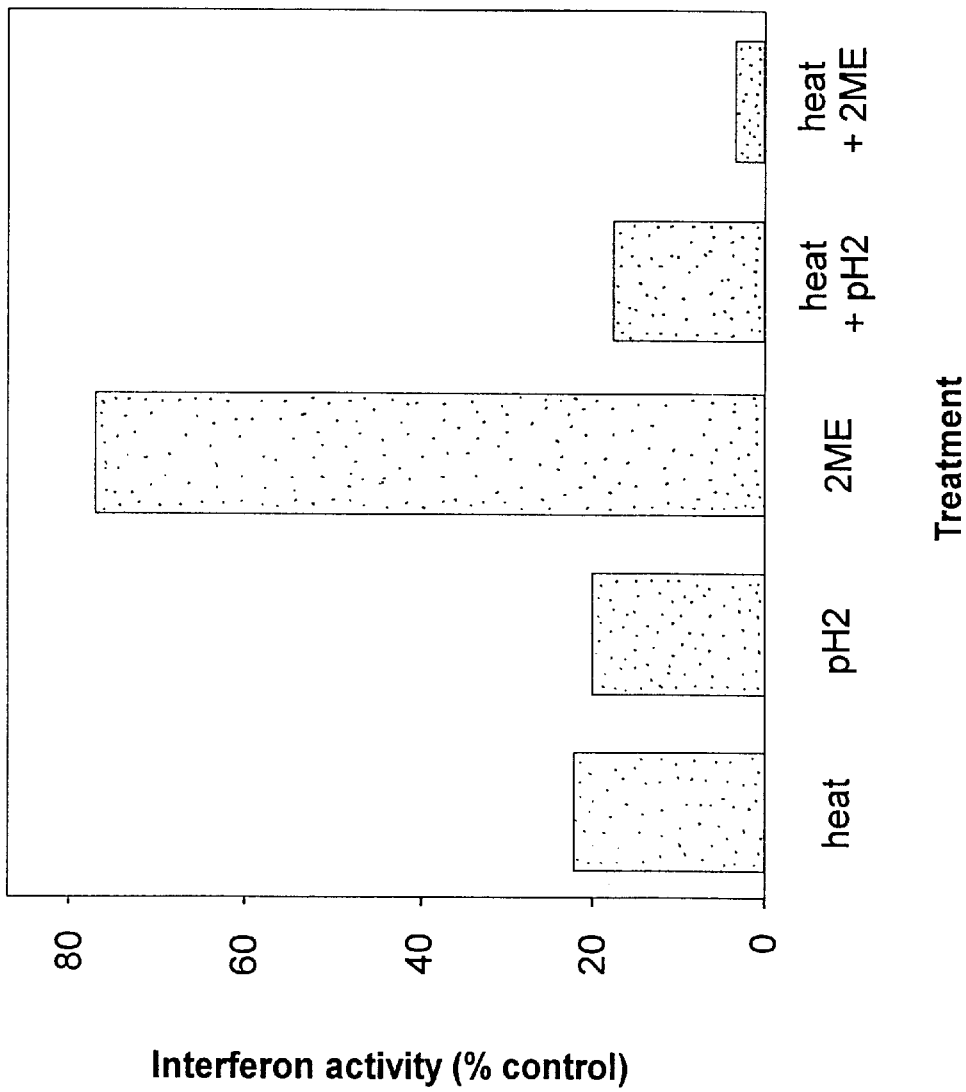

FIG. 5 is a graphical representation showing sensitivity of ChIFN-γ activity to heat, pH 2.0 and 2-mercaptoethanol (2-ME). Supernatants from the CC8.1h (AGAL Accession No. N94/46035) was heated to 60° C. for 1 hr, exposed to pH 2.0 for 8 hr or exposed to 0.5% 2-ME or the combinations of these conditions indicated. Residual activity was measured using the CEF assay.

Figure 6:
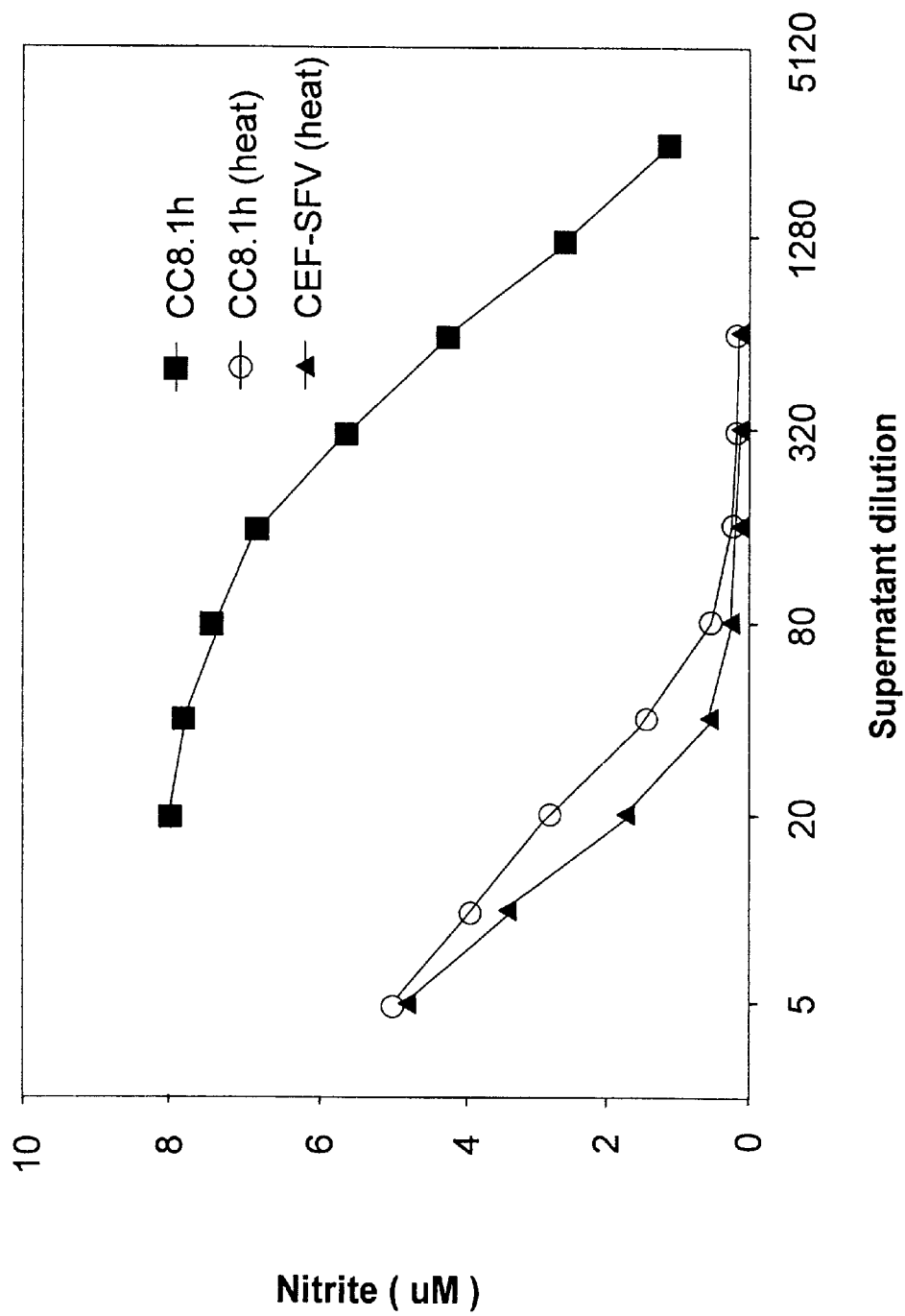

FIG. 6 is a graphical representation showing induction of nitrite secretion by HD11 macrophages induced by T cells expressing ChIFN-γ. Supernatants from native or heat-inactivated CC8.1h (AGAL Accession No. 94/46035) or SFV-induced CEFs were measured for their ability to induce nitrite secretion.

Figure 7:
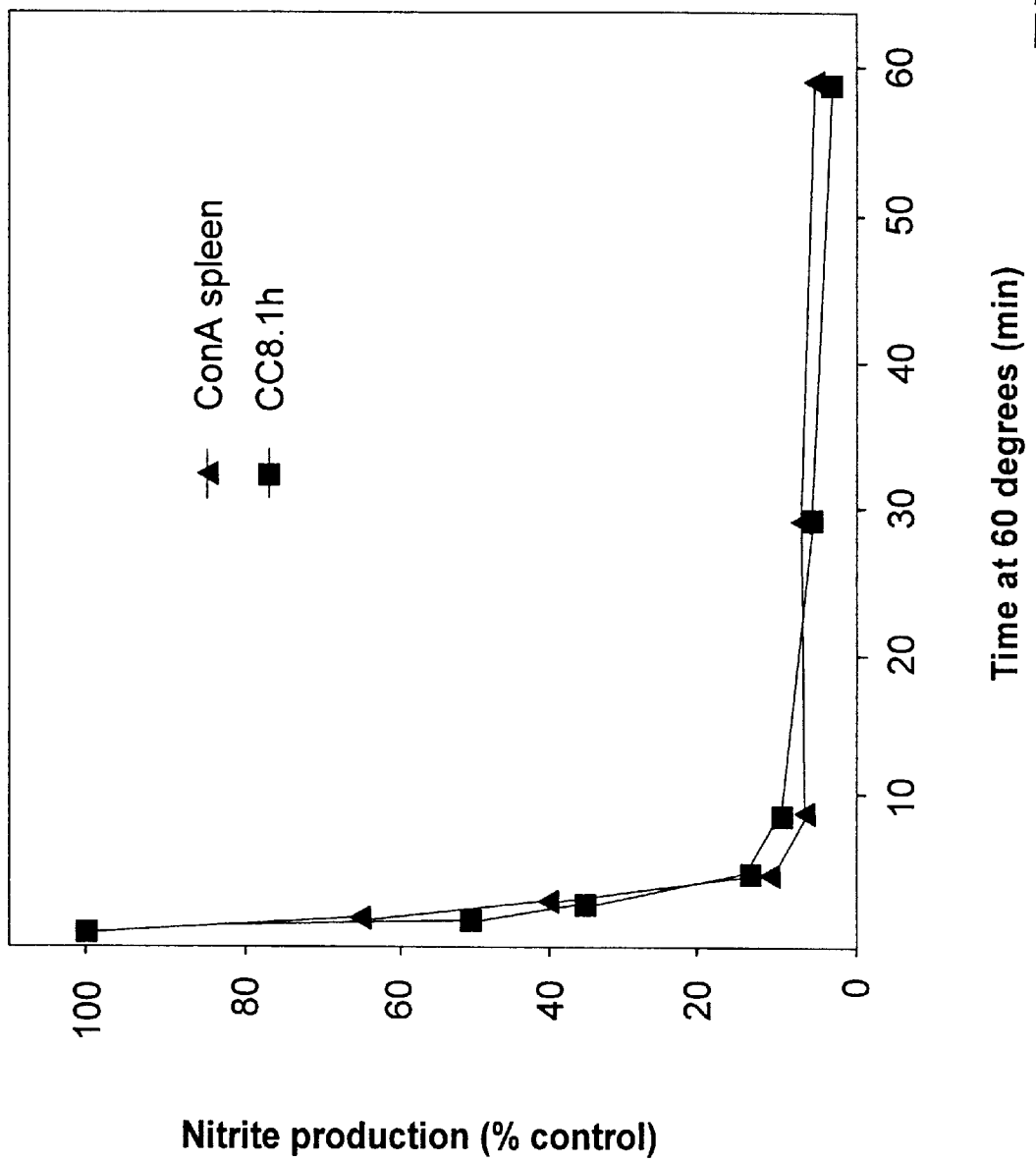

FIG. 7 is a graphical representation showing heat sensitivity of nitrite-inducing (ChIFN-γ) activity. Supernatants from CC8.1h (AGAL Accession No. N94/46035) and ConA activated spleen cells were heated to 60° C. and residual ChIFN-γ activity was measured using the nitrite assay as described in the Examples.

Figure 8A:
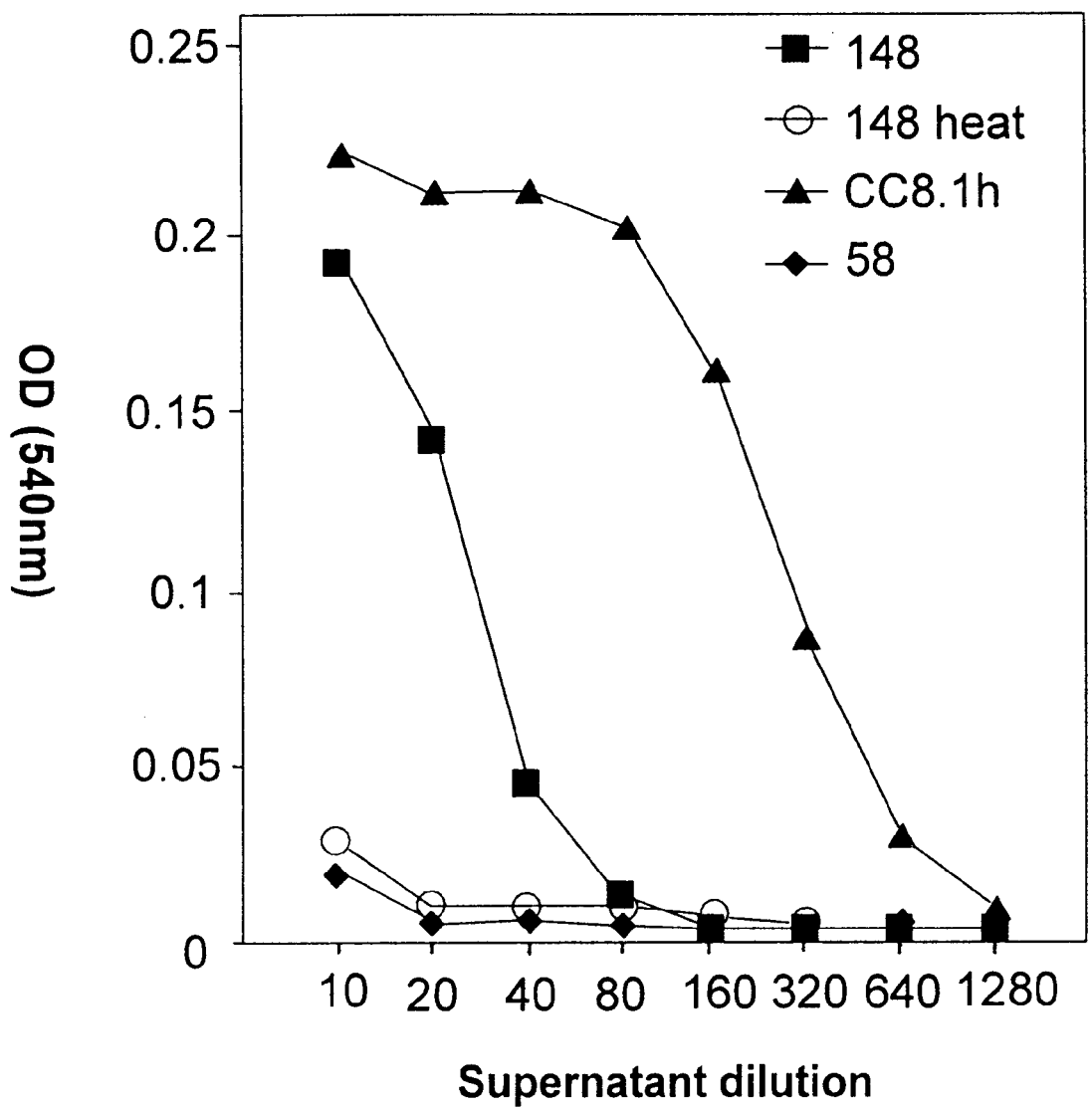
Figure 8B:
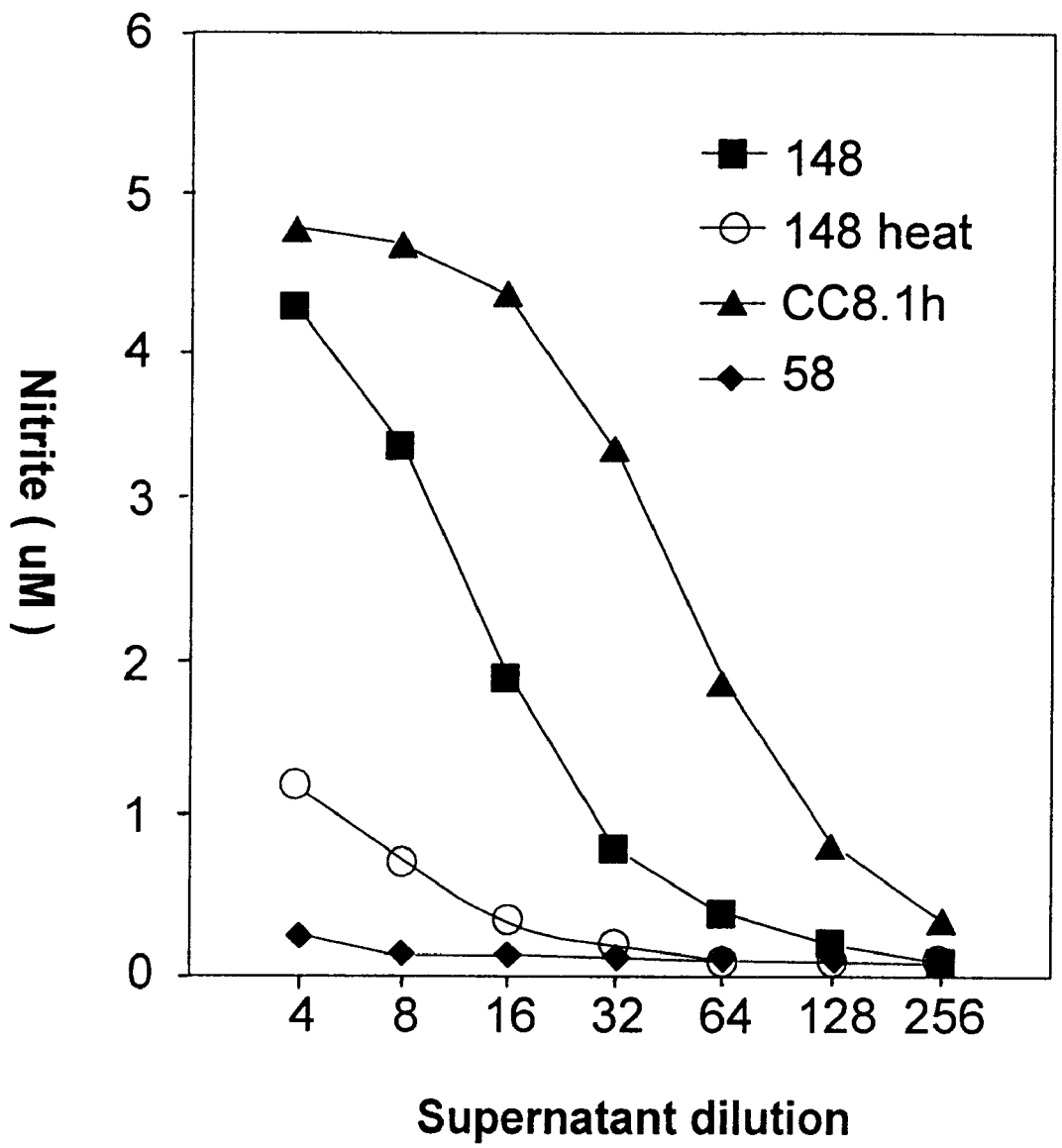

FIGS. 8A–B provide graphical representations showing biological activity of supernatants from transfected COS cells. COS cells were transfected with pools of approximately 100 clones from the CC8.1h cDNA expression library. ChIFN-γ was measured in the CEF assay (FIG. 8A) or the nitrite assay (FIG. 8B) as described in the Examples. Supernatant from COS cells expressing the ChIFN-γ gene was heated at 60° C. for 30 min (148 heat) or not heated (148). Supernatant from CC8.1h was used as a positive control and supernatant from COS cells transfected with a pool lacking the ChIFN-γ gene (58) was used as a negative control.

Figure 9:
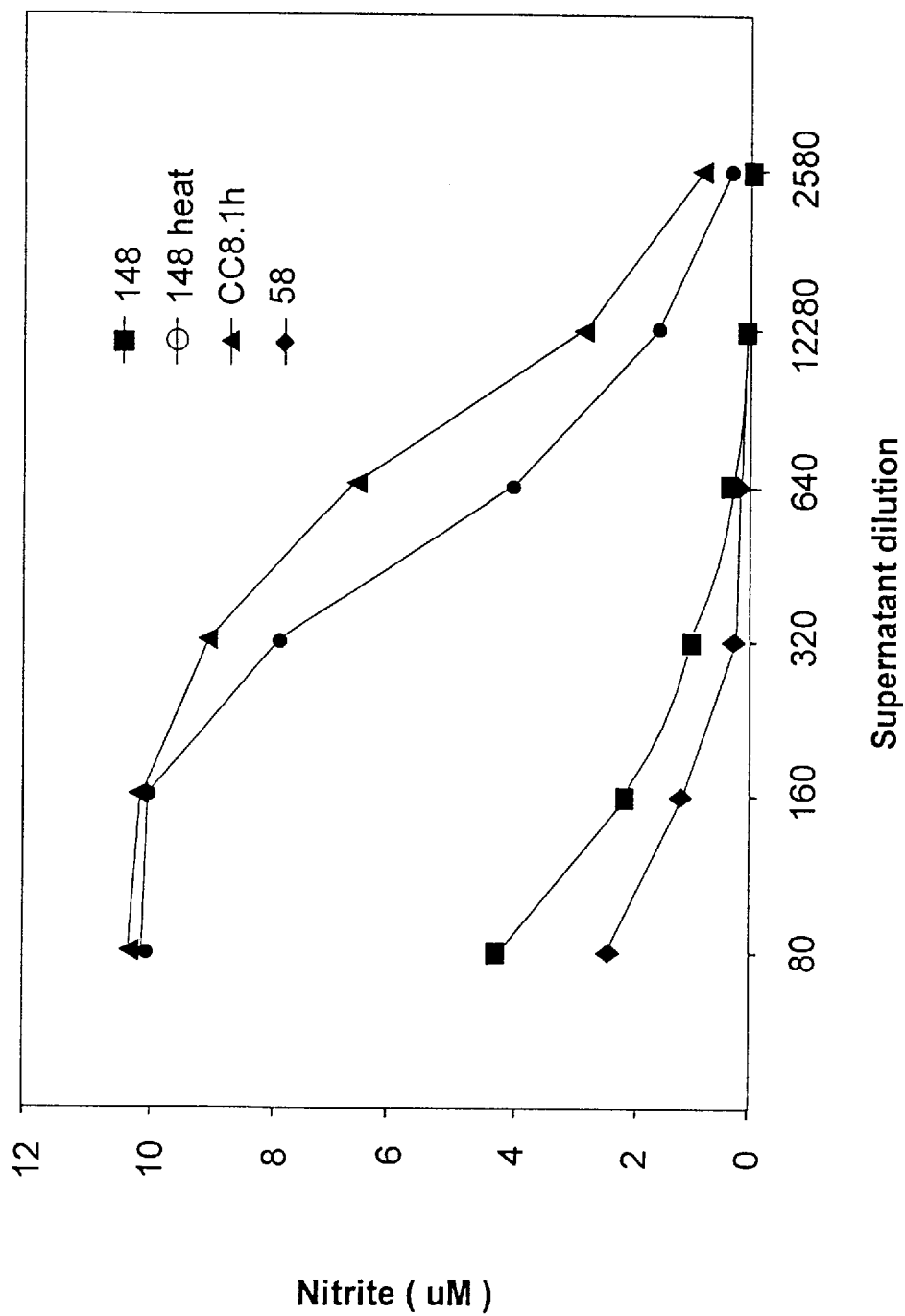

FIG. 9 is a graphical representation showing biological activity of supernatants from COS cells transfected with single clones of the CC8.1h library. Plasmid pools containing 100 clones were sequentially subpooled into pools of 10 and then into single clones. Clones 148.1.7 and 148.1.9 were transfected into COS cells and ChIFN-γ activity was measured in the supernatant 3 days later. The effect of heating the recombinant ChIFN-γ to 60° C. for 30 min is shown.

Figure 10:
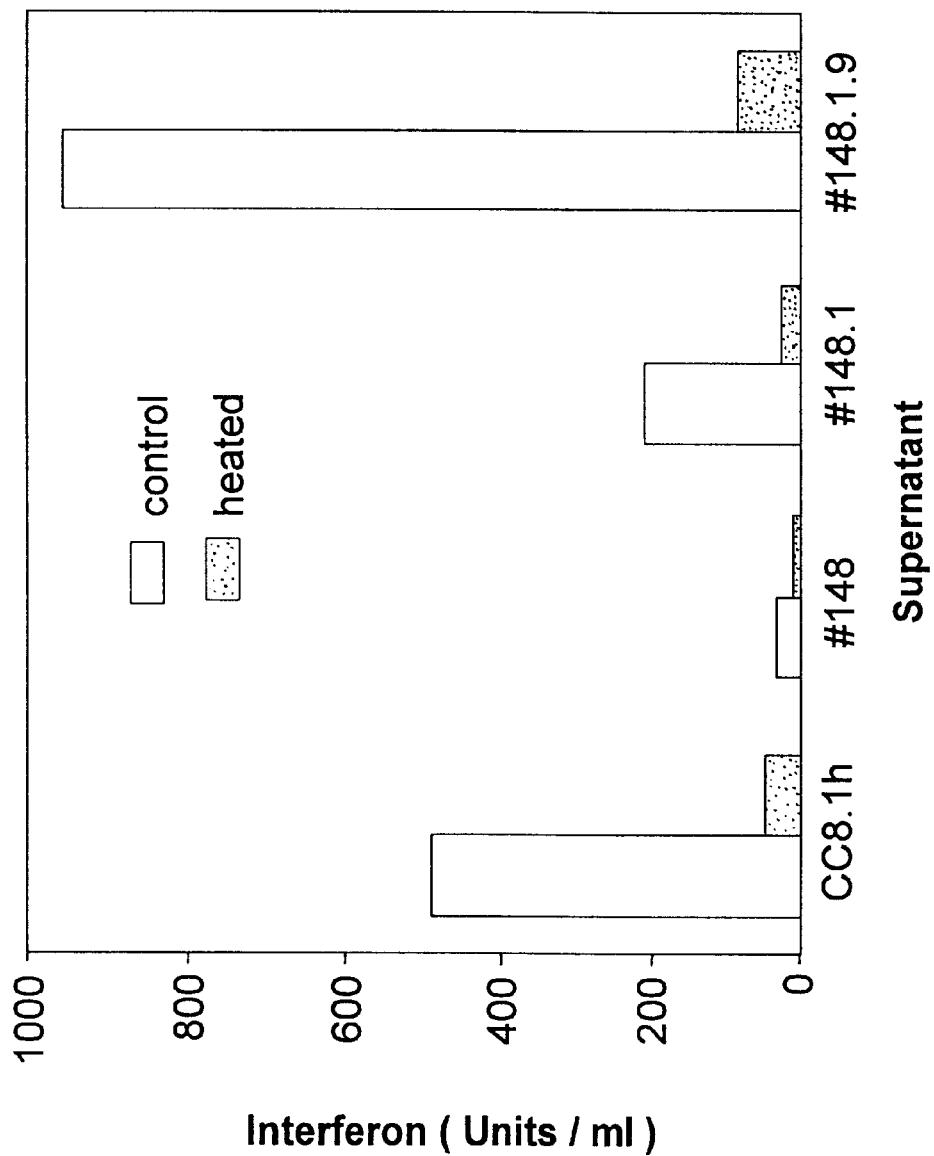

FIG. 10 is a graphical representation showing production of recombinant ChIFN-γ. COS cells were transfected with #148 (pool of 100 clones), #148.1 (a pool of 10 clones derived from 148) and #148.1.9 (a single clone derived from 148.1). Supernatant from CC8.1h (AGAL Accession No. N94/46035) is used as a positive control. The effect of heating the supernatants to 60° C. for 30 min is also shown.

Figure 11:
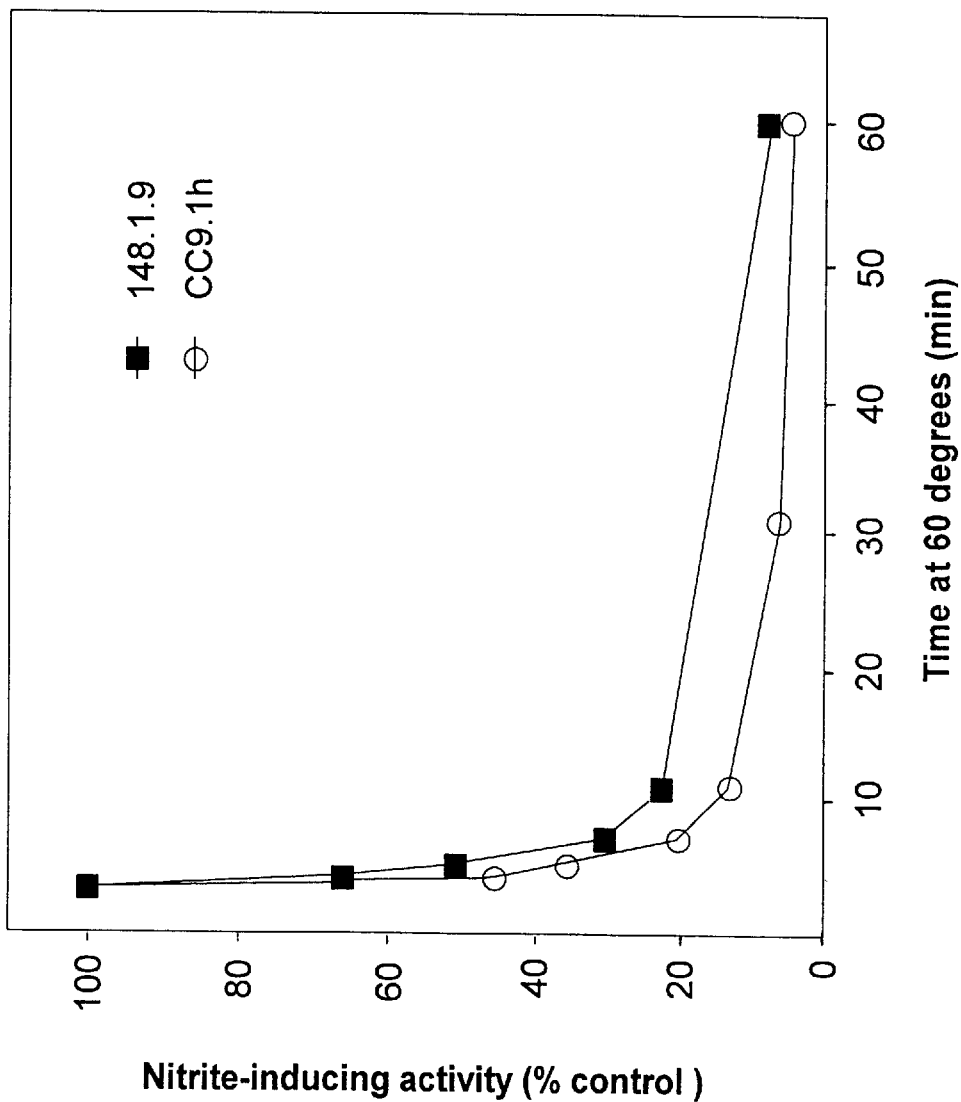

FIG. 11 is a graphical representation showing heat sensitivity of ChIFN-γ. Supernatant from CC8.1h (AGAL Accession No. N94/46035) or clone 148.1.9 was heated to 60° C. for various periods of time and residual ChIFN-γ activity was measured in the nitrite assay.

FIGS. 12a and 12b, when lined up to the match line, depict the nucleotide sequence of the ChIFN-γ cDNA with the predicted 164 amino acid sequence of the ChIFN-γ polypeptide shown. Two potential N-linked glycosylation sites are underlined. The predicted cleavage site for the mature protein is indicated by the arrow at HIS 1.

FIGS. 13a and 13b, when lined up to the match line, show the amino acid sequence homology between the ChIFN-γ polypeptide (avian) and various mammalian IFN-γ proteins. Amino acids conserved in all species are highlighted by asterisks and conservative substitutions by dots.

FIG. 14 is a diagrammatic representation showing amino acid sequence homology between human and avian IFN-γ polypeptides.

FIG. 15 is a diagrammatic representation showing a comparison of ChIFN-α (Sekellick et al, 1994) and ChIFN-γ protein sequences.

Figure 16:
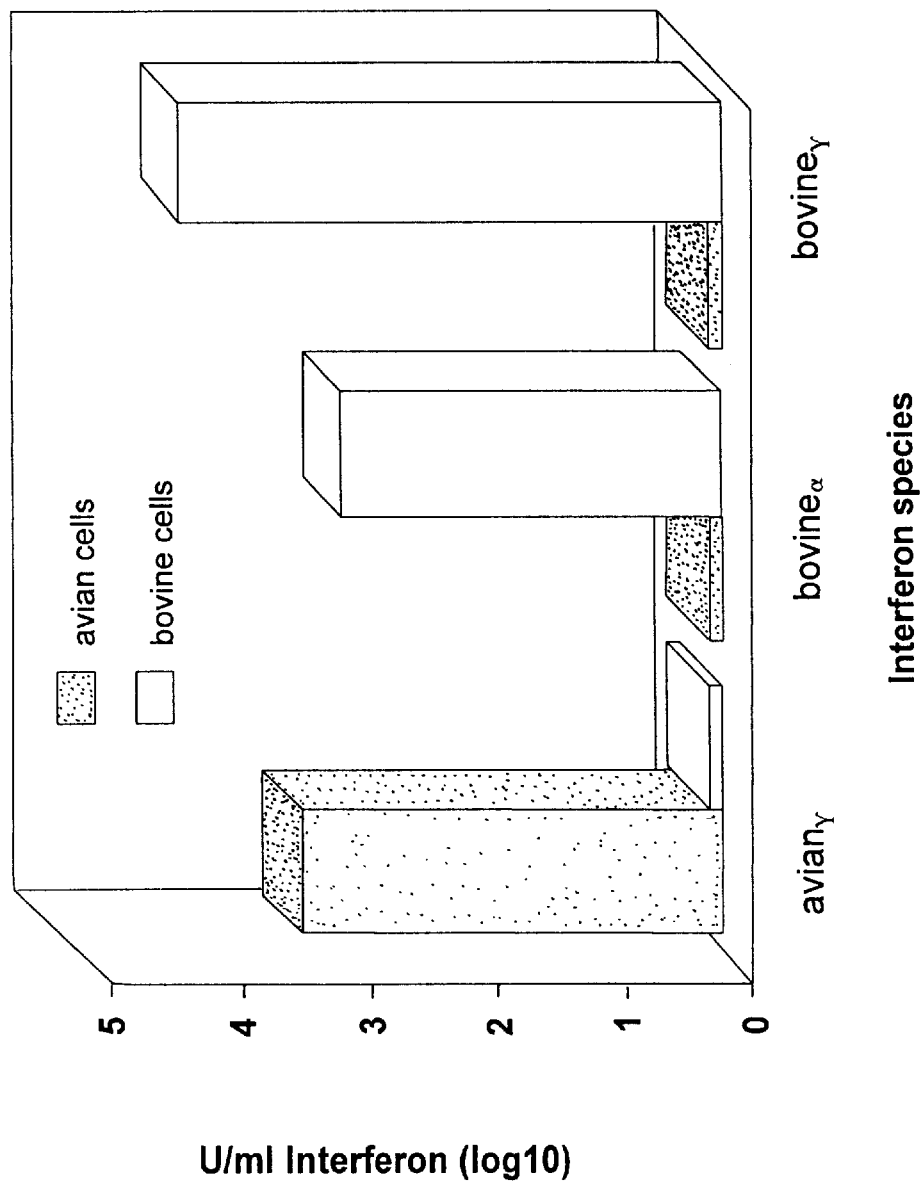

FIG. 16 is a graphical representation showing cross-species biological activity of ChIFN-γ, bovine IFN-α and bovine IFNγ. Recombinant chicken and bovine IFNs were assayed for their ability to protect chicken and bovine fibroblasts from virus mediated lysis.

Figure 17B:
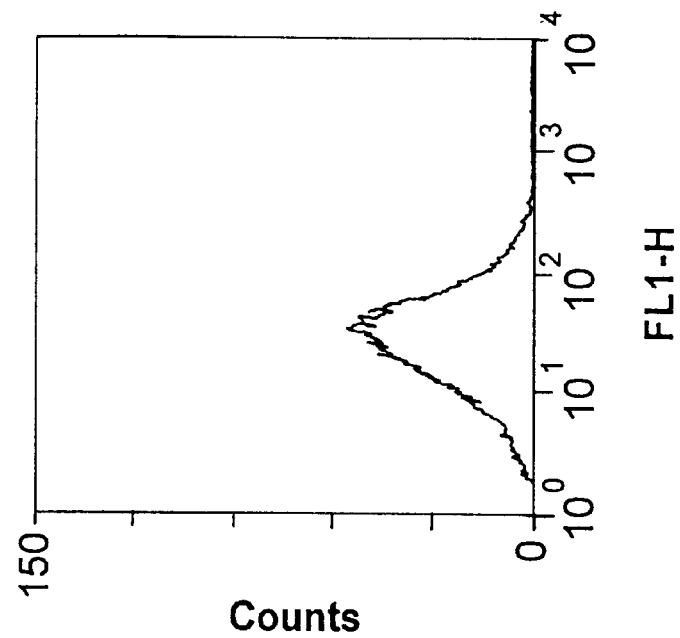
Figure 17A:
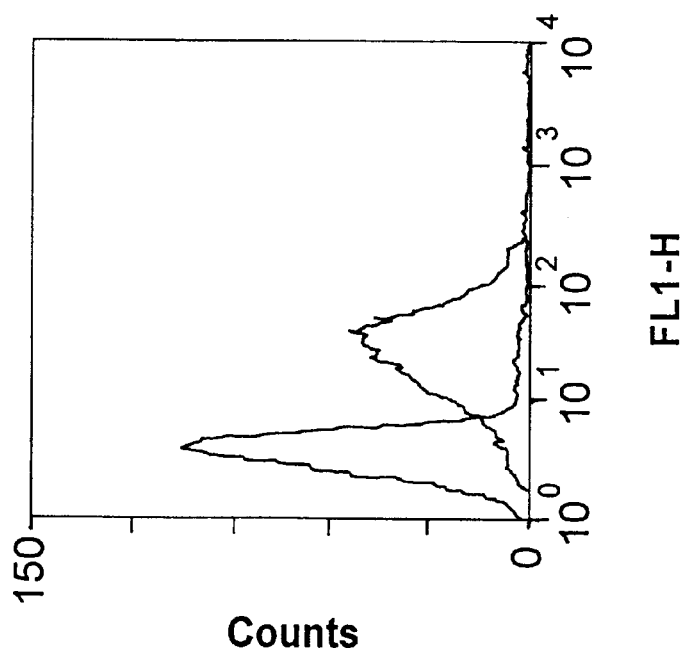
Figures 17C, 17D:
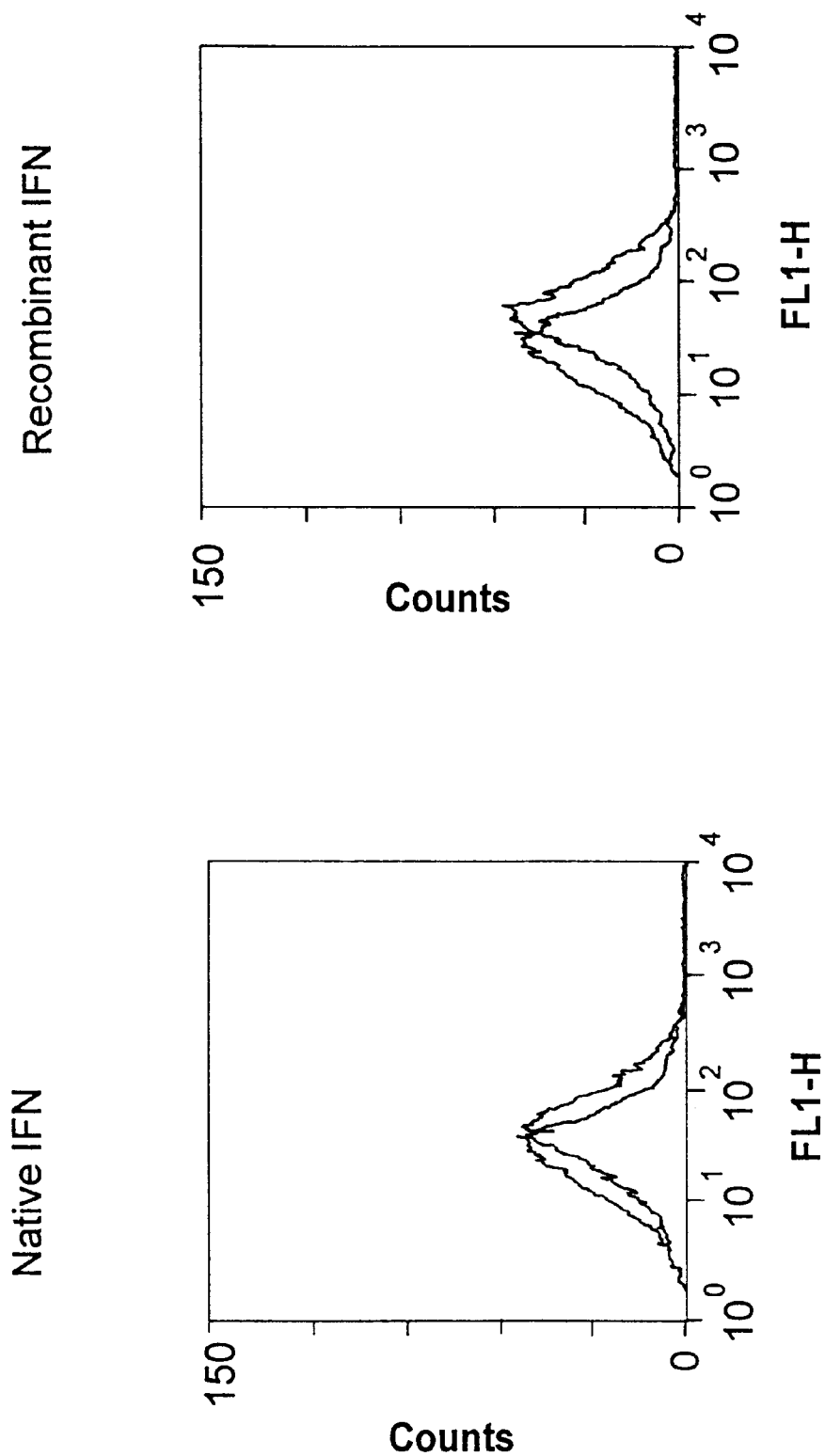

FIGS. 17A–D provide graphical representations of FACS profiles showing the expression of Class II antigen by HD11 cells. Cells were cultured in media alone (FIG. 17A), LPS (FIG. 17B), native ChIFN-γ (supernatant from CC8.1h; FIG. 17C) and recombinant ChIFN-γ_(FIG. 17D) and then measured for cell surface expression of Class II molecules.

Figure 18A:
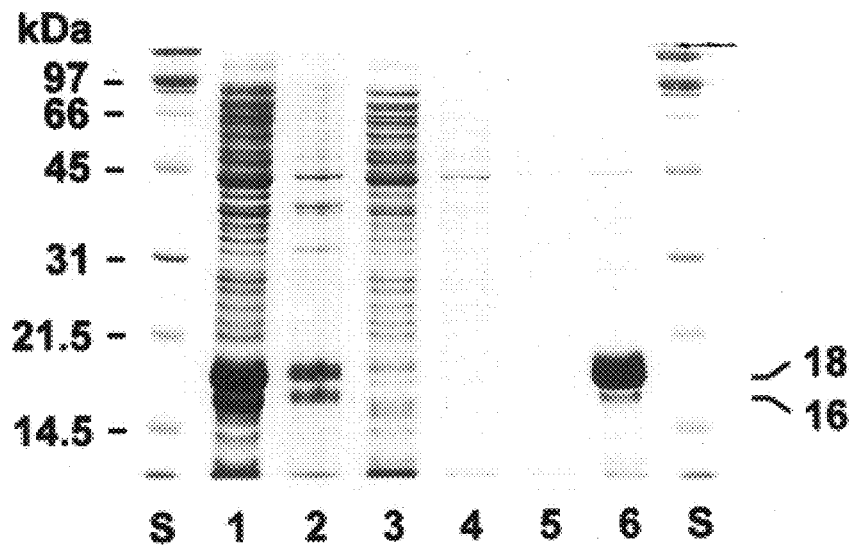
Figure 18B:
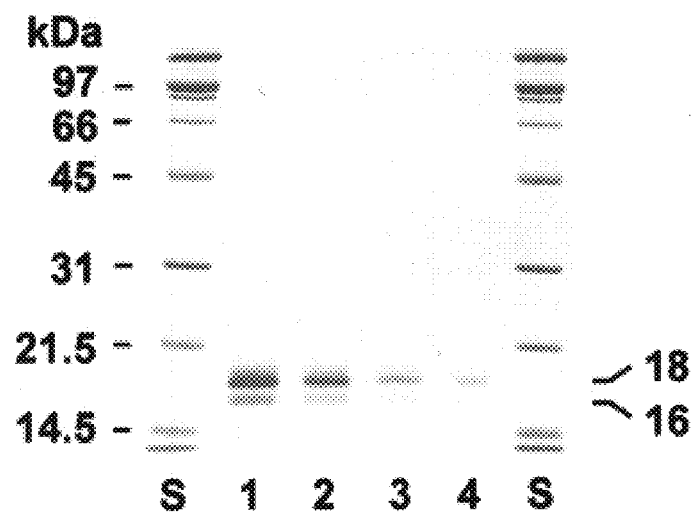

FIGS. 18A–B provide diagrammatic representations of polyacrylamide gels showing expression of recombinant ChIFN-γ in E. coli and subsequent purification. In FIG. 18A: S, standard Mr markers; Lane 1, crude sonication supernatant; Lane 2, soluble fraction; Lane 3, Ni column flow through; Lane 4 and 5, column washes; Lane 6, eluted recombinant ChIFN-γ. In FIG. 18B: S, standard Mr markers; Lanes 1–4, purified recombinant ChIFN-γ serially diluted 2-fold (lane 1), 4-fold (lane 2), 8-fold (lane 3) or 16-fold (lane 4).

Figure 19A:
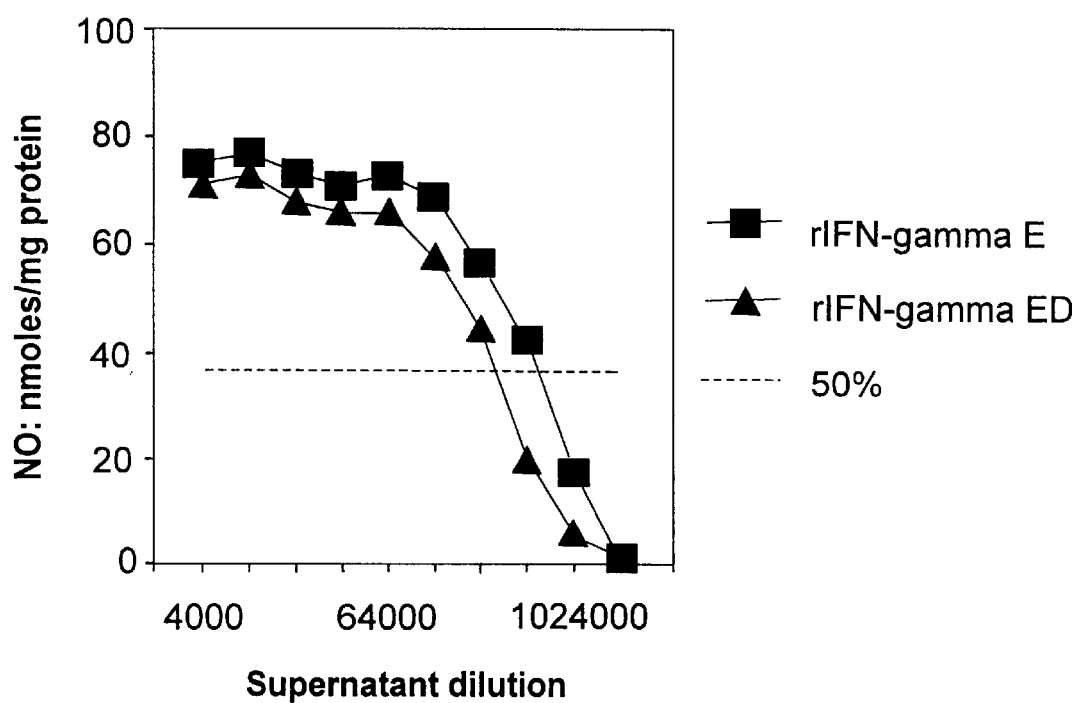
Figure 19B:
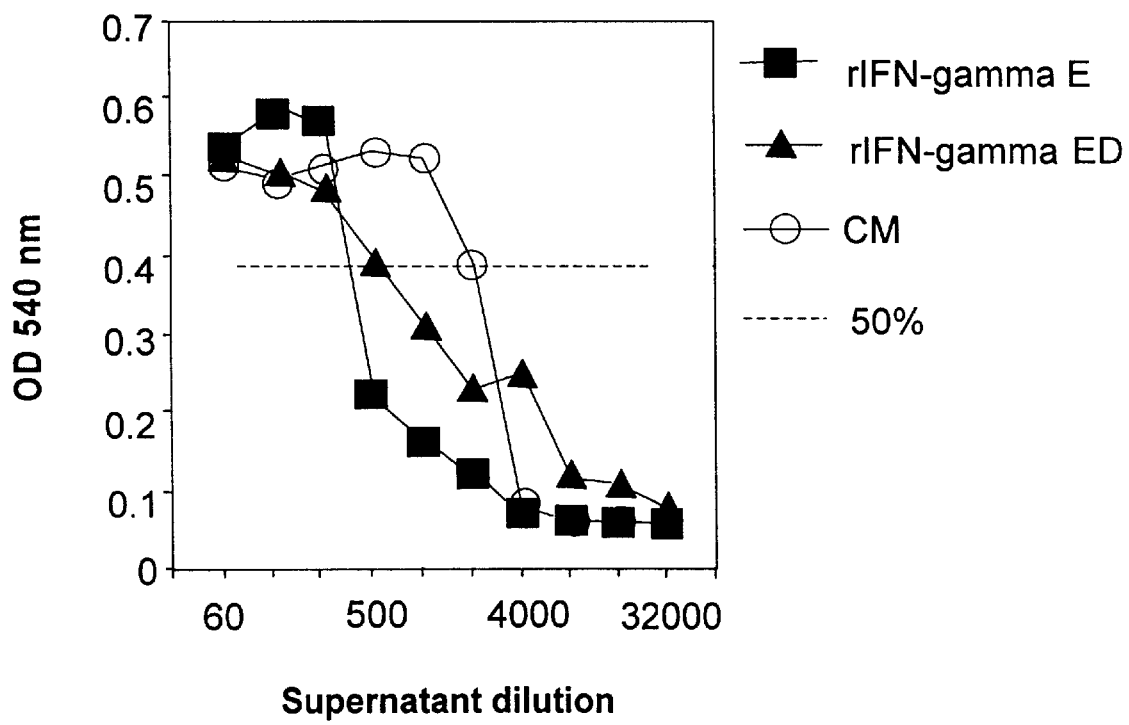
Figure 19C:
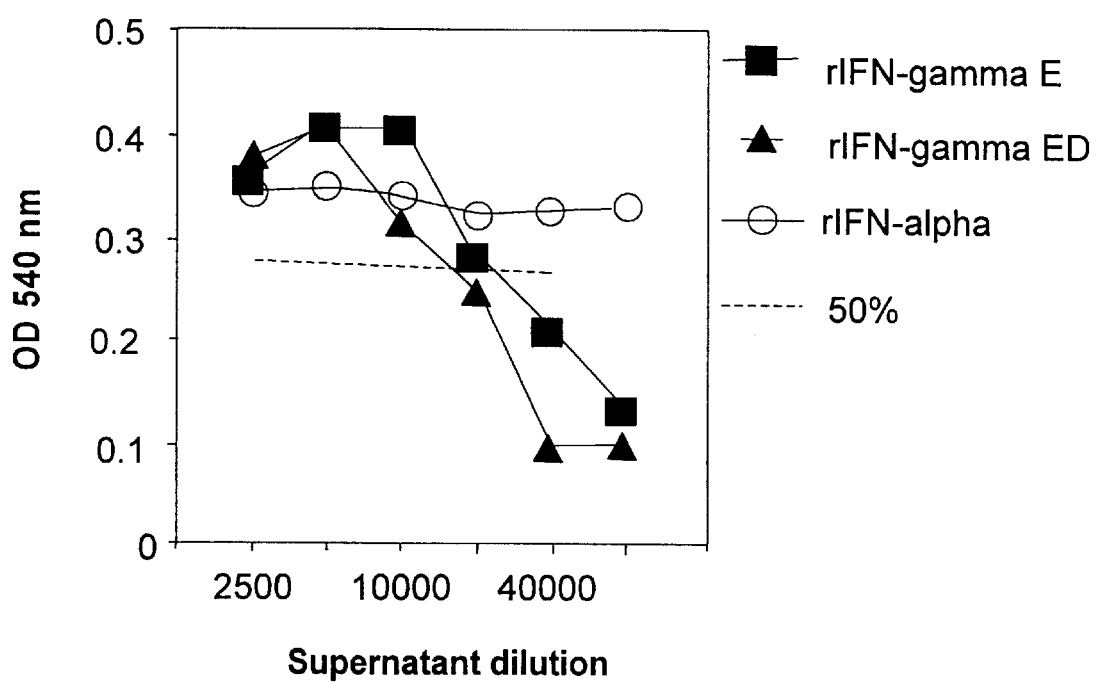

FIGS. 19A–C provide graphical representations showing biological activity of recombinant ChIFN-γ on chicken (CEF) and turkey cells (TEF). In FIG. 19A the capacity of purified recombinant ChIFN-γ (ED: dialyzed to remove imidazole; E: non-dialyzed), to induce nitrite secretion by HD11 chicken macrophages is shown. In FIG. 19B; the capacity of purified recombinant ChIFN-γ (ED: dialyzed; E: non-dialyzed) and chicken spleen cell conditioned media (CM) to protect CEFs from virus mediated lysis is shown. In FIG. 19C, the capacity of purified recombinant ChIFN-γ (ED: dialyzed; E: non-dialyzed) and recombinant ChIFN-α to protect TEFs from virus mediated lysis is shown.

Figure 20:
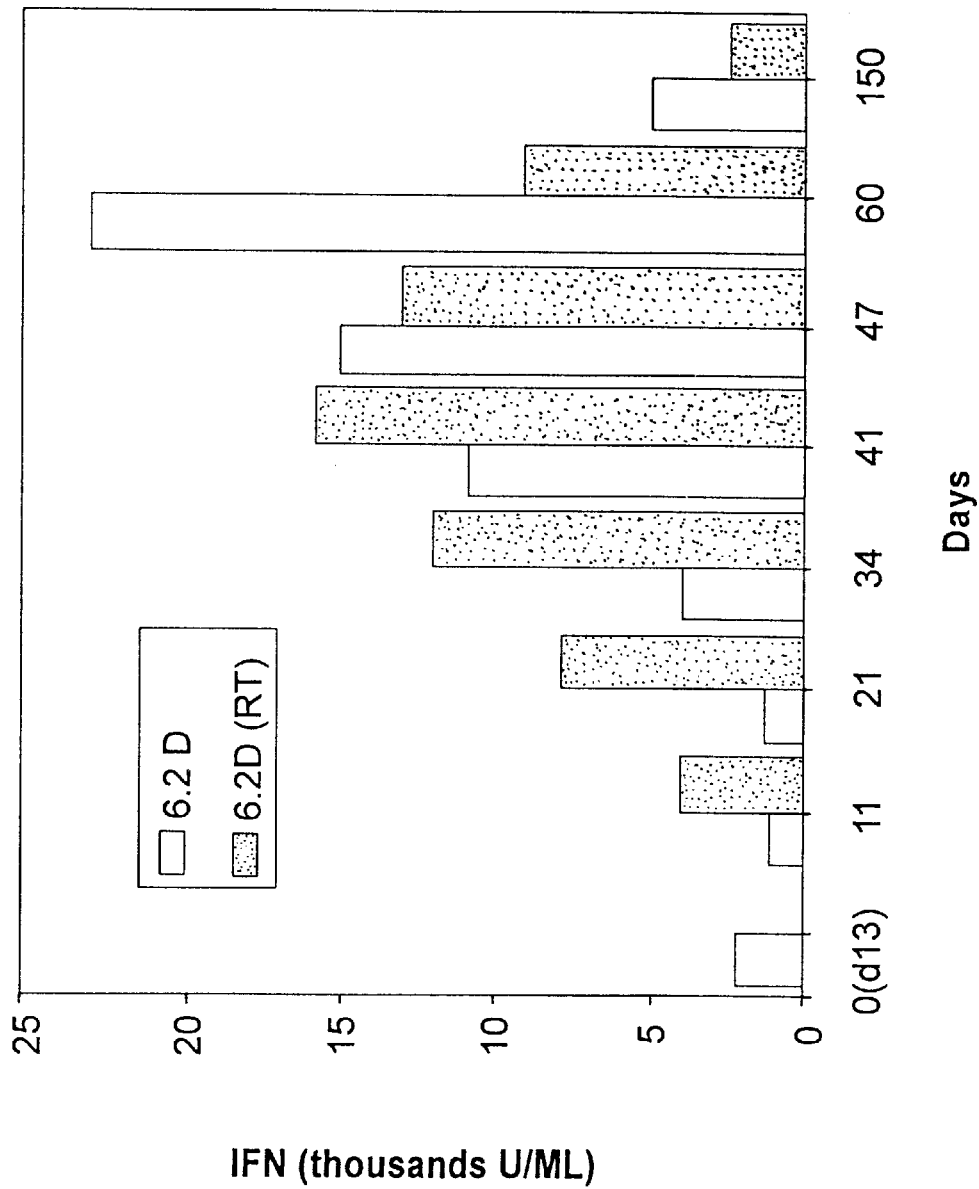

FIG. 20 is a graphical representation showing stability of recombinant ChIFN-γ following storage at room temperature [6.2D (RT)] or at 4° C. (6.2D) as measured using the nitrite assay.

Figure 21A:
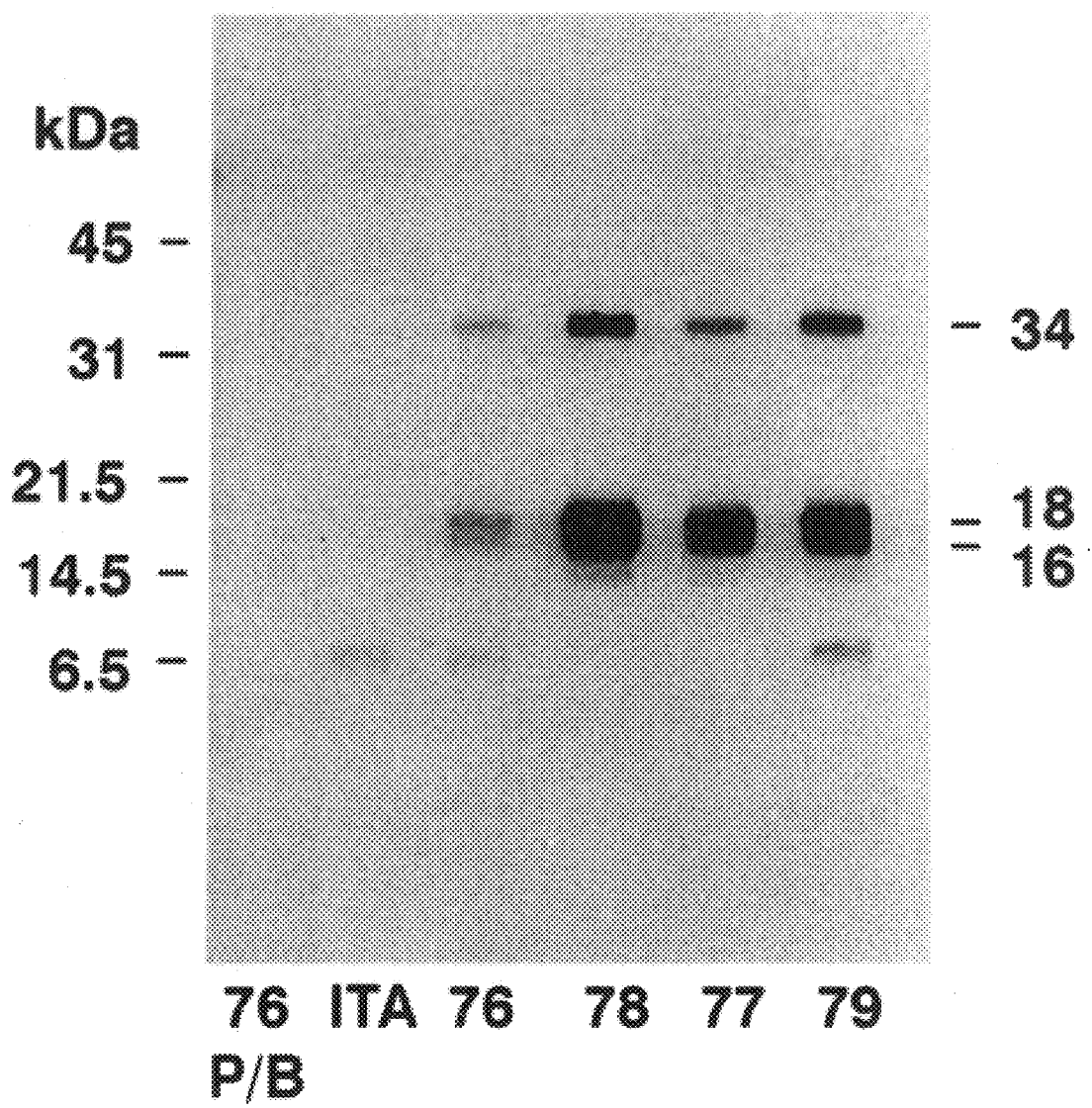
Figure 21B:
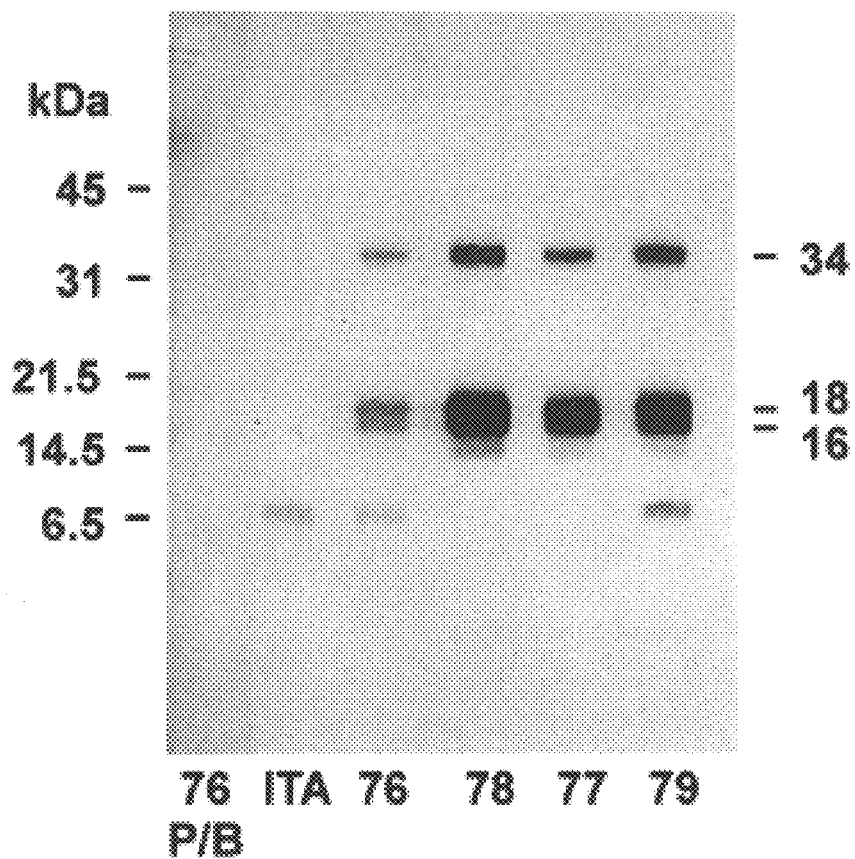

FIG. 21 is a diagrammatic representation of a Western Blot showing binding of rabbit anti-ChIFN-γ sera to recombinant ChIFN-γ. Recombinant ChIFN-γ was electrophoresed on an acrylamide gel, blotted onto nitrocellulose which was then cut into strips Individual strips were incubated in sera; (76 P/B, normal rabbit serum; ITA, serum raised against an irrelevant antigen; 76.79 sera from 4 rabbits immunized with recombinant ChIFN-γ).

Figure 22A:
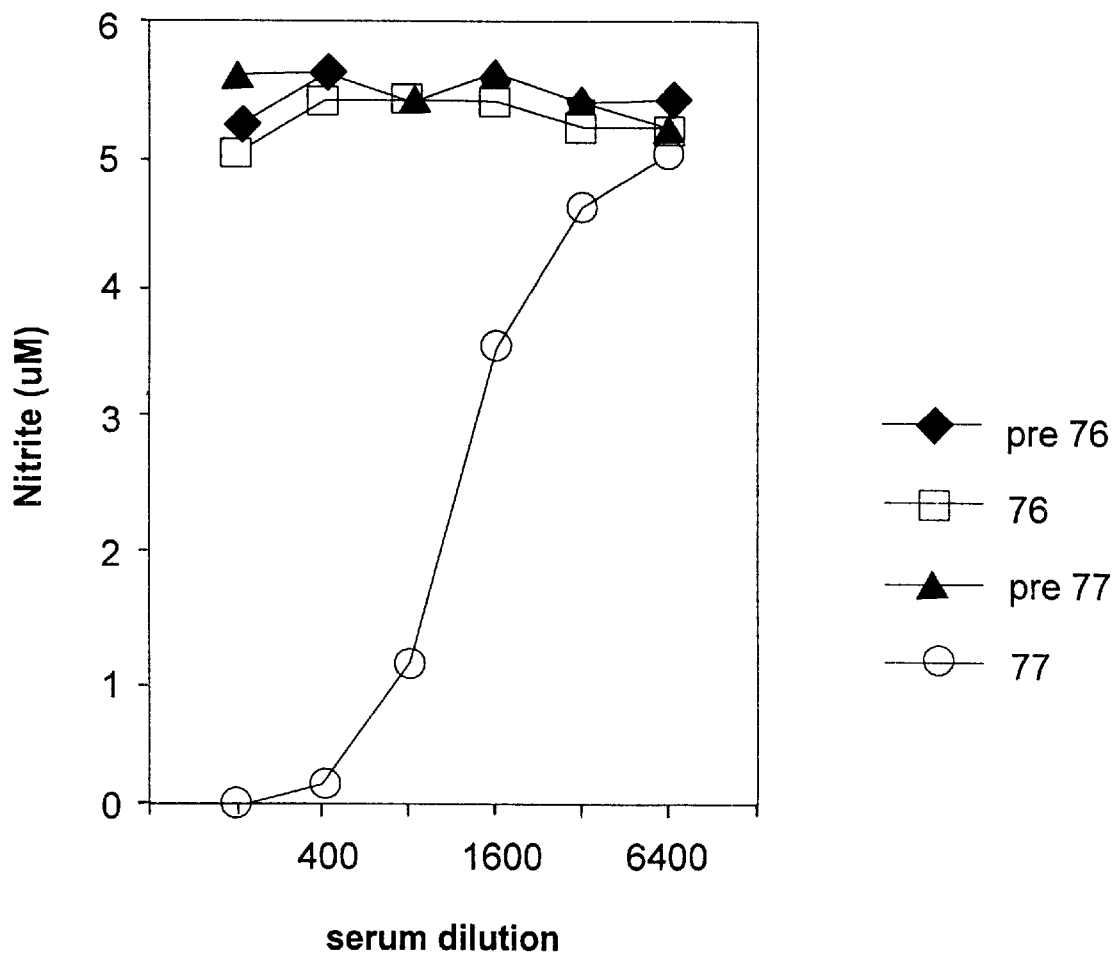
Figure 22B:
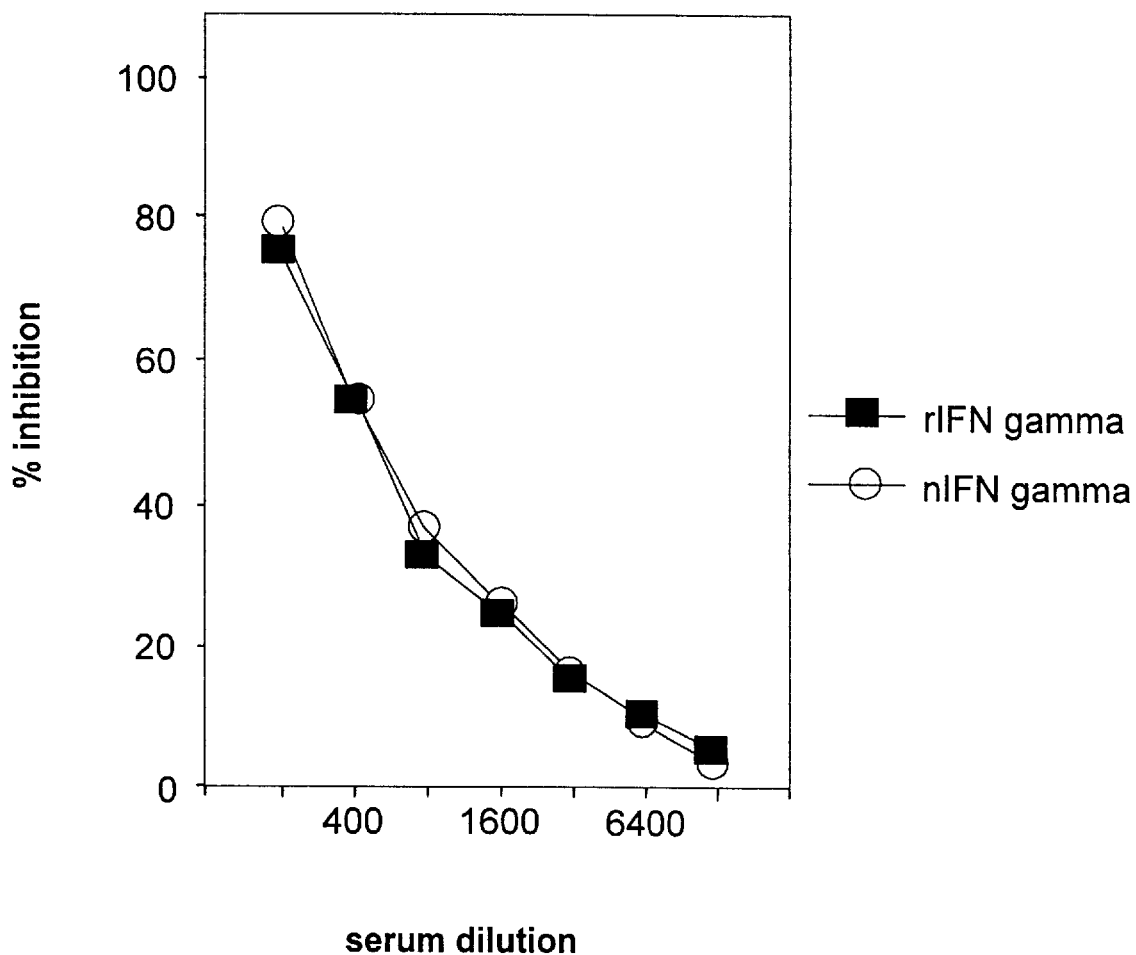
Figure 22C:
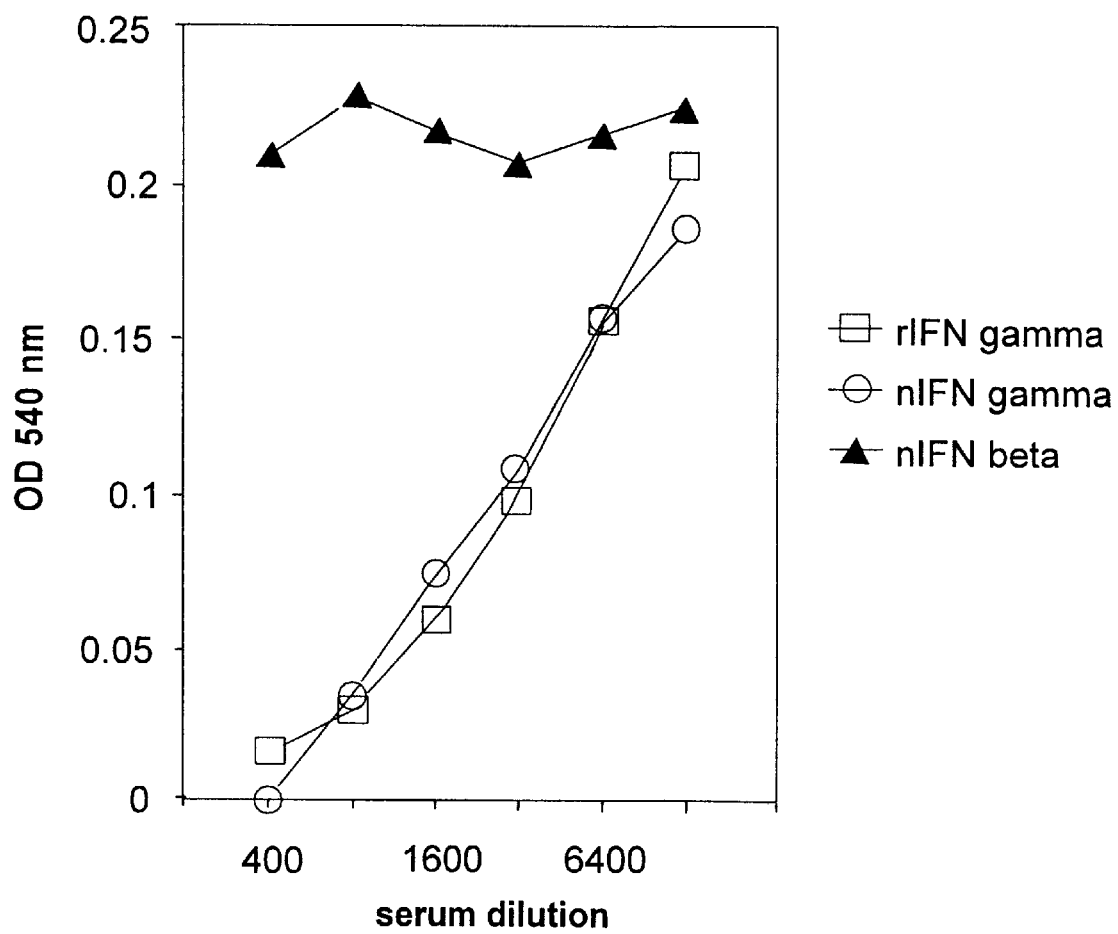

FIGS. 22A–C provide graphical representations showing the ability of rabbit anti-recombinant ChIFN-γ antisera to block the function of both recombinant (r) and native (n) ChIFN-γ as measured using either the nitrite assay FIGS. 22A, 22B) or using the CEF assay (FIG. 22C).

Figure 23B:
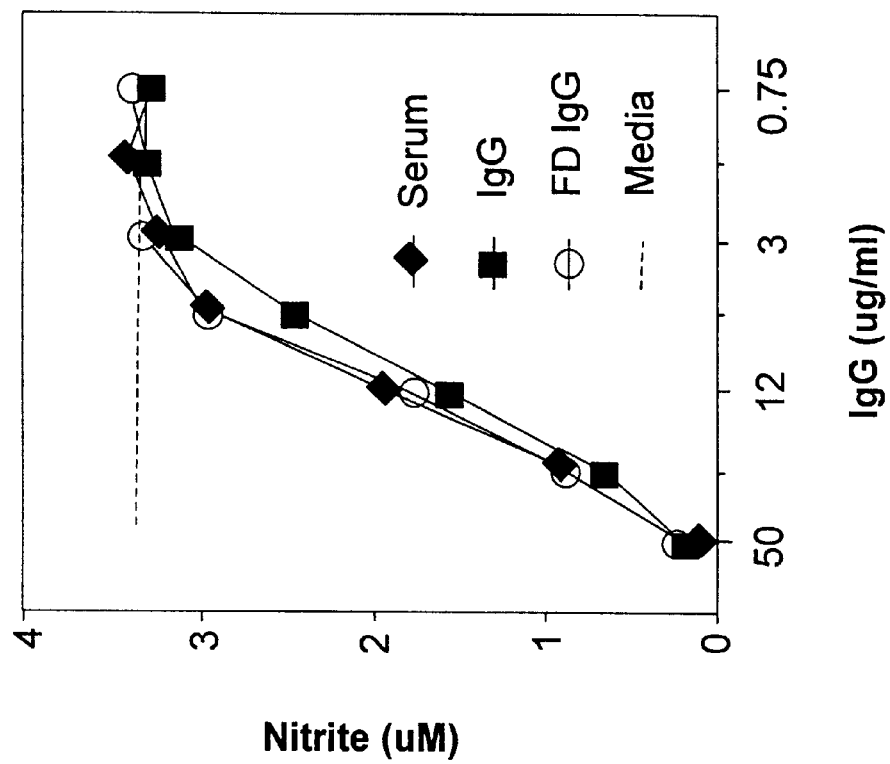
Figure 23A:
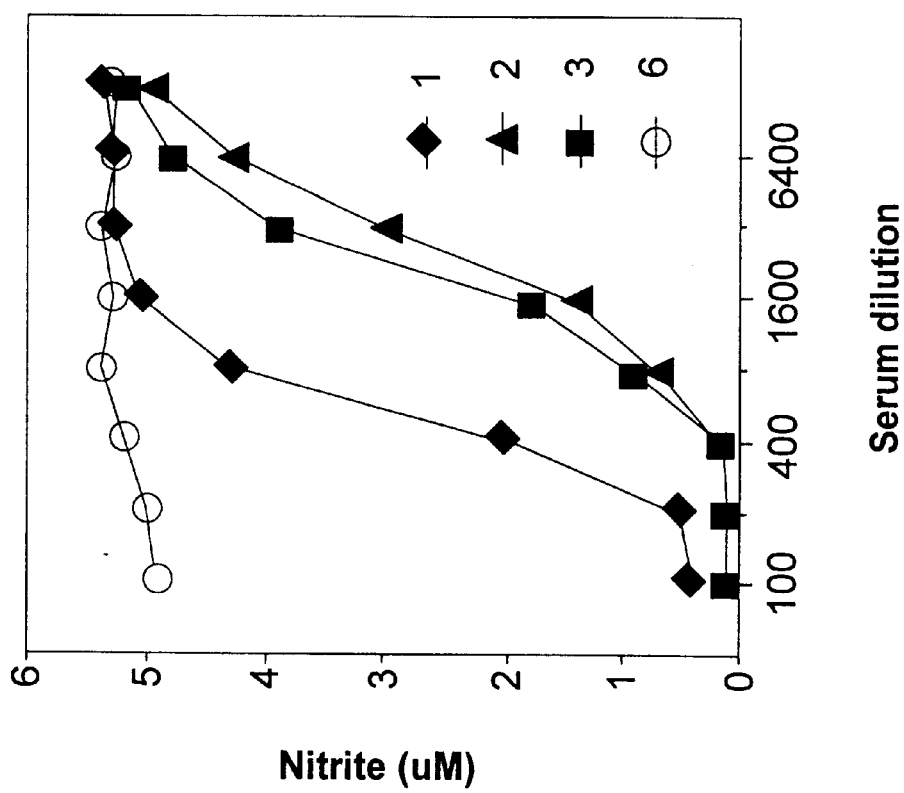

FIGS. 23A–B provide graphical representations showing the ability of mouse anti-recombinant ChIFN-γ antisera (FIG. 23A) and purified rabbit anti-recombinant ChIFN-γ IgG (FIG. 23B) to block the function of native ChIFN-γ in the nitrite assay.

Figure 24A:
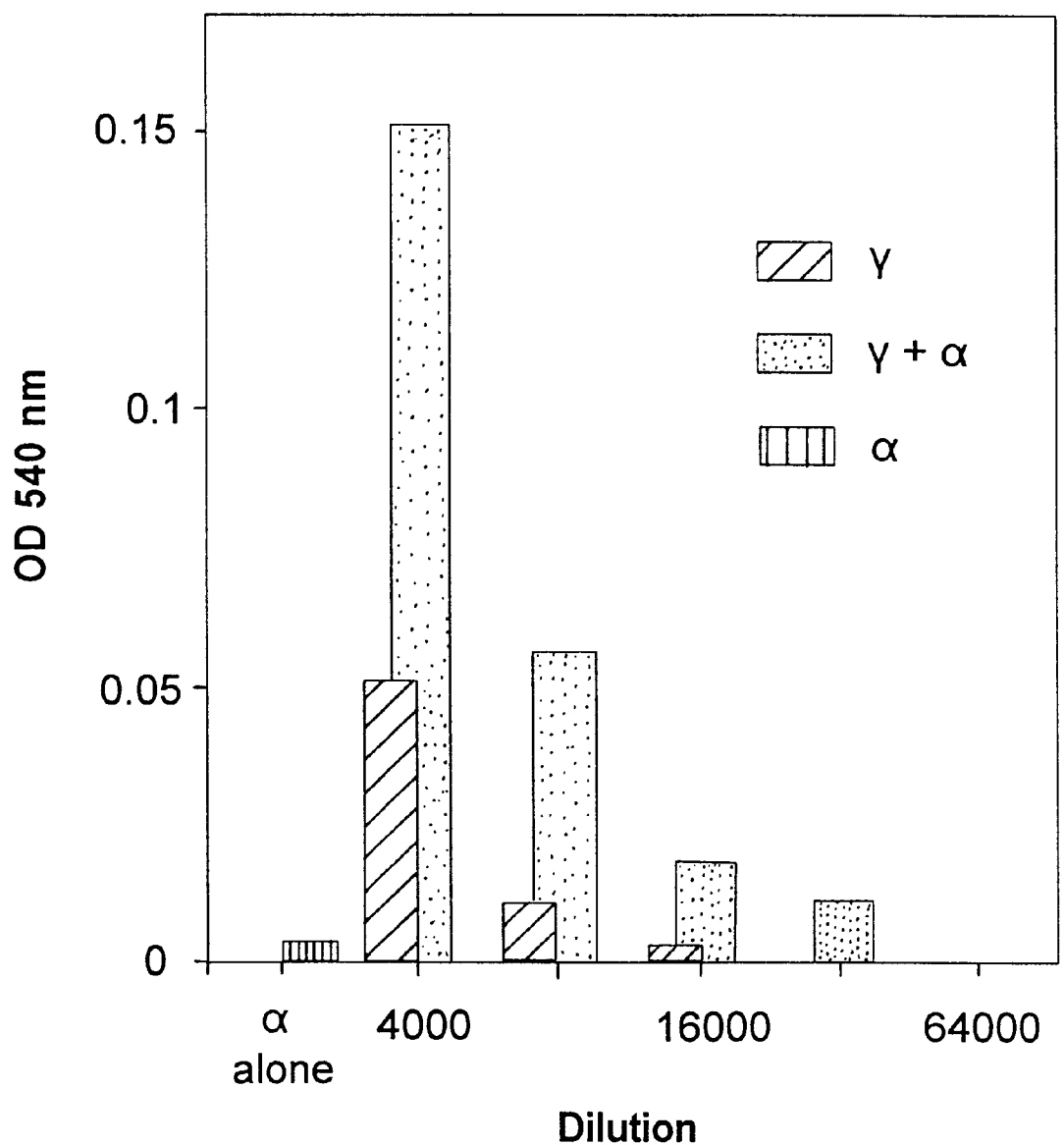
Figure 24B:
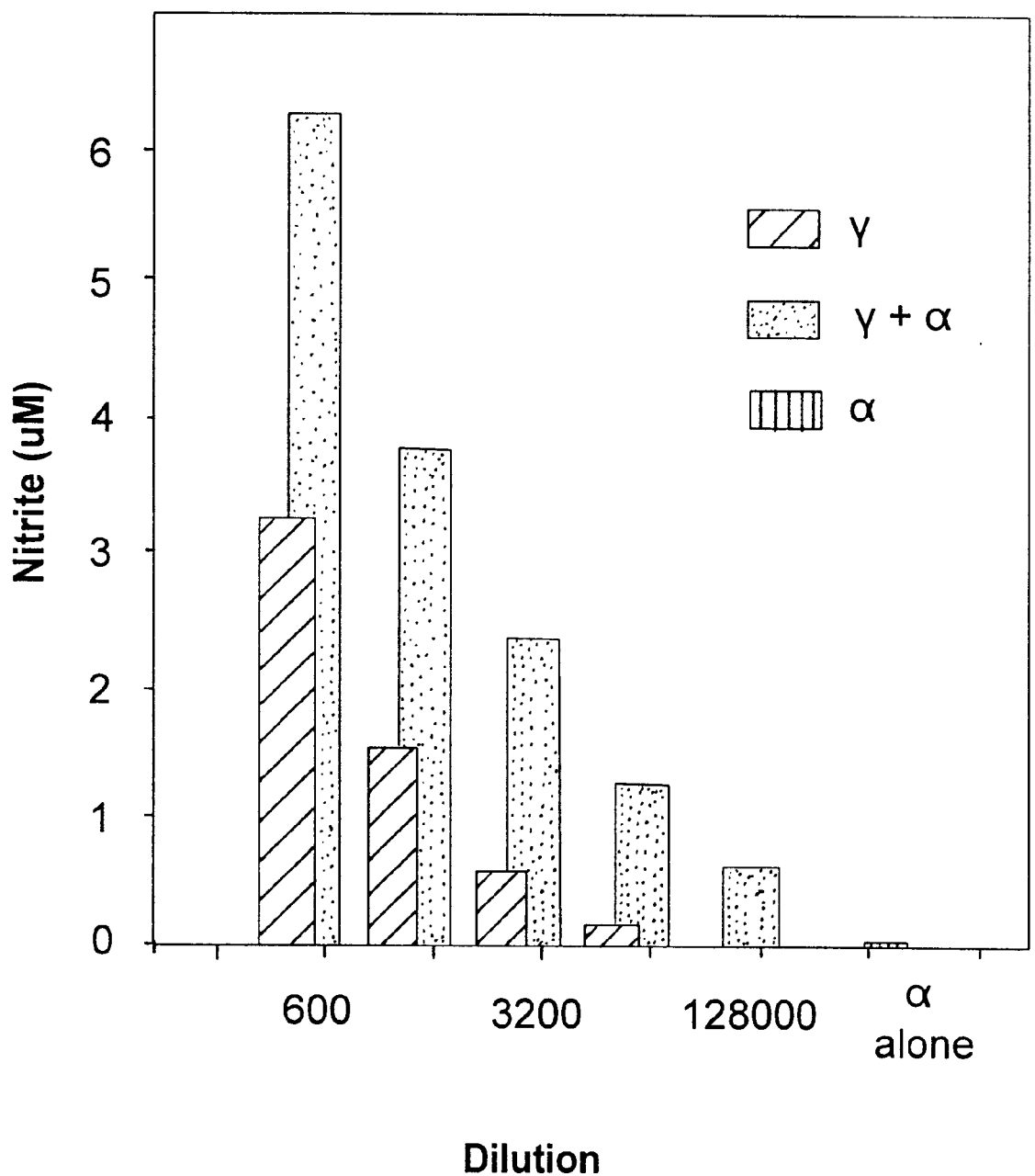
Figure 24C:
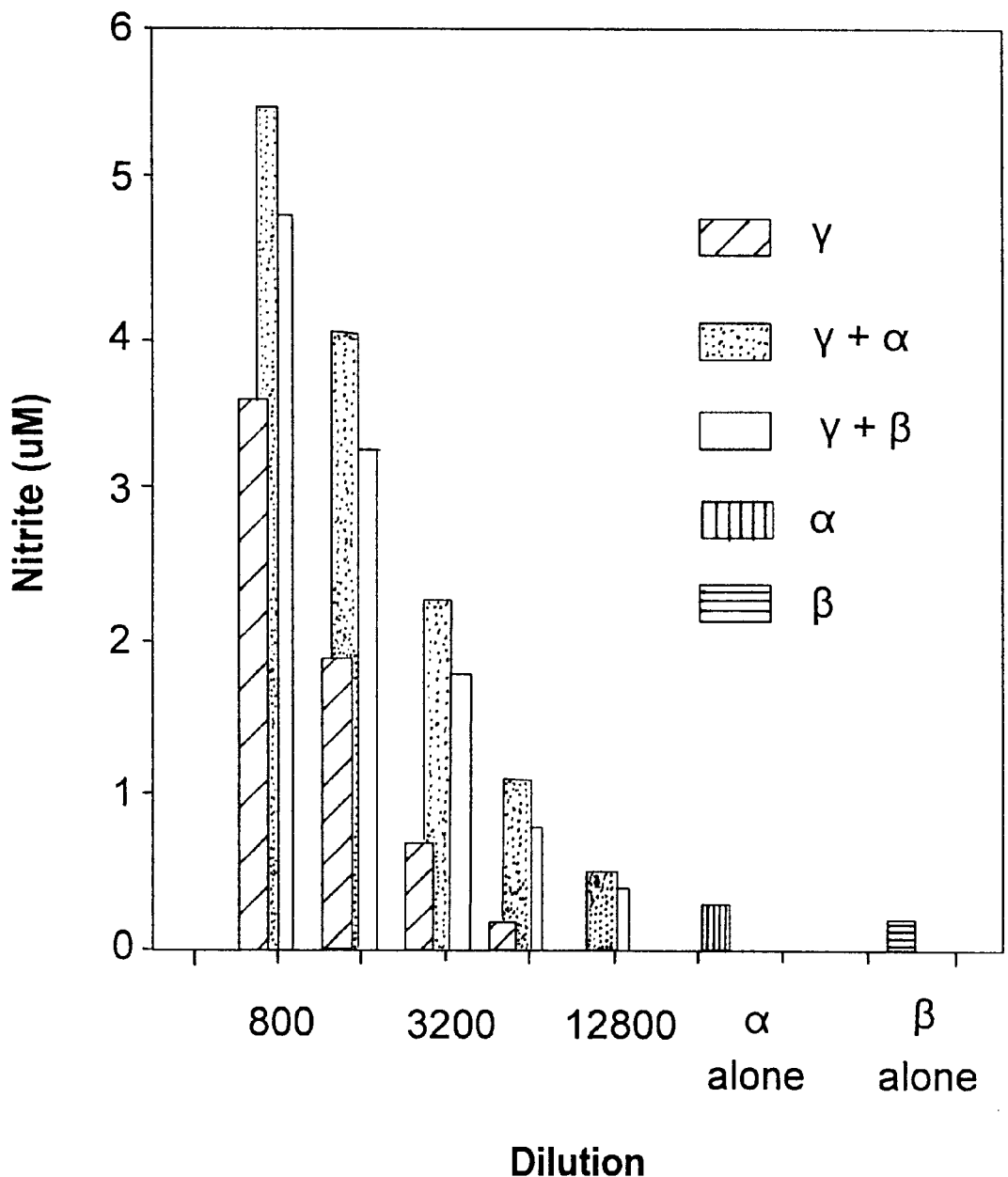

FIGS. 24A–C provide graphical representations showing the ability of ChIFN-γ and ChIFN-α to synergise. In FIG. 24A, the IFN activity is determined using the CEF assay. In FIG. 24B and 24C, IFN activity is measured using the nitrite assay. Recombinant ChIFN-γ was serially diluted in the presence of limiting amounts of recombinant ChIFN-α or natural ChIFN-β.

Figure 25A:
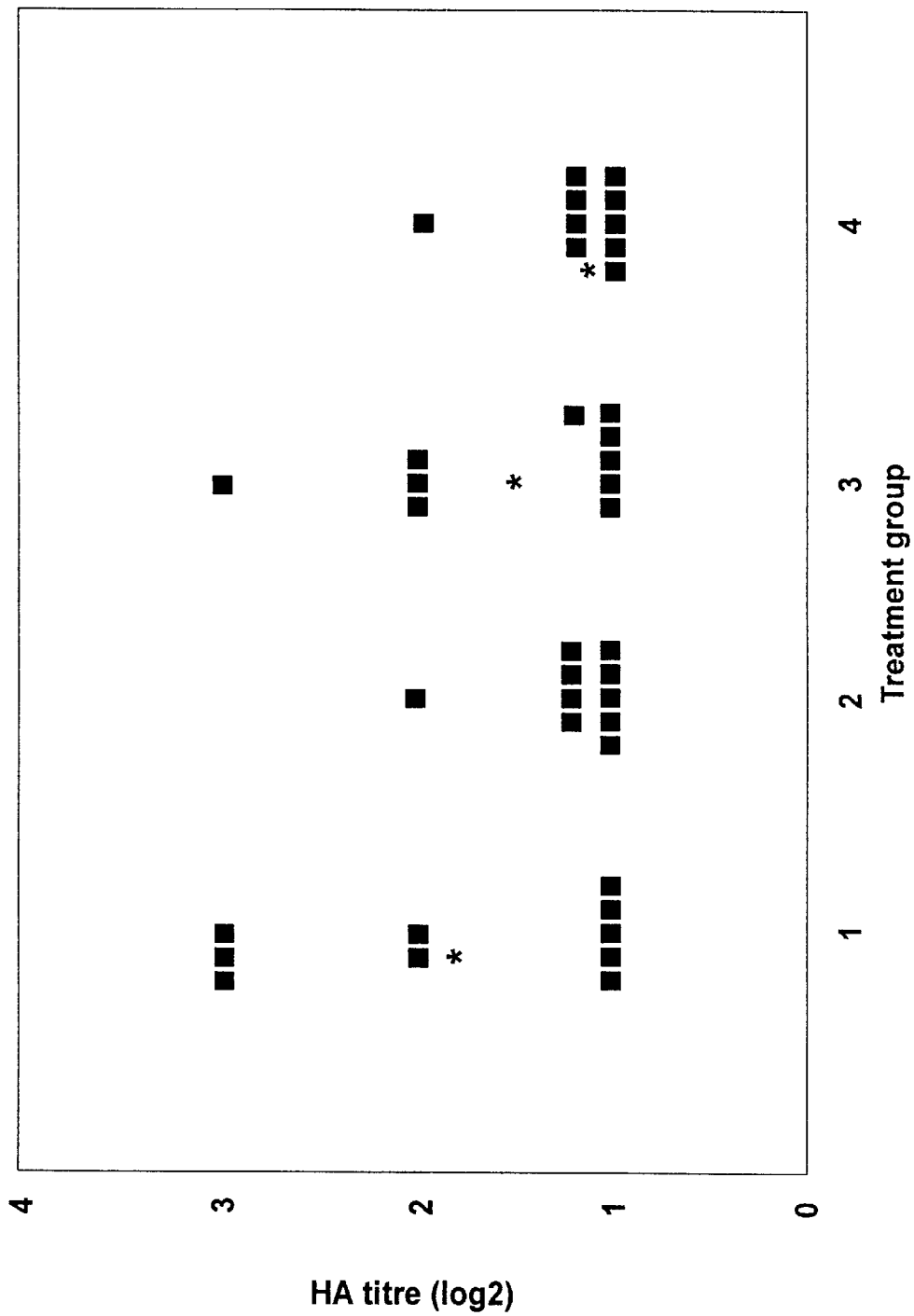
Figure 25B:
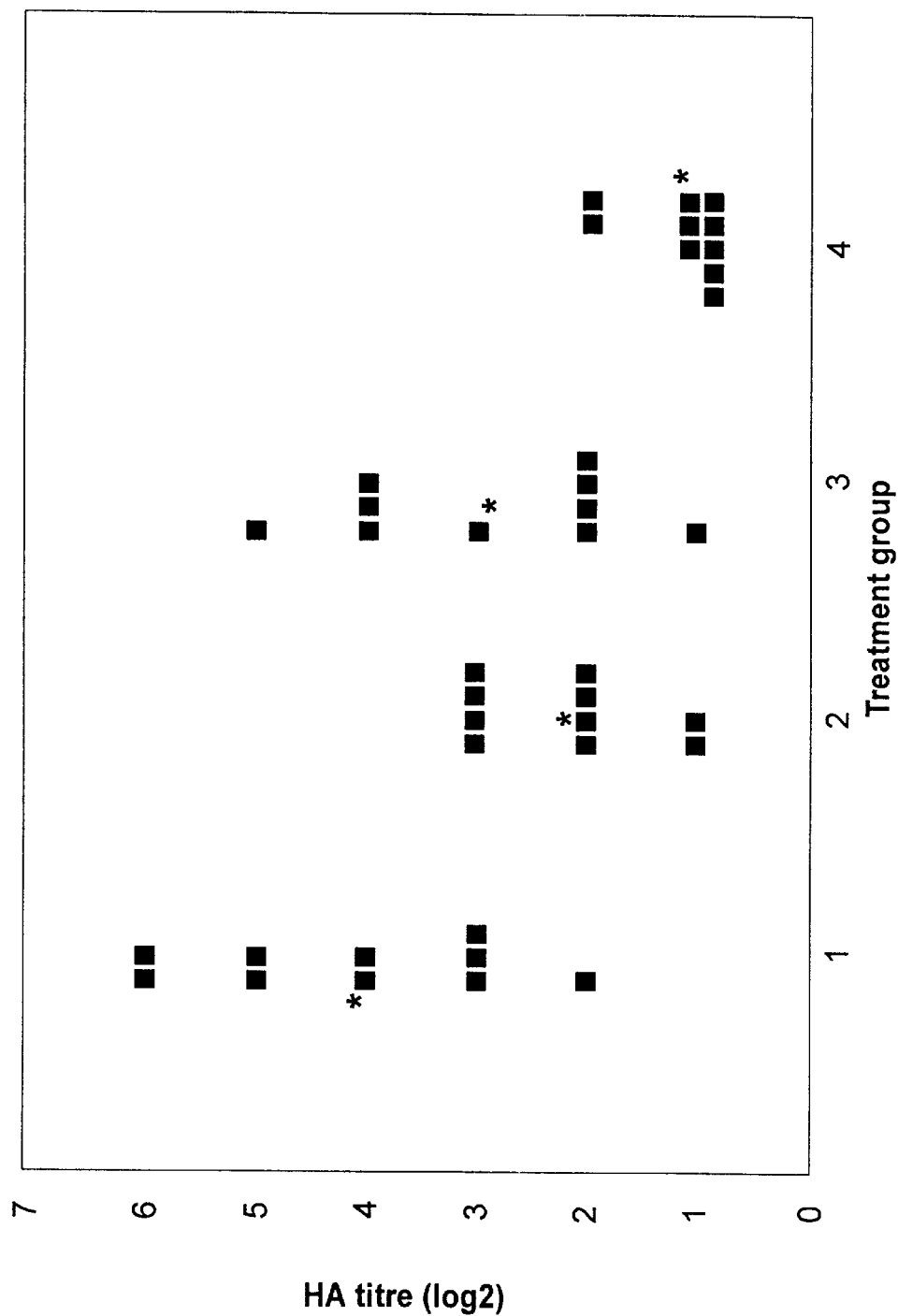
Figure 25C:
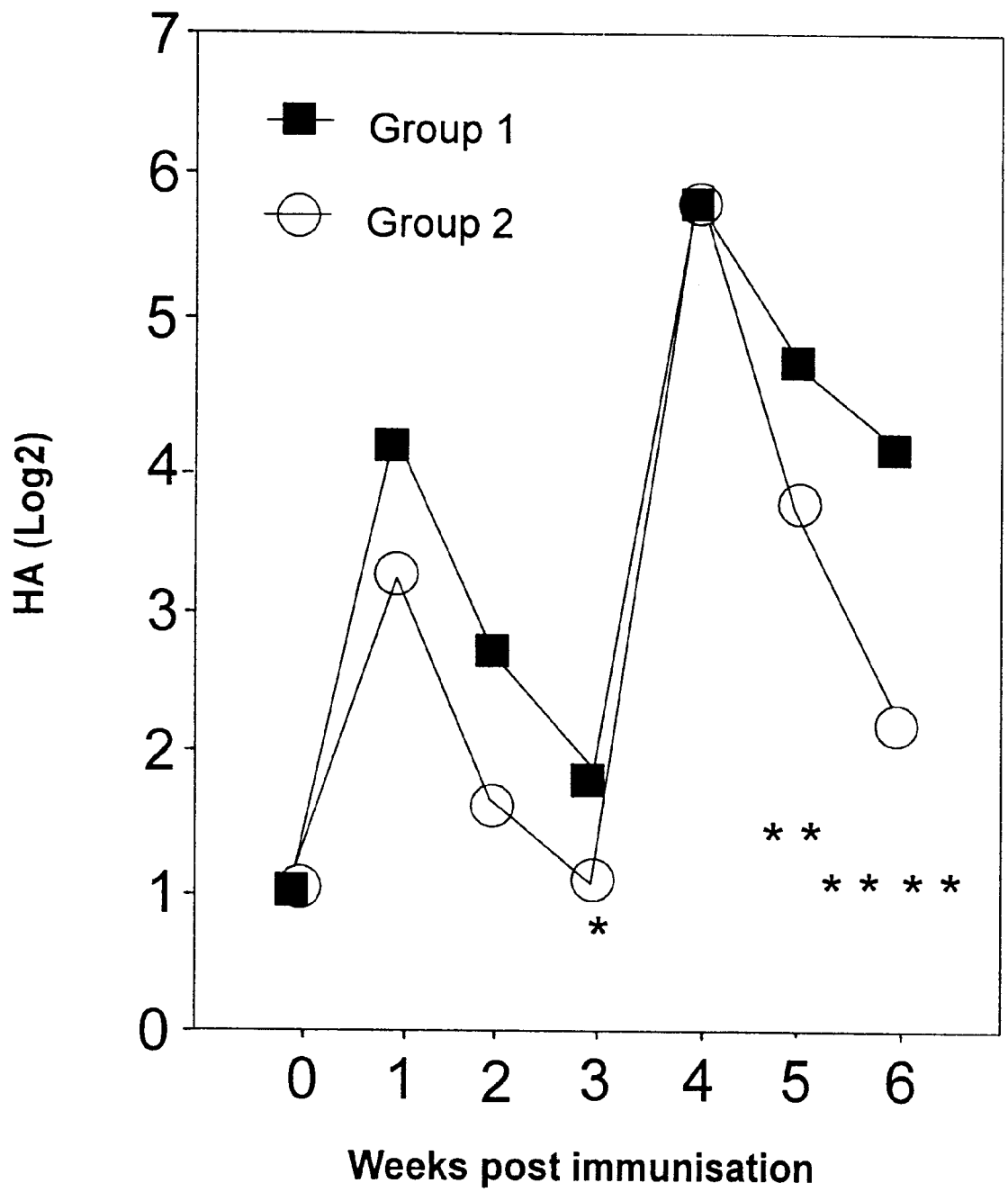
Figure 25D:
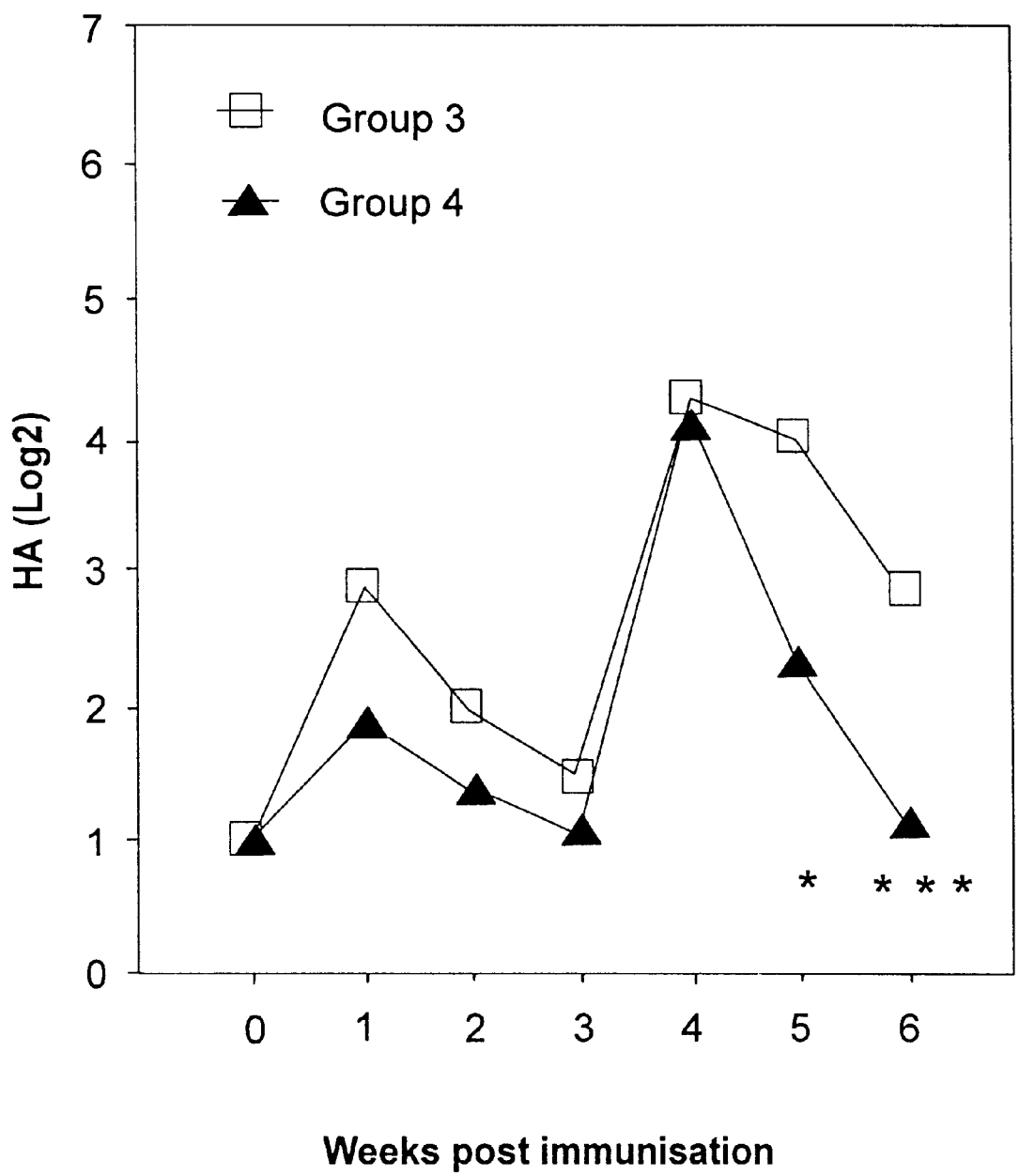
Figure 25E:
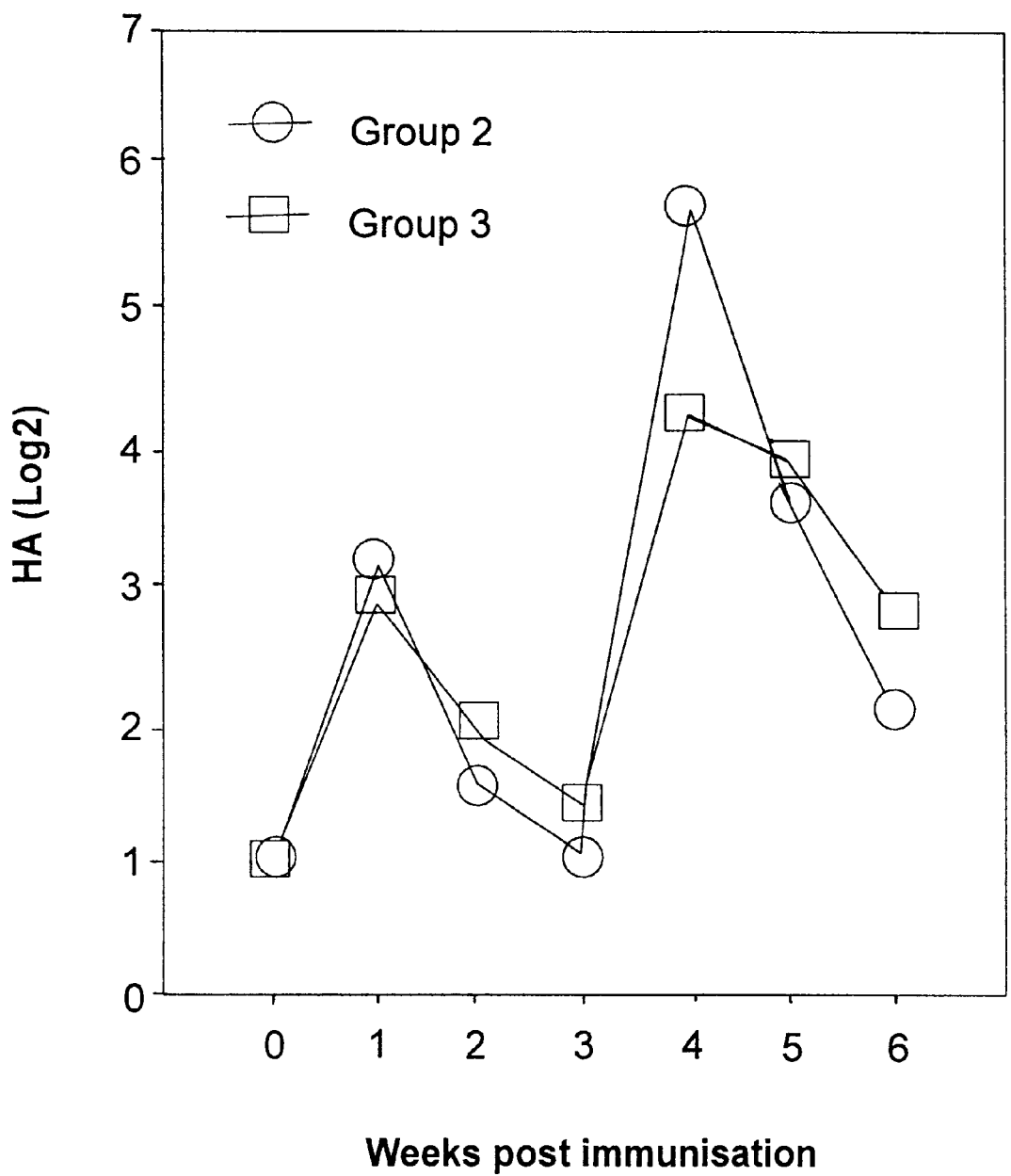
Figure 25F:
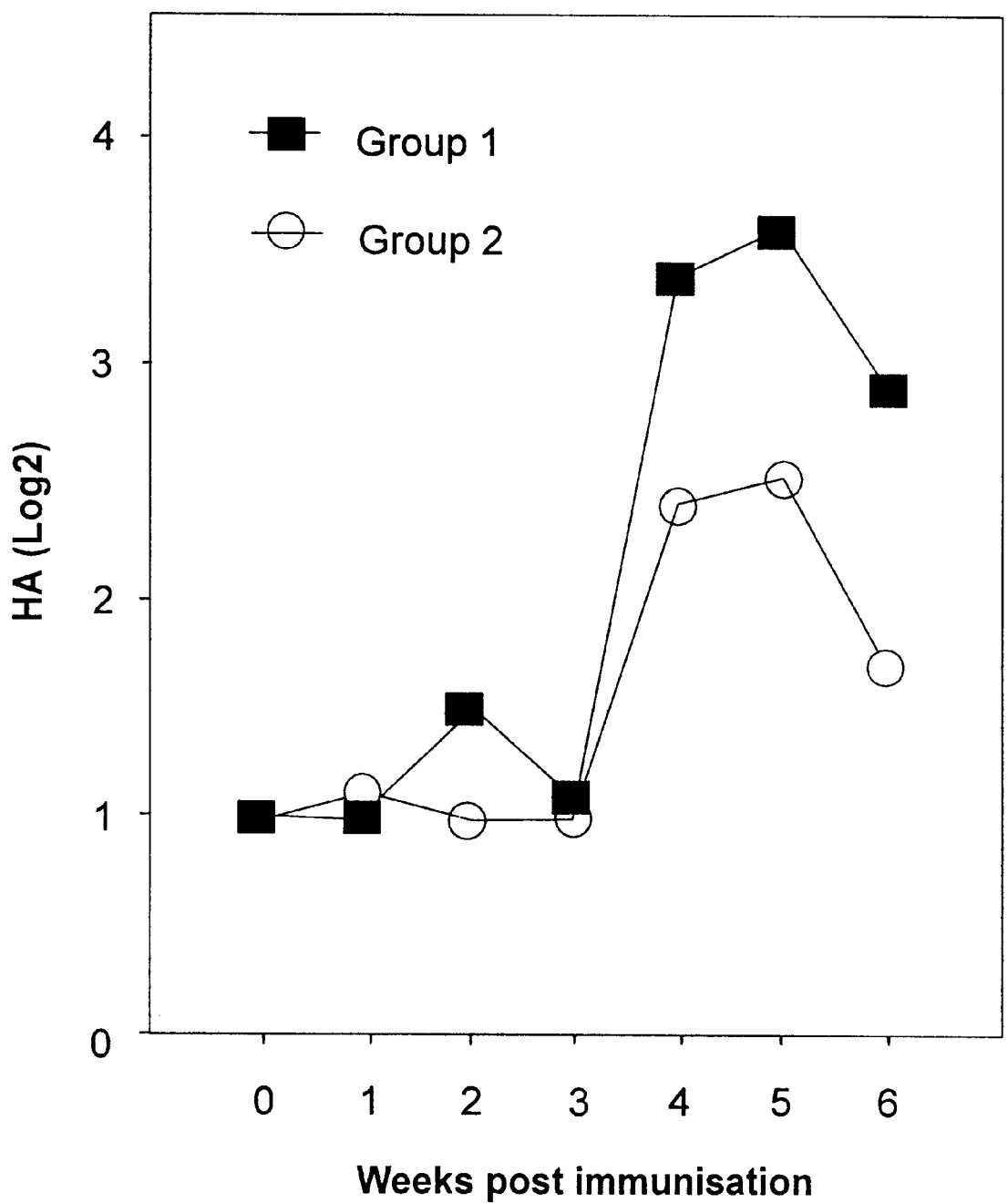
Figure 25G:
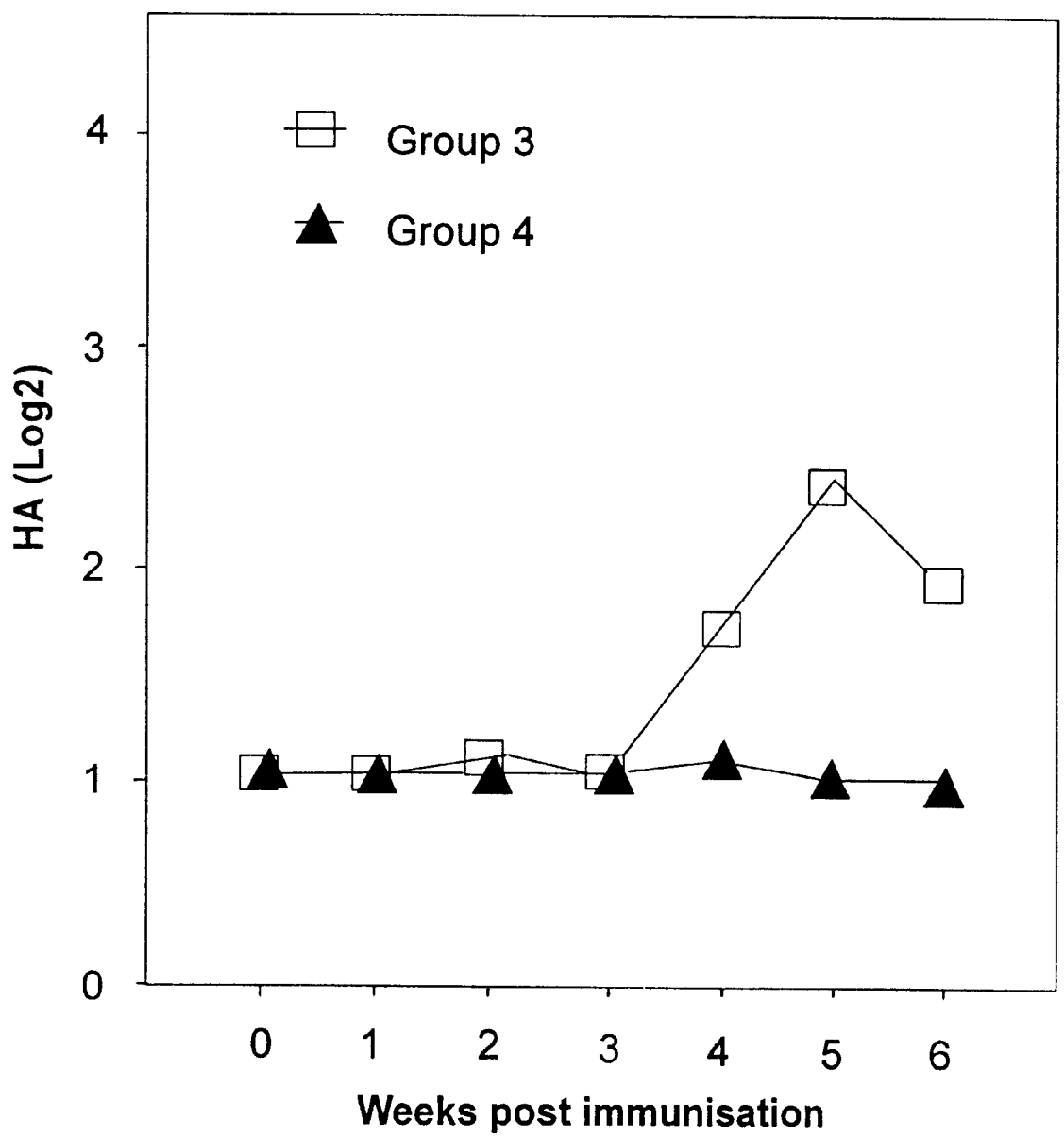
Figure 25H:
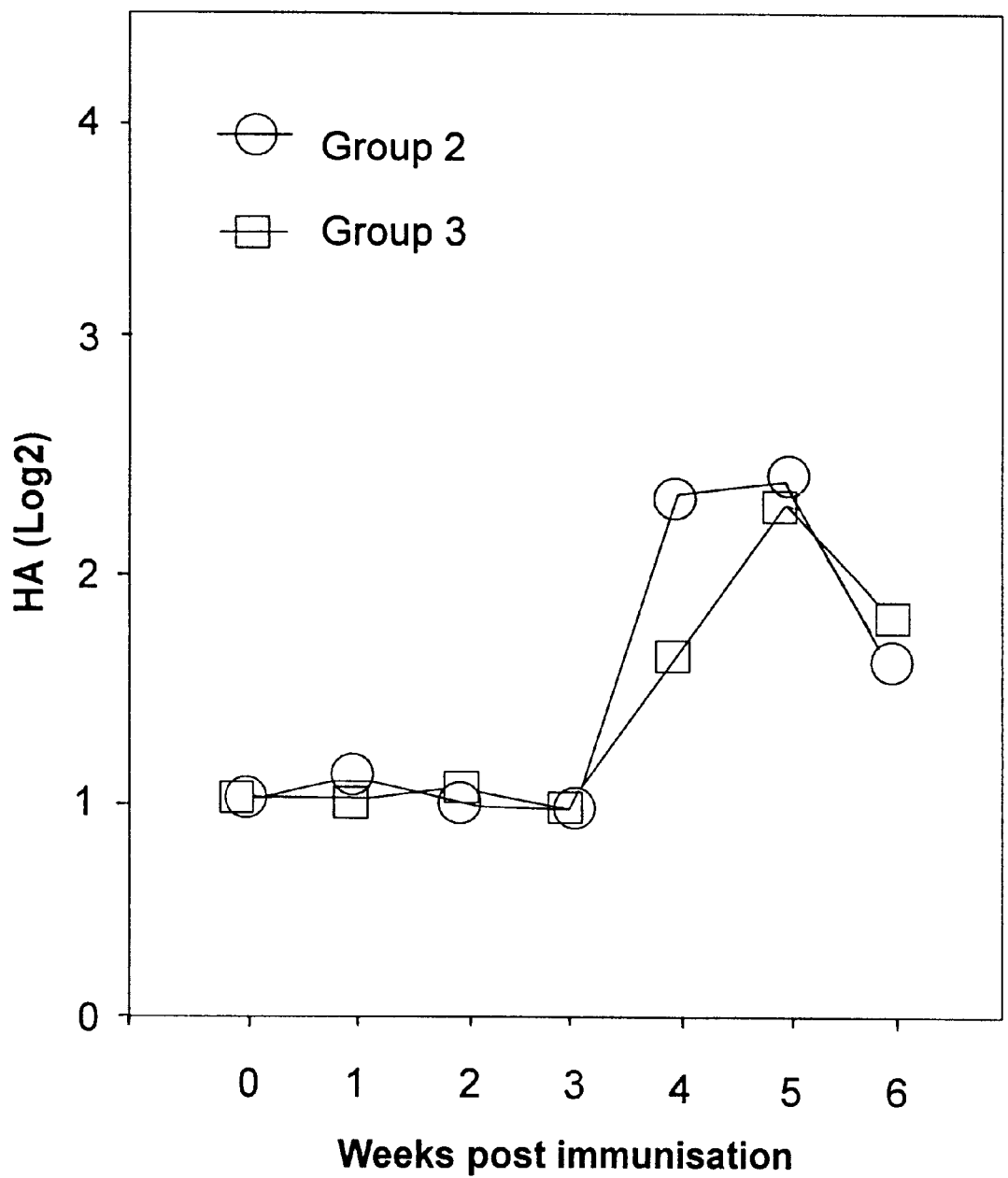

FIGS. 25a through 25h are graphical representations showing the effect of recombinant ChIFN-γ treatment in vivo on the antibody response to SRBC. Groups of birds were injected with 200 μl (Groups 1 and 2) or 20 μl (Groups 3 and 4) of SRBC and re-immunised after 3 weeks. Groups 1 and 3 were treated with recombinant ChIFN-γ (on the day before, on the day of, and on the day after primary immunisation) and Groups 2 and 4 were not treated. HA titres for total Ig and for IgG (2 mercaptoethanol-resistant Ig titres) were determined weekly for 6 weeks. FIG. 25A, Total Ig HA titres 3 weeks after the primary immunisation; FIG. 25B, Total Ig HA titres 3 weeks after secondary immunisation; FIG. 25C, Total Ig HA titres (there are significant differences between Group 1 and 2 and between Group 3 and 4: *p<0.02, p<0.05, *p<0.005, ****p<0.002); FIG. 25–F, IgG HA titres.

Figure 26:
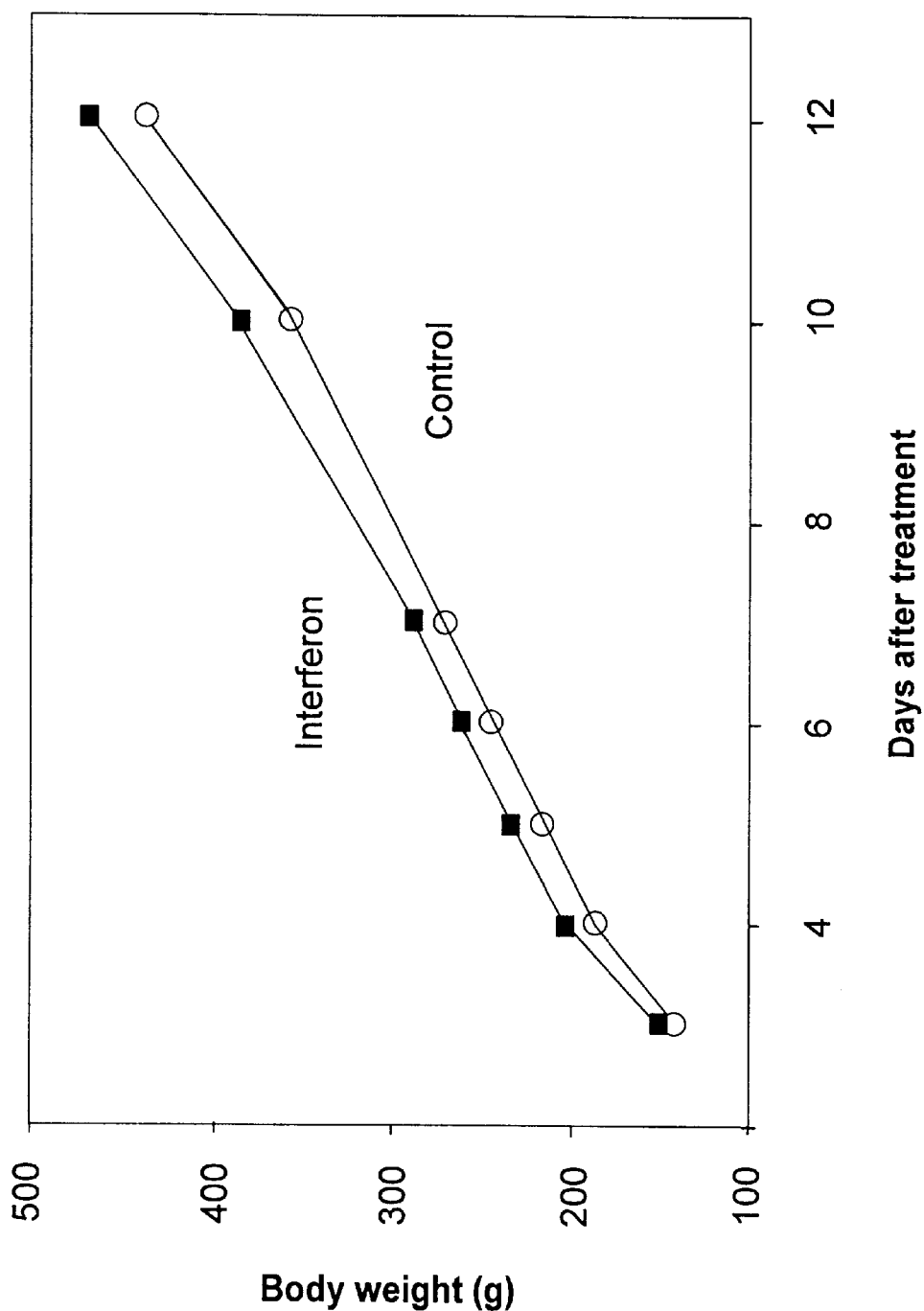

FIG. 26 is a graphical representation showing the effect of recombinant ChIFN-γ treatment in vivo on weight gain. Birds were injected with recombinant ChIFN-γ or with diluent and their body weight was monitored.

Figure 27B:
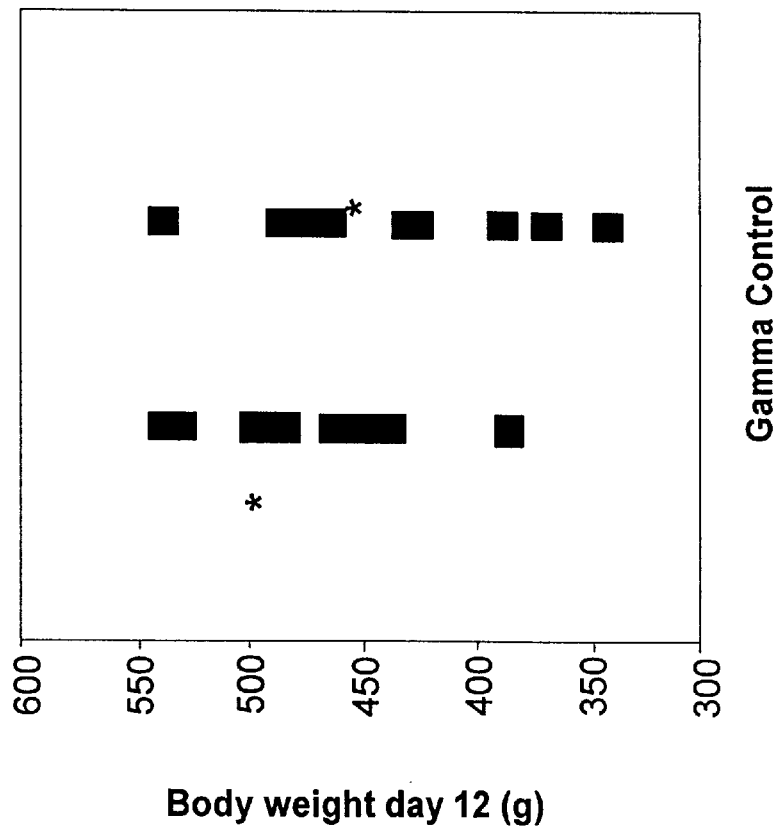
Figure 27A:
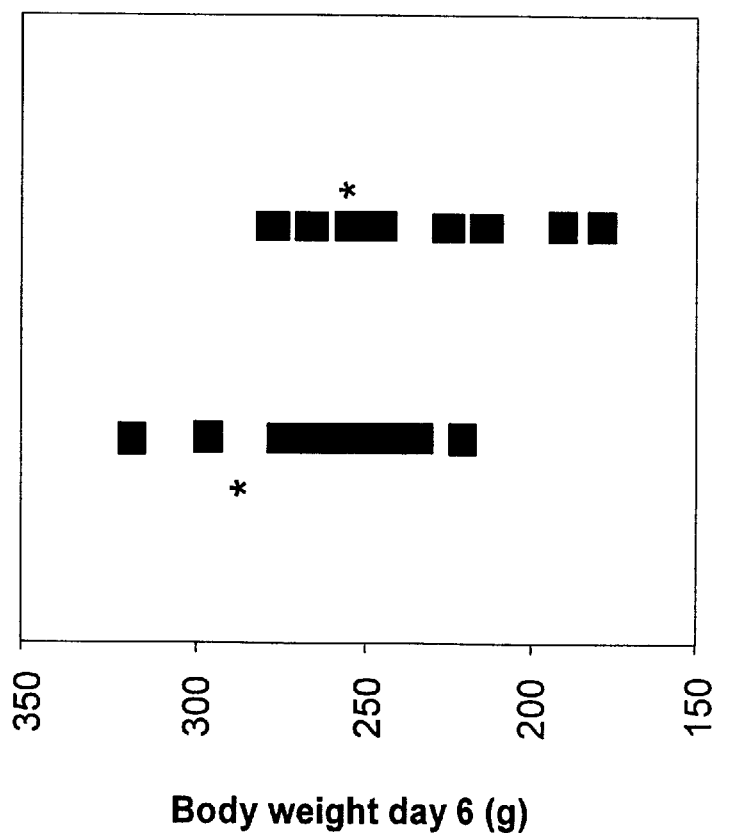
Figure 27D:
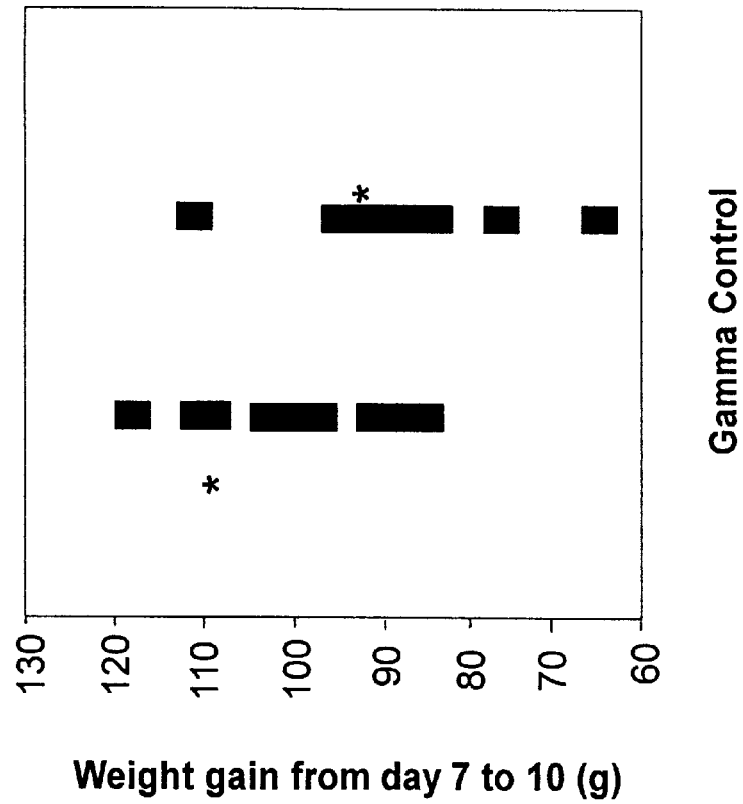
Figure 27C:
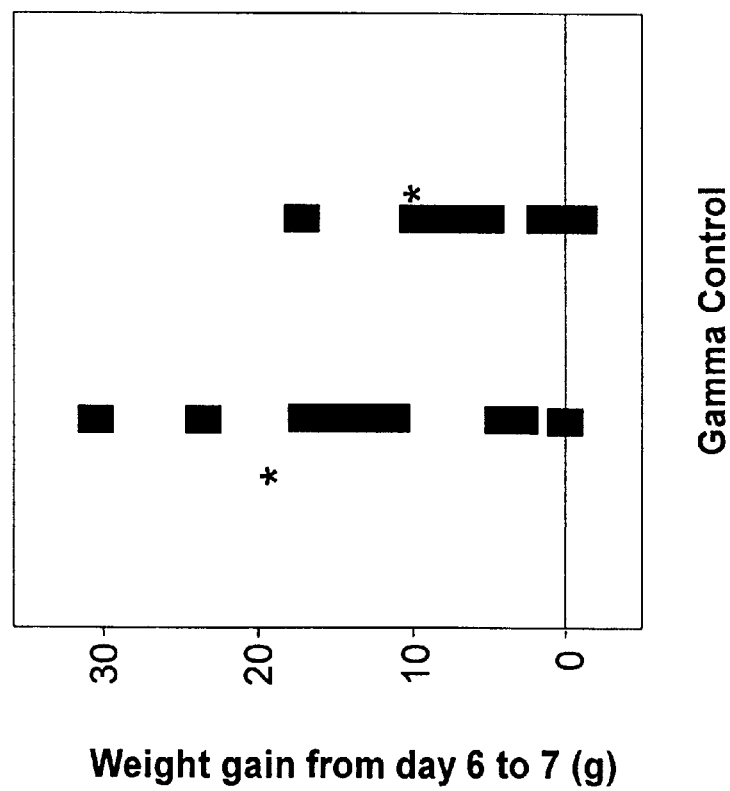

FIGS. 27A–D provide graphical representations showing the effect of recombinant ChIFN-γ treatment in vivo on weight gain. Birds were injected with recombinant ChIFN-γ or with diluent and their body weight was determined at days 6 (FIG. 27A) and 12 (FIG. 27B). Weight gain between days 6 and 7 is shown in FIG. 27C and between days 7 and 10 is shown in FIG. 27D.

Figure 28B:
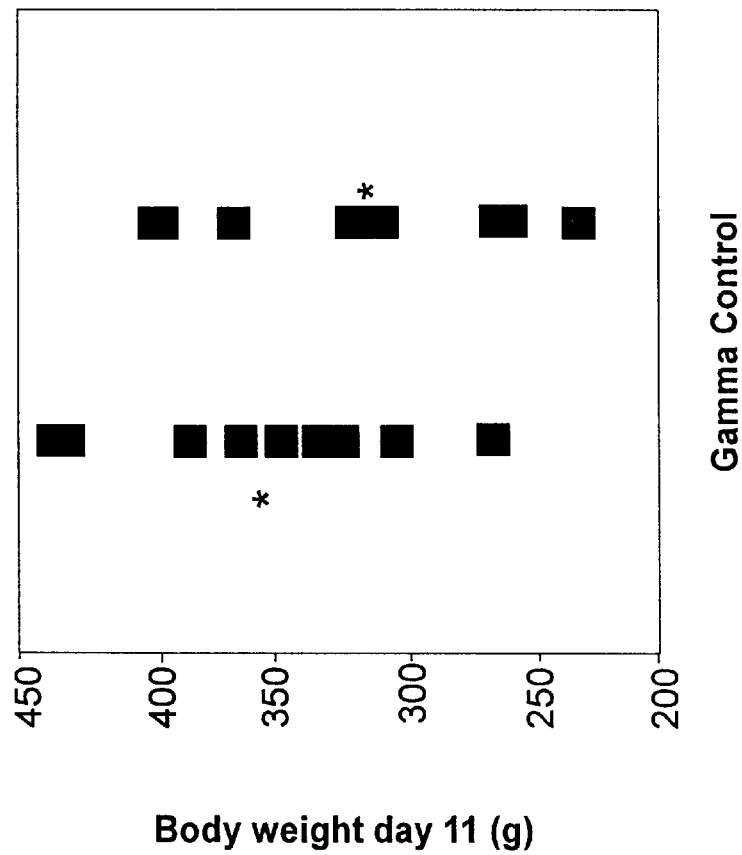
Figure 28A:
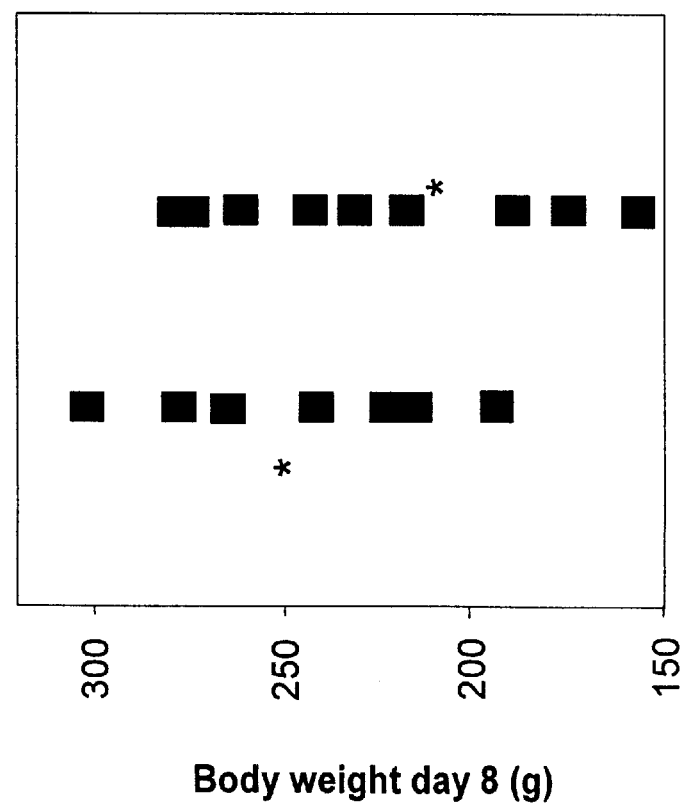
Figure 28D:
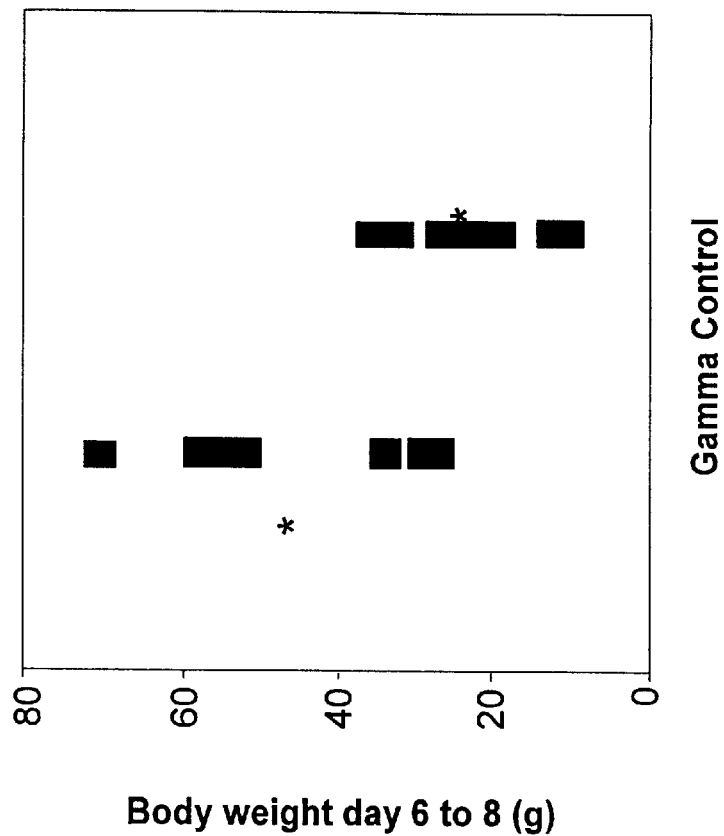
Figure 28C:
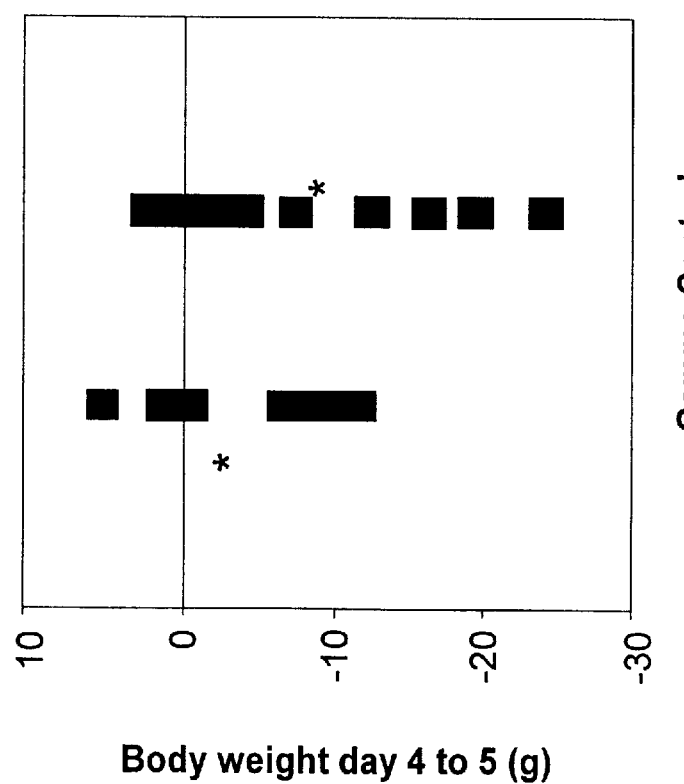

FIGS. 28A–D provide graphical representations showing the effect of recombinant ChIFN-γ treatment in vivo on weight gain during infection with E. acervulina. Birds were injected with recombinant ChIFN-γ or with diluent, infected with E. acervulina oocytes and their body weight was determined at days 8 (FIG. 28A) and II (FIG. 28B). Changes in weight between days 4 and 5 is shown in FIG. 28C and between days 6 and 8 is shown in FIG. 28D.

Figure 29:
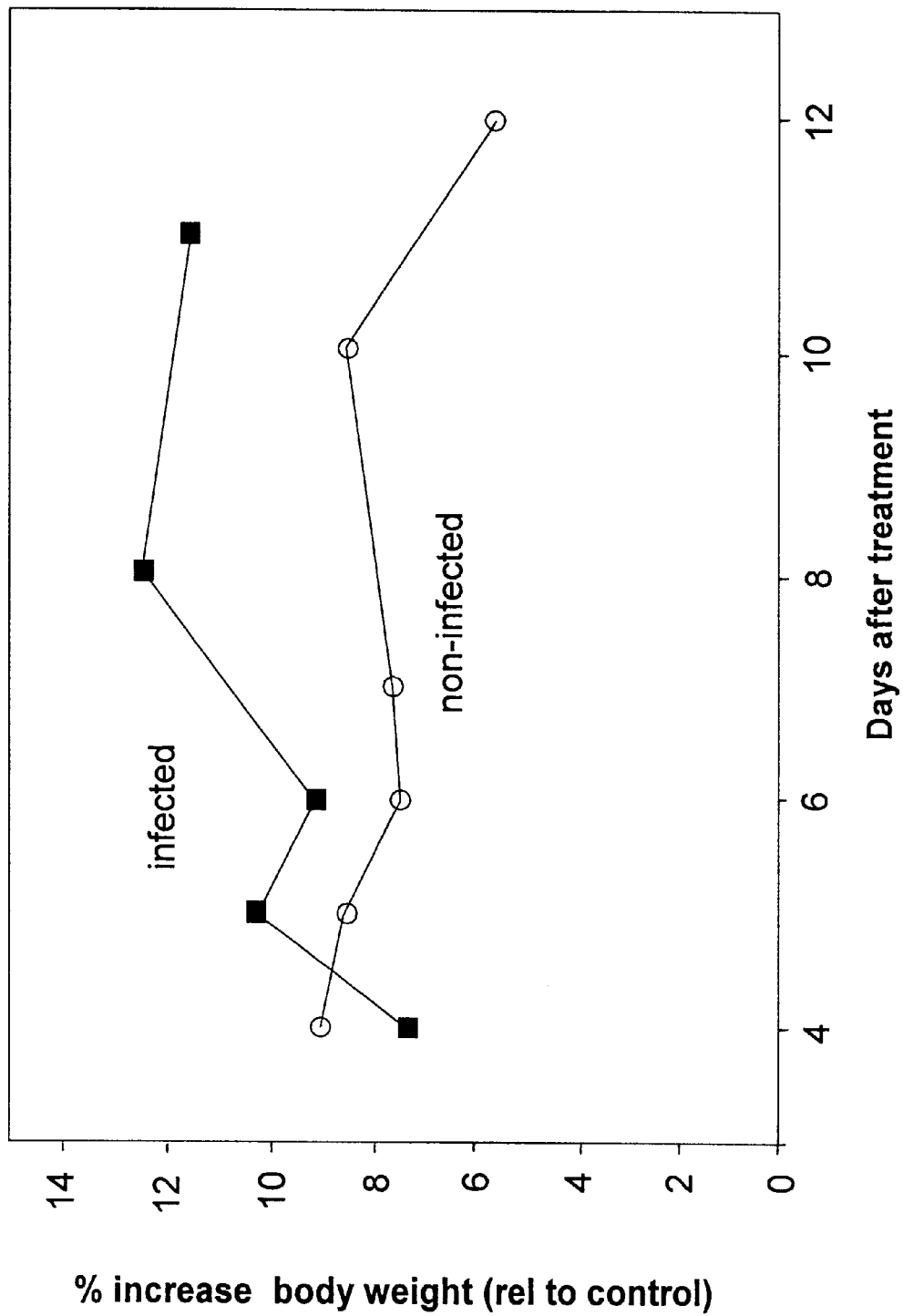

FIG. 29 is a graphical representation showing the effect of recombinant ChIFN-γ treatment in vivo on weight gain in non-infected birds and those infected with coccidiosis.

Figure 30:
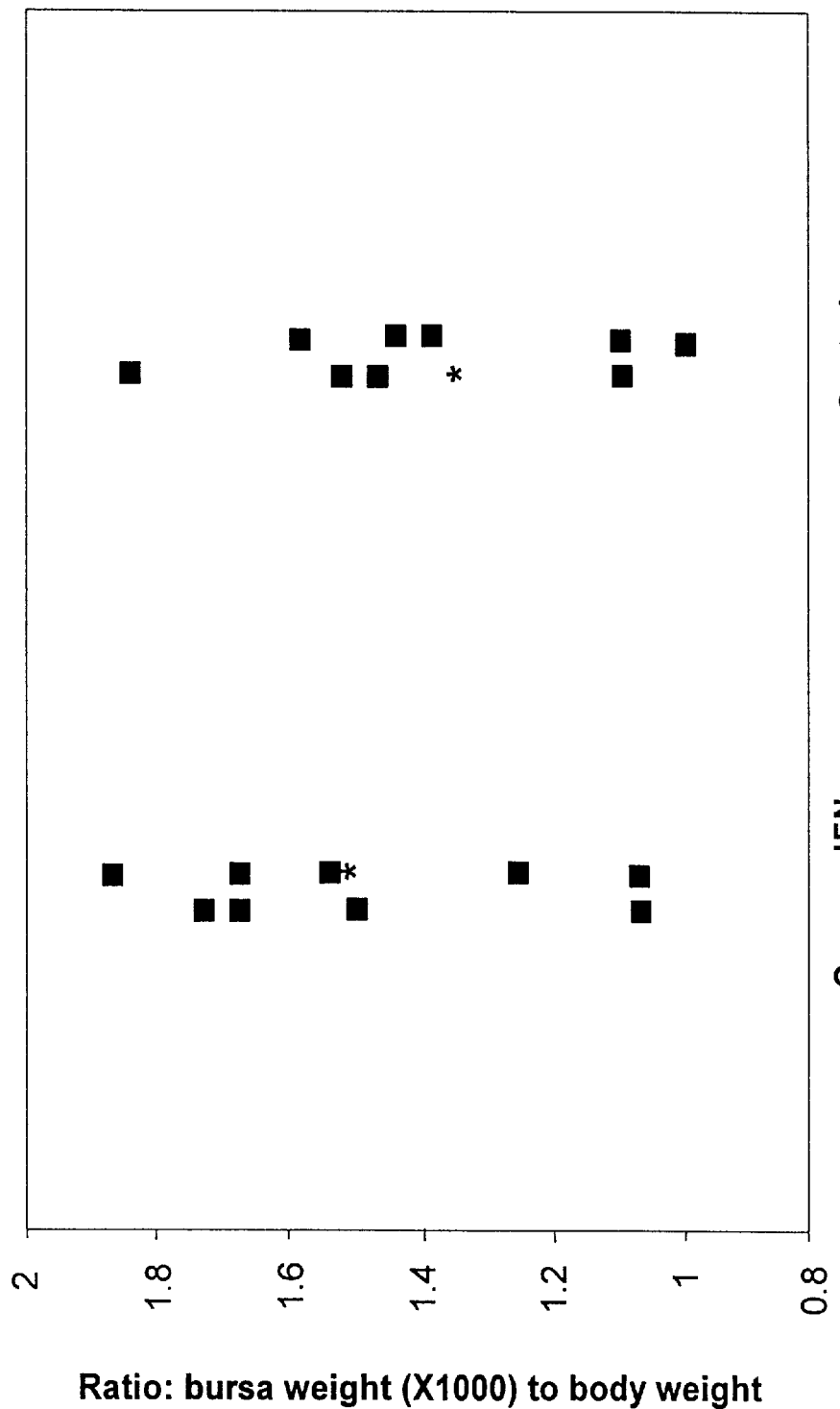

FIG. 30 is a graphical representation showing the effect of recombinant ChIFN-γ treatment in vivo on the ratio of bursa to body weight 7 days following infection with IBDV.

Figure 31:
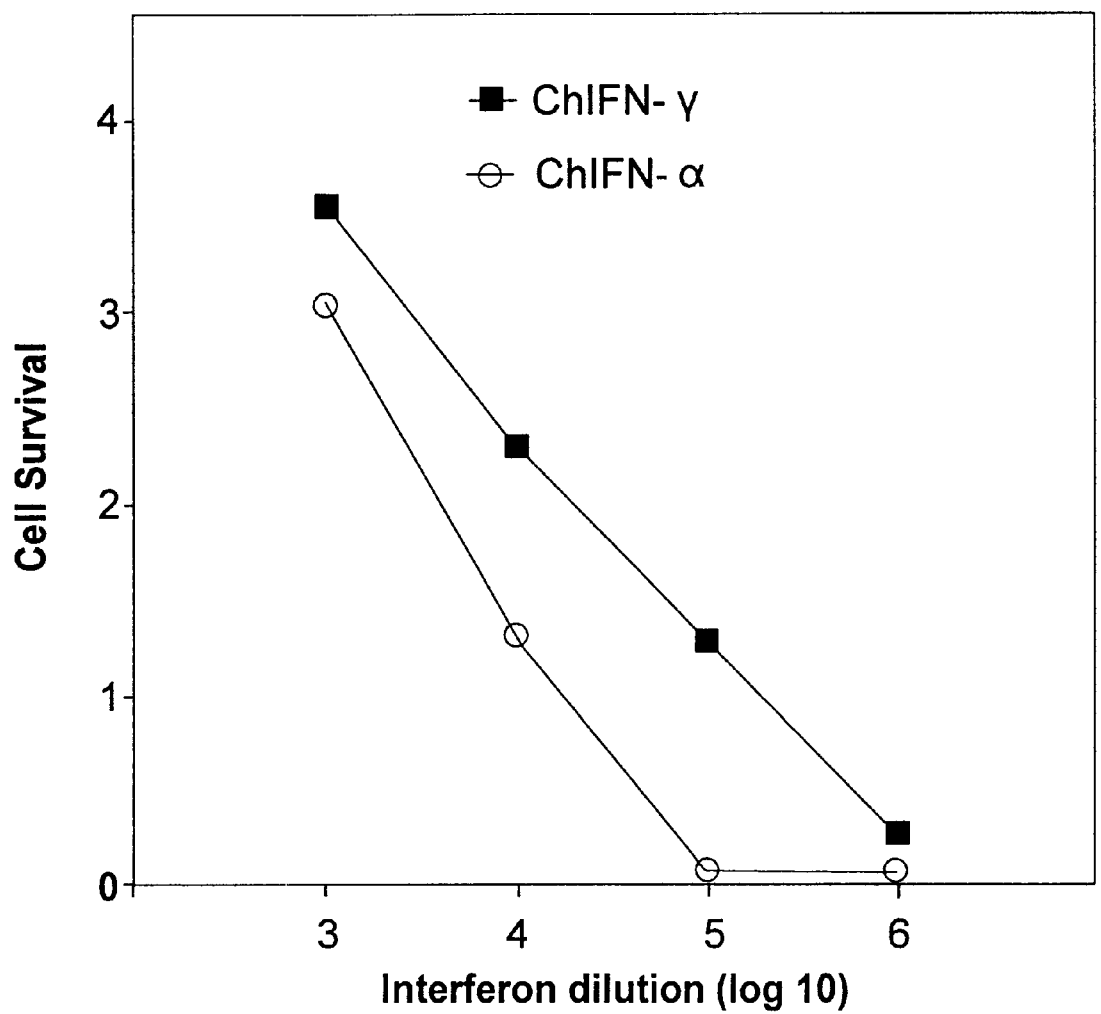

FIG. 31 is a graphical representation showing the effect of recombinant ChIFN-γ treatment in vitro on the ability to protect CEFs from infection with IBDV. CEFs were prepared as described for the CEF interferon assay. Recombinant ChIFN-γ and IBDV were added to the cultures together. Cell survival was measured 3 days later on a scale of 0 to 4, where 0 represents the level of cell survival observed in the presence IBDV and the absence of IFN (<5% cell survival) and 4 represents the level of cell survival observed in the absence of IBDV (>90% cell survival).

EXAMPLE 1

Chickens

Specific Pathogen Free (SPF) Hybrid White Leghorn (HWL) chickens produced by the CSIRO SPF poultry unit (Maribyrnong, Victoria) were raised in flexible plastic isolators and fed fumigated feed and acidified water.

EXAMPLE 2

Cell cultures

Spleens were aseptically removed from chickens and single cell suspensions were centrifuged for 5 min at 200 g. Cells were washed twice in Hanks' balanced salt solution (Flow Laboratories) and resuspended in growth medium consisting of DME medium (Flow) containing penicillin, streptomycin, 2 mM glutamine and buffered (pH 7.2) with HEPES and sodium bicarbonate. Cells were incubated at 41° C. in 5% $CO_2$ in air. Conditioned medium was prepared by culturing spleen cells ($1 \times 10^7$/ml) under serum-free conditions in the presence of Concanavalin A (ConA, 5 ug/ml, Sigma). Supernatants were collected after 24 hr, centrifuged to remove cell debris and stored at 4° C. Adherent spleen cells were obtained by incubating whole spleen cell populations in plastic petri dishes in growth media at 41° C. After 4–8 hr, non-adherent cells were removed and the plates were washed once.

EXAMPLE 3

Generation of T cell lines

REV-transformed T cell lines were generated from spleen as previously reported (Lowenthal et al 1995a, 1995b). Cells were cultured in Hahns' medium containing 1% chicken serum and 5% FBS for several days and their supernatants were assayed for interferon activity. Actively growing cell lines were stained with anti-T cell monoclonal antibodies (Mabs) CD3, CD4, CD8 and analysed by flow cytometry. Cell clones were obtained by culturing single cells in wells of 96 well microtiter plates. Actively growing clones were tested for IFN production and stained with T cell Mabs and analysed as above. Non-transformed ConA activated spleen cells failed to grow for more than 7 days and could not be cloned from single cells.

EXAMPLE 4

Chicken embryonic fibroblast (CEF) interferon assay

IFN was measured by the ability to protect CEF and turkey embryonic fibroblasts (TEF) from virus-mediated as described by Prowse and Pallister (1989), Lowenthal et al (1995a) and Lowenthal et al (1995b). Secondary fibroblasts were seeded into 96 well microtiter plates ($5 \times 10^4$/well) and grown in the presence of 10% FBS at 41° C. After 24 hr the culture medium was replaced with 100 μl of serum-free growth medium and 2-fold serial dilutions of test supernatants were made in duplicate. Control wells contained cells cultured in medium alone or cultured in the presence of a reference supernatant of known IFN activity. After overnight incubation at 37° C., the culture medium was replaced with 100 μl of medium containing Semliki Forest virus or Vesicular Stomatitis virus ($10^3$ tissue culture infective dose / ml) and the cells were incubated at 37° C. After 24 hr, cell viability was measured by uptake of neutral red dye and absorbance at 540 nm was quantitated using an ELISA reader.

EXAMPLE 5

Treatment of IFN

Supernatants were heated at 60° C. in Eppendorf tubes for various periods of time and immediately placed on ice. Supernatants were exposed to low pH treatment as follows: a sufficient quantity of 2M HCl was added to attain a pH of 2.0. After 8 hr at 4° C., the pH was adjusted to pH7.0 using 5M NaOH. Sensitivity of IFN to reducing agents was measured by adding 0.5% (V/V) 2-mercaptoethanol (2-ME) to supernatants. All supernatants were then stored at 4° C.

EXAMPLE 6

Nitrite assay

Production of nitric oxide by HD11 chicken macrophages (Beug et al, 1979) was quantitated by accumulation of nitrite in the culture medium (Sung et al, 1991) and was used as a measure of IFN-γ activity. Two-fold serial dilutions of test supernatants were made in duplicate wells of 96 well plates in a volume of 100 μl of growth medium containing 5% FBS. HD11 cells were added to each well ($10^5$ in 100 μl) and the plates were incubated at 37° C. After 24 hr, 50 μl of culture supernatant was added to100 μl of Griess reagent (1:1 mixture of 1% sulfanilamide and 0.1% naphthylethylene diamine in 2.5% $H_3PO_4$) and absorbance was read at 540 nm. The level of nitrite was determined using sodium nitrite as a standard.

EXAMPLE 7 cDNA library production and transfection of COS cells

PolyA$^+$ RNA from the CC8.1h T cell clone (AGAL Accession No. N94146035) was directionally cloned into the eucaryotic expression vector pcDNAI (Clontech, Palo Alto, Calif.). Pools of 100 clones were transfected into COS cells by the DEAE-dextran method as follows: 1 μg of DNA was mixed with 10 μl of DEAE-dextran (10 mg/ml, Sigma) and added to $1 \times 10^6$ cells in 0.5 ml of media containing 1% FBS. Cells were incubated in Eppendorf tubes at 37° C. After 30 min, 0.5 ml of 25% (v/v) DMSO in DME was added and mixed. After 5 min the cells were washed in media and resuspended in 5 ml of DME with 2% FBS and cultured for 3 days at 37° C. Supernatants were tested for IFN activity as described in Example 4 and Example 6. E. coli were then transformed with positive plasmid pools and new plasmid preparations were made from pools of 10 individual colonies. COS cell transfection and supernatant screening was repeated and positive pools were identified. The process was repeated until single positive clones were isolated. The insert was subcloned into Bluescript IKS and the nucleotide sequence of both strands was determined using an automated gene sequencer.

EXAMPLE 8

Expression of ChIFN-γ in E. coli.

The mature coding region of ChIFN-γ was cloned into the pQE expression vector (QIAexpress Type IV construct, Qiagen, Calif.) according to manufacturers instructions. The sequence of the oligonucleotides used to PCR the mature region of the gene is as follows:

```
sense     5' ACTAGATCTCATACTGCAAGTCTAAAT 3'
antisense 5' ACTAAGCTTTTAGCAATTGCATCTCCTCTG 3'
```

All procedures used for the expression of recombinant ChIFN-γ using Ni columns and purification was according to manufacturers instructions.

EXAMPLE 9

Preparation of antibodies to ChIFN-γ

Rabbit antisera was raised against purified recombinant ChIFN-γ protein. Rabbits were immunized three times with 400 μg of protein and sera was collected 10 days after the final injection. Specific reactivity of the sera to ChIFN-γ was confirmed using immune and pre-immune sera in Western blots and in assays measuring the ability to inhibit the release of nitrite by HD11 cells.

Monoclonal antibodies (Mabs) were raised by immunising mice 4 times with 10 μg of recombinant ChIFN-γ and screening was performed using Western blots.

EXAMPLE 10

Expression of Class II molecules

HD11 cells were cultured at 41° C. in the presence of recombinant and native ChIFN-γ for 48 hrs and were then analysed for the cell surface expression of Class II. Cells were washed twice and incubated for 20 min with monoclonal anti-Class II antibody (MUI 78 ) followed by incubation with FITC-sheep anti-mouse Ig (Fab 2). They were then washed three times and fixed by resuspending in PBS containing 1% paraformaldehyde. Cell suspensions were analysed using a FACScan (Becton Dickinson, Mountain View, Calif.). with a total of $10^4$ cells analysed for each sample.

EXAMPLE 11

ChIFN-γ as an adjuvant

Four Groups (n=10) of 3-week old SPF chickens were injected intramuscularly with either 0.2 or 0.02 ml of sheep red blood cells (SRBC). One group at each dose was also injected intra-peritoneally with 500 Units of recombinant ChIFN-γ the day before and on the day of immunization. Birds were bled weekly and haemaglutination titres of the sera were determined.

EXAMPLE 12

Effect of recombinant ChIFN-γ on infection with Infectious Bursal Disease Virus in vivo One group (n =10) of three-week old SPF chickens was injected intraperitoneally with 500 Units of recombinant ChIFN-γ on 2 consecutive days and another group of control birds (n=10) was injected with diluent alone. Both groups of birds were infected intraocularly with Infectious Bursal Disease Virus (IBDV). Birds were sacrificed 7 days later and the bursa and whole body weights were determined.

EXAMPLE 13

Production of IFN

Spleen cells were cultured at 41° C. in the presence of a variety of mitogens and the supernatants were tested after 24 hr for the presence of IFN activity using the CEF assay. The results are summarized in Table 2. Preliminary experiments showed that culturing the cells at 41° C. resulted in approximately 5-fold higher levels of interferon compared to 37° C. The optimal cell concentration was $5 \times 10^6$ leukocytes/ml. Kinetic experiments revealed that IFN was first detected 4 hr after stimulation and reached maximal levels at 24 hr (data not shown). Recombinant IFN (-α, -β or -γ) from human murine, bovine, avian and porcine species were all inactive in the CEF assay at concentrations of up to $10^4$ U/ml (Digby and Lowenthal, 1995).

EXAMPLE 14

Characterisation of IFN types

Supernatants collected from CEF infected with Semliki Forest virus were used as a source of IFN-β (Sekellick and Marcus, 1986) and treated as described in Example 5.

Figure 1:
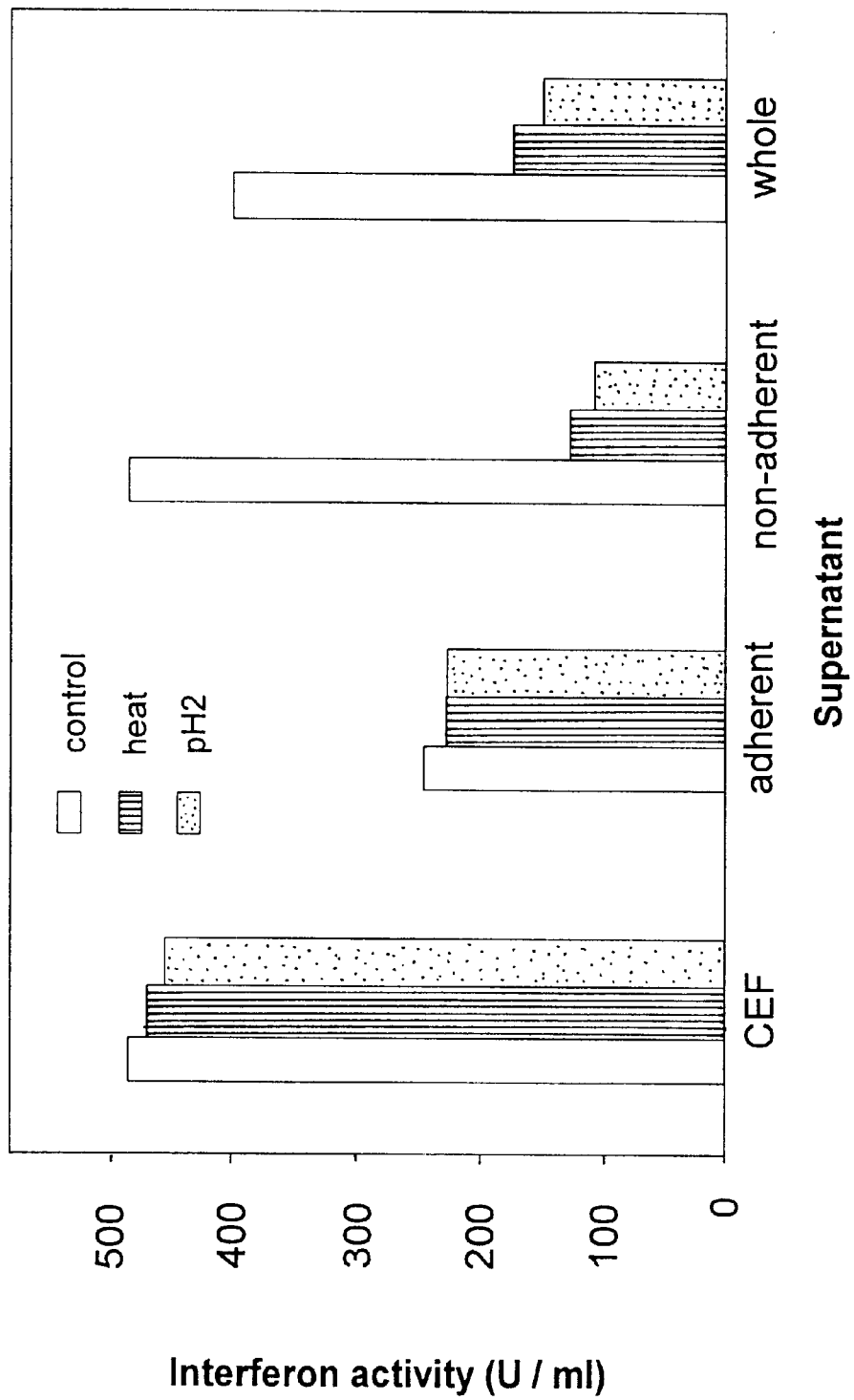

In agreement with previously published results (von Bulow et al, 1984; Thacore et al, 1985) interferon produced by CEF is resistant to heating at 60° C. and to pH2.0 treatment (FIG. 1). Spleen cell populations were either enriched for adherent cells (mostly monocytes), enriched for non-adherent cells or left as whole spleen populations. IFN production was induced by culturing the cells for 24 hr in the presence of ConA or LPS. Approximately 95% of the IFN activity produced by adherent cells was resistant to heating at 60° C. for 1 hr and exposure to pH2.0 (FIG. 1), consistent with IFN-α/β activity. In contrast, only 25% of the IFN activity produced by ConA activated non-adherent spleen cells was resistant to heat or pH2.0 treatment. These results indicate that this T cell-enriched population produced predominantly IFN-γ, but that a significant amount of IFN-α/β is also present. Whole spleen populations produced a mixture of resistant and labile IFN.

Figure 2:
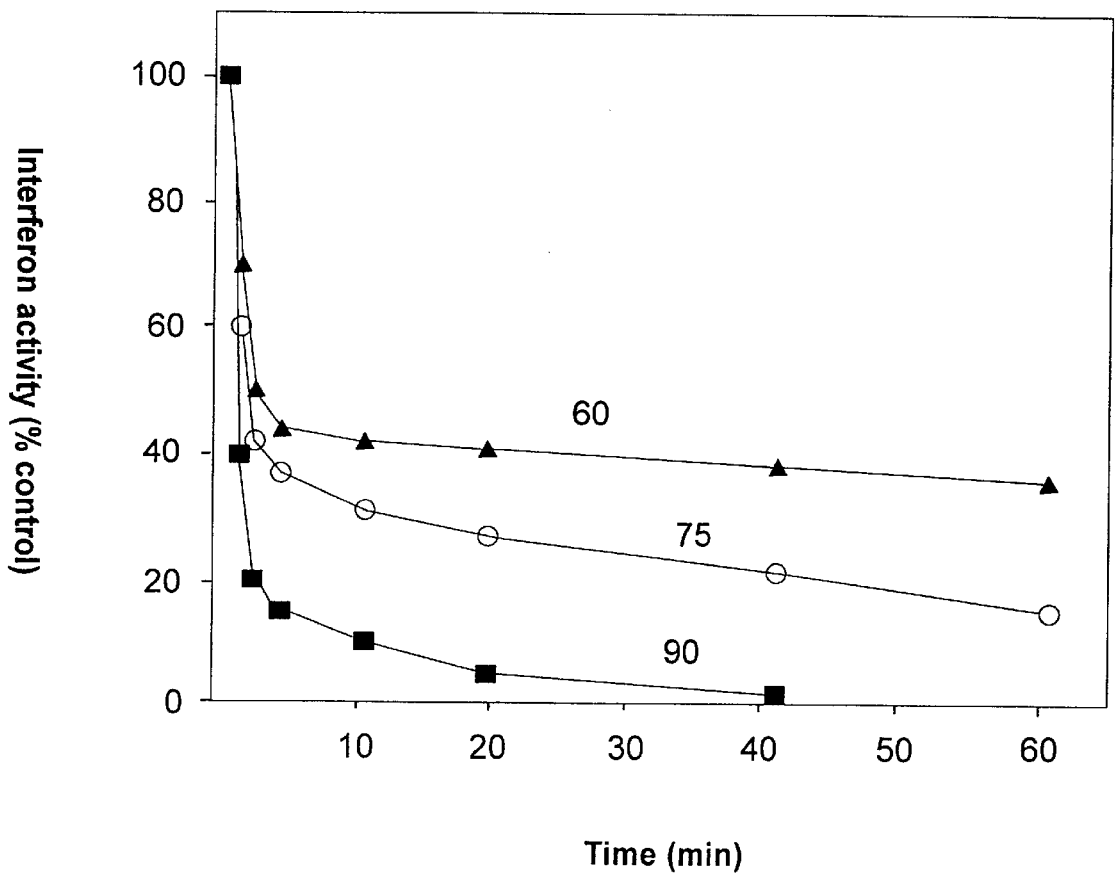
FIG. 2 is a graphical representation showing sensitivity of IFN activity to heat. Supernatants from ConA activated spleen cells were heated for up to 1 hr as indicated and then tested for activity in the CEF assay.

Supernatants from whole spleen cell populations were heated for various periods of time as described in Example 5 and subsequent loss of IFN activity was measured. Kinetic experiments confirmed that supernatants from ConA induced whole spleen cell populations (CS) contained a mixture of heat-sensitive and heat-resistant IFN. About 60% of IFN activity was lost within 1–2 min of heating to 60° C. while the resistant faction lost activity much more slowly with a half-life of >2 hr (FIG. 2). Exposure to higher temperatures increased the rate of loss of activity for the resistant but not the sensitive IFN.

EXAMPLE 15

Production of chicken T cell lines

The phenotype of some representative REV-transformed chicken T cell lines are shown in Table 3. Supernatants from these cell lines were measured for the presence of IFN-γ. The CC8.1 cell line and its clones were found to produce high levels of IFN activity (Table 3). Clones were analysed 7–8 days after cloning and were clearly positive for CD3 and CD4 surface markers. Clones kept continuously in culture for 6 months continued to secrete high levels of IFN-γ. We refer to this type of IFN as chicken IFN-γ (ChIFN-γ)

ChIFN-γ production is constitutive because exposure of these cell lines to various stimuli (ConA, PHA, CD3 Mabs, TCR Mabs or combinations of these) increased ChIFN-γ levels by less than 2-fold (Table 2).

Figure 3:
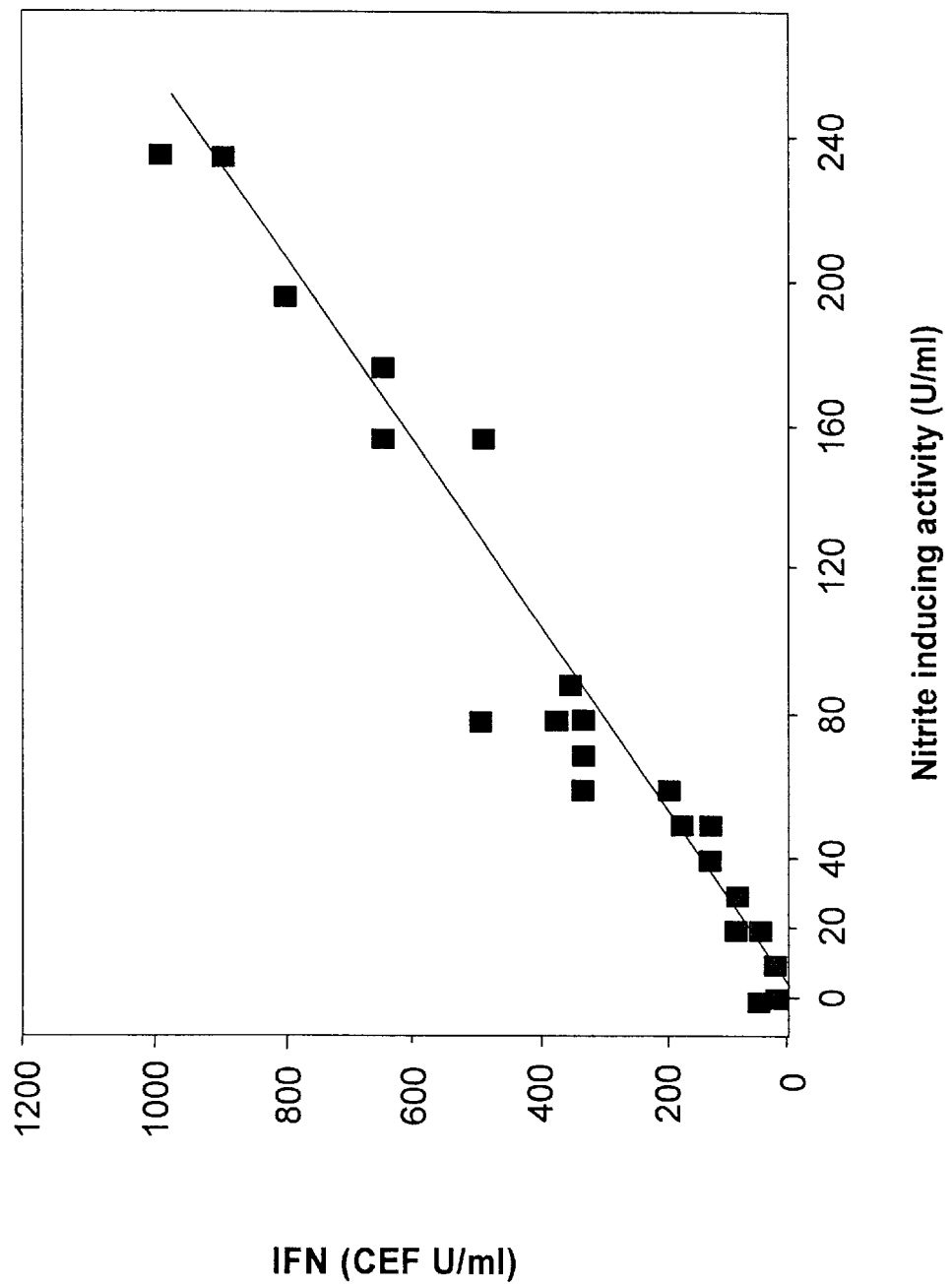
FIG. 3 is a graphical representation showing the ability of supernatants from the CC8.1 T cell line (AGAL Accession No. N94/46035) to protect CEF from virus mediated lysis and their ability to induce HD11 cells to secrete nitrite.

Several clones were obtained from the CC8.1 cell line and were measured for their ChIFN-γ production using the CEF assay described in Example 4 or the nitrite assay described in Example 6. There was a considerable variation in the amount of ChIFN-γ produced by individual clones, however, the ratio of IFN titer as measured in the CEF assay to that of the nitrite-inducing activity remained constant (FIG. 3). When ChIFN-γ present in the supernatant from a chicken T cell clone (CC8.1h) was heated to 60° C. it was shown to be labile. (FIG. 4).

EXAMPLE 16

Characterisation of ChIFN-γ

In order to further characterize ChIFN-γ produced by chicken T cells, supernatants from CC8.1h were treated in various ways including exposure to pH2 and 2-ME as described in Example 5. The majority (~80%) of the ChIFN-γ activity was sensitive to either heat or pH2 treatment when measured in the CEF assay as described in Example 4 (FIG. 5). The combination of heat and pH2 treatment did not result in a further loss of activity. The majority of ChIFN-γ activity also was resistant to exposure to 2-ME and this 2-ME-resistant IFN was heat-labile. The properties of ChIFN-γ is highly consistent with the physio-chemical profile reported for mammalian IFN-γ.

In mammals, IFN-γ can be distinguished from IFN-α/β by its ability to stimulate nitrite production by macrophages. In order to confirm that this also held true for ChIFN-γ, T cell supernatants were assayed for their ability to induce HD11 macrophages to produce nitrite. CC8.1h supernatant contains approximately 2400 U/ml of IFN activity when measured by the CEF assay (Example 4) and 640 U/ml of IFN as measured by the nitrite assay (Example 6). When heated for 30 min at 65° C., the IFN titer of this supernatant was reduced to 10 U/ml (FIG. 6), indicating that the heat labile ChIFN-γ was responsible for the nitrite-inducing activity. On the other hand, supernatants with 4000 U/ml of IFN-P (as measured by the CEF assay of Example 4) contain only low levels of nitrite-inducing activity which is not heat labile (FIG. 6). Furthermore, the nitrite-inducing activity produced by these T cells was found to be heat-labile, with ~90% of the activity lost within 5 min of heating to 60° C. (FIG. 7). These results indicate that avian IFN-β, like its mammalian counterpart, is very inefficient in inducing nitrite secretion when compared to IFN-γ.

Table 4 summarizes the production of IFN by CEF and CC8.1h T cells. It compares the CEF IFN titers and the nitrite-inducing titers for supernatants of both cell types. The ratio of CEF to nitrite titers for T cell-derived ChIFN-γ is 5 compared to 480 for CEF derived IFN-β. This result is consistent with that found in mammals where IFN-γ is superior to IFN-β in its ability to induce nitrite secretion.

EXAMPLE 17

Identification of the ChIFN-γ gene.

A cDNA expression library was generated from the CC8.1h chicken T cell line as described in Example 7. Pools of 100 cDNA clones were transfected into COS cells and supernatants were tested for IFN bioactivity 2 to 4 days later. Several supernatants were found to be active in both the CEF (FIG. 8A) and nitrite (FIG. 8B) assays. The IFN activity was sensitive to heat and pH 2 treatment, indicating the presence of a functional IFN-γ gene in the plasmid pool. Positive pools were individually transformed into E. coli and plasmid preparations were generated from pools of 10 clones. Several of these plasmid pools were positive for the IFN-γ gene and the process was repeated until single positive clones (eg. 148.1.7 and 148.1.9) were isolated (FIG. 9).

EXAMPLE 18

Characterization of recombinant ChIFN-γ.

COS cells transformed with plasmid preparations from individual positive clones produced very high levels of recombinant ChIFN-γ (FIG. 10). Recombinant ChIFN-γ showed the same degree of heat sensitivity (FIG. 11) and pH 2 sensitivity (data not shown) as that shown by natural ChIFN-γ.

Nucleotide sequences of several cDNA clones were determined as described in Example 7 and found to be identical. The ChIFN-γ nucleotide and derived amino acid sequences are shown in FIG. 12 and SEQ ID Nos: 1 and 2. The ChIFN-γ cDNA codes for a predicted protein of 164 amino acids with a signal peptide of 19 amino acids. The predicted mature protein is 145 amino acids in length with a molecular mass of 16.8 kD. Two potential N-glycosylation sites are predicted, the most likely site is at position 42–44, with the other at position 23–25. Like other IFN-γ proteins, ChIFN-γ contains few cysteine residues. The mature protein has only two cysteines which are located at the C-terminus (FIG. 12).

EXAMPLE 19

Comparison to mammalian IFN-γ.

Comparison of the predicted amino acid sequence of ChIFN-γ to a number of mammalian IFN-γ protein sequences revealed that although the sizes are similar, the overall level of homology is relatively low (FIG. 13). When compared to a single mammalian species the ChIFN-γ protein shows a higher degree of amino acid identity (it is 32% identical to human IFN-γ) and several highly conserved short sequences are evident (FIG. 14). ChIFN-γ shares a low degree of identity (15%) with ChIFN-α as shown in FIG. 15. Furthermore, recombinant ChIFN-γ did not protect bovine fibroblasts from virus mediated lysis and likewise bovine IFN-α and -γ failed to protect CEF (FIG. 16).

EXAMPLE 20

Expression of Class II molecules.

HD11 cells cultured in the presence of recombinant or native ChIFN-γ for 48 hr as described in Example 10 showed enhanced levels of cell surface expression of Class II molecules relative to cells grown in media alone (88% and 52% increase in expression, respectively). In contrast, the presence of another macrophage stimulator, LPS, induced only an 8% increase in Class II expression (FIG. 17).

EXAMPLE 21

Expression of recombinant ChIFN-γ in E. coli and biological function.

Recombinant ChIFN-γ (r ChIFN-γ) bearing a poly-HIS tag was expressed in E. coli using the pQE expression system and purified using a Ni affinity column (FIG. 18A). Two forms of recombinant ChIFN-γ were produced (Mr 16 and 18 kDa).

The activity of recombinant ChIFN-γ was determined using the CEF assay (Example 4), nitrite assay (Example 6) or a Turkey Embryonic Fibroblast (TEF) protection assay. Recombinant ChIFN-γ was active in the nitrite assay (FIG. 19A), in the CEF assay (FIG. 19B) and in a Turkey TEF protection assay (FIG. 19C).

The stability of recombinant ChIFN-γ was also monitored over various time intervals. Data provided in FIG. 20 indicate that recombinant ChIFN-γ is stable when stored at 4° C. or at room temperature. The inventors have shown further that recombinant ChIFN-γ can be stored for several months.

Antisera to recombinant ChIFN-γ were raised in 4 rabbits as described in Example 9. Sera from each rabbit recognised recombinant ChIFN-γ as shown by Western blots (FIG. 21). Some of these rabbit sera also inhibit the biological function of native and recombinant ChIFN-γ in vitro but did not block the function of ChIFN-β (FIG. 22).

Mice were also immunised with recombinant ChIFN-γ as described in Example 9 and there sera were found to inhibit the ability of ChIFN-γ to induce nitrite secretion by HD11 cells (FIG. 23A).

Furthermore, protein G-purified rabbit anti-recombinant ChIFN-γ antibodies also inhibit the function of recombinant ChIFN-γ (FIG. 23B).

EXAMPLE 22

Synergy between type I and type II ChIFNs

ChIFN-γ shows synergy with ChIFN-α and ChIFN-β in both the CEF and nitrite assays. CEFs were cultured in the presence of ChIFN-γ that had been serially diluted in a limiting amount of recombinant ChIFN-α. The combination of the two IFNs was up to 5 times more effective than either type of IFN alone (FIG. 24A). A similar level of synergy was shown in the nitrite assay (FIG. 24B). Native ChIFN-β was also able to synergise with ChIFN-γ (FIG. 24C).

EXAMPLE 23

ChIFN-γ as an adjuvant

Chickens were injected with SRBC (with or without recombinant ChIFN-γ) and weekly haemaglutination (HA) titres of the sera were determined as described in Example 11. Results are shown in FIG. 25. Treatment with recombinant ChIFN-γ resulted in a higher mean HA titre, a prolonged antibody response and increased the effectiveness of the low dose of antigen. This indicates that recombinant ChIFN-γ is an effective adjuvant.

EXAMPLE 24

Effect of ChIFN-γ on weight gain

One group (n=10) of one-day old SPF chickens was injected intraperitoneally with 500 Units of recombinant ChIFN-γ on 2 consecutive days and another group of control birds was injected with diluent alone. Birds were weighed over a 12 day period. Birds injected with recombinant ChIFN-γ displayed enhanced weight gain (FIGS. 26 and 27). The increase in body weight was from 5.8 to 9.0% (Table 5). These data indicate that recombinant ChIFN-γ was effective in enhancing growth performance.

EXAMPLE 25

Effect of ChIFN-γ on weight gain during infection with *E. acevurlina*

One group (n=10) of one-day old SPF chickens was injected intraperitoneally with 500 Units of recombinant ChIFN-γ on 2 consecutive days (day 0 and day 1) and another group of control birds was injected with diluent alone. All birds were infected with $5 \times 10^5$ oocytes on day 1 and then weighed over a 12 day period. Birds injected with recombinant ChIFN-γ displayed enhanced weight gain (FIGS. 28A and B). Infection with coccidiosis normally results in weight loss between day 4 and 6 of infection. Treatment with ChIFN-γ reduced the weight loss (FIG. 28C) and enhanced the rate of weight gain following natural recovery from infection (FIG. 28D). Treatment with ChIFN-γ resulted in a 7.3 to 12.5% increase in weight (Tables 6 and 7 and FIG. 29). This indicates that recombinant ChIFN-γ was effective in reducing the effect of coccidiosis on growth performance.

EXAMPLE 26

Effect of recombinant ChIFN-γ on infection with Infectious Bursal Disease Virus

SPF chickens were injected with either recombinant ChIFN-γ or diluent on 2 consecutive days and then infected with IBDV. 7 days later their bursa and whole body weights were determined as described in Example 12. Birds injected with recombinant ChIFN-γ displayed an enhanced ratio of body:bursa weight from a mean of 1.36 to 1.51 (FIG. 30), indicating that recombinant ChIFN-γ was effective in reducing virus growth in vivo.

The effect of recombinant ChIFN-γ to protect CEFs from infection with IBDV in vitro was also measured. CEFs were prepared as described for the CEF interferon assay and recombinant ChIFN-γ and IBDV were added to the cultures together. Cell survival was measured 3 days later on a scale of 0 to 4, where 0 represents the level of cell survival observed in the presence IBDV and the absence of IFN (<5% cell survival) and 4 represents the level of cell survival observed in the absence of IBDV (>90% cell survival). As shown in FIG. 31, recombinant ChIFN-γ was effective in protecting CEFs from infection with IBDV in vitro.

In conclusion, recombinant ChIFN-γ has been shown to effective in the prevention of infection by IBDV both in vivo and in vitro.

EXAMPLE 27

Discussion

Previous studies in chickens have identified only Type I IFN and cast doubts over whether chicken T cells are able to produce Type II interferon molecules.

The inventors have shown herein that chicken T cells produce the Type II interferon molecule, IFN-γ. The inventors further address the nature of T cell-derived IFN directly by generating novel chicken T cell lines that produce high levels of ChIFN-γ. Such T cell lines have not been previously reported. The presence of Type II IFN in avian species was supported herein by the surprising finding that supernatants from these T cells are capable of inducing high levels of nitrite production by macrophages, a property of IFN-γ but not IFN-α/β in mammals (Fast et al, 1993; Huang et al, 1993).

In mammals, IFN-α from different species share a high degree of homology which allows functional cross reactivity to occur between most species. Similarly, IFN-β from one species will often react with cells from another species. IFN-α and -β also share a significant degree of homology and it is likely that their genes originated from a single gene (Weissmann and Weber, 1986). In contrast, IFN-γ produced by chicken T cells fails to functionally cross react with mammalian cells. There is also only limited homology between avian IFN-γ (i.e. ChIFN-γ) and mammalian IFN-γ molecules (see below.

A chicken homologue of the mammalian Type I IFN gene has been cloned from virus-induced primary chicken embryo cells aged in vitro. ChIFN-α was shown to lack nitrite-inducing activity. Furthermore, antibodies raised to this protein failed to inhibit the nitrite-inducing activity of supernatants from ConA induced chicken spleen cell cultures.

A novel chicken T cell clone (CC8.1h) was used to clone the gene for ChIFN-γ. ChIFN-γ is unrelated to ChIFN-α. ChIFN-γ induced high levels of nitrite production by macrophages, a property of IFN-γ but not IFN-α/β in mammals. In contrast, Schultz et al (1995) recently reported that recombinant ChIFN-α could not induce the secretion of nitric oxide from chicken monocytes.

The ChIFN-γ gene codes for a predicted mature protein of 145 amino acids with a molecular mass of 16.8 kD. ChIFN-γ protein is only 35% and 32% identical to the equine and human IFN-γ molecules, respectively. A C-terminal Lys-Arg-Lys-Arg motif may represent the point of pH 2 sensitivity observed for ChIFN-γ. Furthermore, the ChIFN-γ protein shares only 15% identity with the recently reported ChIFN-α, which is similar to the level of homology found when mammalian Type I and II IFNs are compared. Furthermore, ChIFN-γ is smaller in size than ChIFN-α and contains only two rather tan seven cysteine residues.

In mammals, IFN-α proteins are highly conserved at the amino acid level, which allows functional cross reactivity to occur between a number of species. Similarly, IFN-β from one species will usually react with cells from another species. IFN-α and -β also share a significant degree of homology to each other and it is likely that their genes originated from a single ancestral gene. In cons, the level of homology between different mammalian IFN-γ proteins is relatively low and as a consequence functional activity only rarely crosses the species barrier. The degree of homology between the ChIFN-γ polypeptide and mammalian IFN-γ polypeptides is only 32–35%. ChIFN-γ does not function on cells from mammalian species. However, the inventors have demonstrated herein that ChIFN-γ does react with cells from other avian species in particular to turkey cells.

Those skilled in the art will appreciate that the invention described herein is susceptible to variations and modifications other than those specifically described. It is to be understood that the invention includes all such variations and modifications. the invention also includes all of the steps, features, compositions and compounds referred to or indicated in this specification, individually or collectively, and any and all combinations or any two or more of said steps or features.

TABLE 2

Production of IFN by chicken spleen cells and T cell clones.

Interferon titer (U/ml in CEF assay)

| Stimulus: | None | ConA | PHA | CD3 | TCR2 | TCR3 |
|---|---|---|---|---|---|---|
| Spleen[a] | <5 | 340 | 360 | 220 | 270 | 60 |
| CC4.1[b] | <5 | <5 | — | <5 | — | — |
| CC4.3[c] | 220 | 160 | — | 240 | 180 | — |
| CC8.1[b] | 480 | 640 | 640 | 560 | 480 | 640 |
| CC8.1h[d] | 2400 | 4800 | — | 3200 | 3200 | 2400 |
| CC8.1x[d] | 1800 | — | — | — | — | — |

[a]Spleen cells were cultured for 24 hr as described with or without stimulus
[b]REV transformed T cell line (CD3+, CD4+)
[c]REV transformed T cell line (CD3+, CD8+)
[d]Cloned line (from CC8.1)59

TABLE 3

Phenotype of REV-transformed chicken T cell lines.

| Cell line: | CD3[a] | CD4[a] | CD8[a] | TCR[b] | IFN[c] |
|---|---|---|---|---|---|
| CC4.1 | 97 | 48 | 25 | 2 | <5 |
| CC4.2 | 97 | 23 | 54 | 2 | 120 |
| CC4.3 | 94 | 14 | 58 | 2 | 80 |
| CC7.1 | 93 | 22 | 37 | 3 | 60 |
| CC7.2 | 98 | 29 | 45 | 2 | 120 |
| CC7.3 | 98 | 21 | 39 | 2,1 | 80 |

TABLE 3-continued

Phenotype of REV-transformed chicken T cell lines.

| Cell line: | CD3[a] | CD4[a] | CD8[a] | TCR[b] | IFN[c] |
|---|---|---|---|---|---|
| CC8.1 | 97 | 81 | 4 | 2,3 | 160 |
| CC8.1x[d] | 95 | nd | nd | nd | 320 |
| CC8.1h[e] | 0 | 0 | 0 | nd | 320 |
| CC8.1x[e] | 0 | 0 | 0 | nd | 280 |
| Spleen[f] | 60 | 18 | 45 | 2 | <5 |

[a]Percent of cells positive for surface marker
[b]Predominant phenotype of T cell receptor (TCR1,2,3)
[c]IFN titer of supernatant (Nitrite assay, U/ml)
[d]Cloned from CC8.1 and analyzed 7 days post cloning
[e]Cloned from CC8.1 and analyzed 4 weeks post cloning
[f]Spleen leukocytes from a 6 week old chicken

TABLE 4

Relationship between IFN titers measured by CEF assay versus nitrite assay

| | CEF[a] | Nitrite[b] | CEF:Nitrite[c] |
|---|---|---|---|
| CC8.1h | 3200[d] | 640 | 5 |
| CEF | 4800 | 10 | 480 |

[a]IFN titer measured by the CEF assay
[b]IFN titer measured by the nitrite assay
[c]Ratio of CEF titer to nitrite-inducing titer
[d]IFN (U/ml)

TABLE 5

Effect of recombinant ChIFN-γ on weight gain in broilers.

Body weight (g)[a]

| Day | recombinant ChIFN-γ[b] | Control[c] | % Increase |
|---|---|---|---|
| 3 | 154.0 ± 18 | 143.5 ± 24 | 7.3 |
| 4 | 204.9 ± 23 | 188.2 ± 35 | 9.0 |
| 5 | 235.4 ± 26 | 217.0 ± 40 | 8.5 |
| 6 | 262.3 ± 28 | 244.3 ± 47 | 7.4 |
| 7 | 290.1 ± 30 | 269.5 ± 49 | 7.6 |
| 10 | 390.8 ± 39 | 360.1 ± 62 | 8.6 |
| 12 | 475.6 ± 43 | 449.5 ± 75 | 5.8 |

[a]Mean weight of chickens (n = 10) ± standard deviation
[b]Birds injected intra peritoneal with 500 U of recombinant ChIFN-γ on days 0 and 1
[c]Birds injected intra peritoneal with diluent on days 0 and 1

TABLE 6

Effect of recombinant ChIFN-γ on weight gain in broilers following infection with E. acervulina.

Body weight (g)[a]

| Day | recombinant ChIFN-γ[b] | Control[c] | % Increase |
|---|---|---|---|
| 4 | 198.7 ± 26 | 185.1 ± 30 | 7.3 |
| 5 | 195.2 ± 26 | 176.8 ± 29 | 10.2 |
| 6 | 202.2 ± 23 | 185.4 ± 31 | 9.1 |
| 8 | 248.4 ± 35 | 220.9 ± 42 | 12.5 |
| 11 | 353.6 ± 52 | 315.6 ± 56 | 12.0 |

[a]Mean weight of chickens (n = 10) ± standard deviation
[b]Birds injected intra peritoneal with 500 U of recombinant ChIFN-γ on days 0 and 1 and infected with 5 × 10^5 oocysts on day 1
[c]Birds injected intra peritoneal with diluent on days 0 and 1 and infected with 5 × 10^5 oocysts on day 1

TABLE 7

Effect of recombinant ChIFN-γ on weight gain in broilers following infection with *E. acervulina*.

| | Body weight (g) | | |
|---|---|---|---|
| Day | recombinant ChIFN-γ[b] | Control[c] | Increase (g)[d] |
| 1–4 | 52.0[a] | 52.1 | −0.1 |
| 4–5 | −3.5 | −8.3 | 4.8 |
| 5–6 | 7.0 | 8.6 | −1.6 |
| 6–8 | 46.2 | 35.5 | 10.7 |
| 8–11 | 105.2 | 94.7 | 10.5 |
| 1–11 | 206.9 | 182.6 | 24.3 |

[a]Mean weight gain of chickens (n = 10) ± standard deviation between the indicated days
[b]Birds injected intra peritoneal with 500 U of recombinant ChIFN-γ on days 0 and 1 and infected with 5 × 10$^5$ oocysts on day 1
[c]Birds injected intra peritoneal with diluent on days 0 and 1 and infected with 5 × 10$^5$ oocysts on day 1
[d]Increase in body weight due to recombinant ChIFN-γ

REFERENCES

1. Amann and Brosius (1985). *Gene* 40, 183
2. Ausubel, F. M. et al. (1987) In: Current Protocols in Molecular Biology, Wiley Interscience (ISBN 047140338).
3. Beug, H. et al (1979). *Cell* 18, 375–390.
4. Digby, M. R. and Lowenthal, J. W. (1995). *J. Interferon Cytokine Res.* 15, 939–945.
5. Dijkmans, R. et al (1990). *Vet. Immunol. Immunopathol.* 26, 319–332.
6. Fast, D. J. et al (1993). *J. Interferon Res.* 13. 271–277.
7. Huang, S. et al (1993). *Science* 259, 1742–1745.
8. Lillehoj, H. S. et al (1992). *Poult. Sci. Rev.* 4, 67–85.
9. Lowenthal, J. W. et al (1993). *Immunol. Cell Biol.* 115–122.
10. Lowenthal, J. W. et al (1995a). In: Advances in Avian Immunology Research. (Eds. Davison T. F., Bumstead N. and Kaiser P.) Carfax, Oxford. 179–186.
11. Lowenthal, J. W. et al (1995b). *J. Interferon Cytokine Res.* 15, 933–938.
12. Prowse, S. J. and Pallister, J. (1989). *Avian Pathol.* 18, 619–630.
13. Pusztai, R. et al (1986). *Acta Virol.*, 30, 131–136.
14. Sambrook, J. et al (1989). In: Molecular Cloning: A Laboratory Manual. Cold Spring Harbor Laboratory Press.
15. Schultz, U. et al (1995). *Eur. J. Immunol.* 25, 847–851.
16. Sekellick, M. J. and Marcus, P. I. (1986). *Methods Enzymol.* 119, 115–125.
17. Sekellick, M. J. et al (1994). *J. Interferon Res.* 14, 71–79.
18. Shimatake and Rosenberg (1981) *Nature* 292, 128
19. Studier and Moffat (1986) *J. Mol. Biol.* 189, 113
20. Sung, Y.-J. et al (1991). *J. Leukocyte Biol.* 50, 49–56.
21. Thacore, H. R. et al (1985). *Interferon Res.* 5, 279–288.
22. Von Bulow, V. et al (1984). *Avian Pathol.* 13, 621–637.
23. Weiler, H. and Von Bulow, V. (1987). *Avian Pathol* 16, 439–452.
24. Weissmann, C., and Weber, H. (1986). *Prog. Nucleic Acid Res.* 33, 251–300.

---

We claim:

1. An isolated nucleic acid molecule encoding an avian interferon-γ (IFN-γ) polypeptide, wherein the nucleic acid molecule has a nucleotide sequence selected from the group consisting of:
   (a) the sequence of a DNA molecule present in an avian DNA library, wherein said DNA molecule hybridizes under conditions of at least moderate stringency with a probe having a sequence complementary to at least 50 contiguous nucleotides of SEQ ID NO:1; and
   (b) a nucleotide sequence that is degenerate with a DNA molecule according to (a).

2. The isolated nucleic acid molecule according to claim 1, wherein said avian DNA library is prepared from a species of poultry.

3. The isolated nucleic acid molecule according to claim 1, wherein said DNA molecule hybridizes with said probe under conditions of high stringency.

4. An isolated nucleic acid molecule comprising at least 50 contiguous nucleotides of SEQ ID NO:1.

5. The isolated nucleic acid molecule according to claim 4 comprising a fragment of SEQ ID NO:1 which encodes at least 10 contiguous amino acids of SEQ ID NO:2.

6. An isolated nucleic acid molecule comprising a nucleotide sequence which encodes at least 10 contiguous amino acids of SEQ ID NO:2.

7. An isolated nucleic acid molecule comprising a nucleotide sequence which encodes at least 20 contiguous amino acids of SEQ ID NO:2.

8. An isolated nucleic acid molecule having a nucleotide sequence which encodes the amino acid sequence of SEQ ID NO:2 or the mature protein region thereof.

9. An isolated nucleic acid molecule encoding an avian interferon-γ (IFN-γ) and comprising the nucleotide sequence of the protein-encoding region of SEQ ID NO:1 or a nucleotide sequence that is degenerate with the nucleotide sequence of the protein-encoding region of SEQ ID NO:1.

10. A genetic construct or viral vector comprising a nucleic acid molecule encoding an avian interferon-γ (IFN-γ) polypeptide operably linked to a promoter sequence, wherein the nucleic acid molecule has a nucleotide sequence selected from the group consisting of:
   (a) the sequence of a DNA molecule present in an avian DNA library, wherein said DNA molecule hybridizes under conditions of at least moderate stringency with a probe having a sequence complementary to at least 50 contiguous nucleotides of SEQ ID No:1; and
   (b) a nucleotide sequence that is degenerate with a DNA molecule according to (a).

11. A genetic construct or viral vector comprising the nucleotide sequence of the protein-encoding region of SEQ ID NO:1 or a nucleotide sequence that is degenerate with the nucleotide sequence of the protein-encoding region of SEQ ID No:1 operably linked to a promoter sequence.

12. The genetic construct according to claim 11 designated pQE ChIFN-γ.

13. The genetic construct according to claim 11 designated pCDNA3/avian G-IFN.

14. An isolated avian IFN-γ cytokine polypeptide comprising the amino acid sequence set forth as the mature protein region of SEQ ID NO:2.

15. A method of producing an avian IFN-γ cytokine polypeptide in a cell comprising expressing in said cell, for a time and under conditions sufficient for protein synthesis to occur, heterologous DNA having a nucleotide sequence selected from the group consisting of:
   (a) the sequence of a DNA molecule present in an avian DNA library, wherein said DNA molecule hybridizes under conditions of at least moderate stringency with a probe having a sequence complementary to at least 50 contiguous nucleotides of SEQ ID NO:1; and
   (b) a nucleotide sequence that is degenerate with a DNA molecule according to (a).

16. The method according to claim 15 further comprising introducing into said cell a genetic construct or viral vector containing said nucleotide sequence.

17. The method according to claim 15 further comprising isolating the expressed avian IFN-γ polypeptide from said cell.

18. The CC8.1h cell line deposited under AGAL Accession No. N94/46035 which expresses an avian IFN-γ cytokine polypeptide.

19. A COS cell or cell line which expresses an avian IFN-γ cytokine polypeptide wherein said COS cell or cell line contains the pCDNA3/avian G-IFN plasmid deposited under AGAL Accession No. N95/12388.

20. The *E. coli* strain pOE ChIFN-γ deposited under AGAL Accession No. N96/9464.

21. A cell transformed, transfected, or infected with a genetic construct or viral vector that comprises a nucleic acid molecule encoding an avian interferon-γ (IFN-γ) polypeptide, wherein the nucleic acid molecule has a nucleotide sequence selected from the group comprising:
   (a) the sequence of a DNA molecule present in an avian DNA library, wherein said DNA molecule hybridizes under conditions of at least moderate stringency with a probe having a sequence complementary to at least 50 contiguous nucleotides of SEQ ID NO:1; and
   (b) a nucleotide sequence that is degenerate with a DNA molecule according to (a).

22. A cell according to claim 21 wherein the nucleic acid molecule encodes an avian IFN-γ polypeptide other than a native IFN-γ polypeptide.

23. A cell according to claim 21 wherein the nucleic acid molecule encodes an avian IFN-γ cytokine polypeptide comprising the amino acid sequence set forth as the mature protein region of SEQ ID NO:2.

24. An adjuvant comprising an immunogenicity-enhancing amount of an avian IFN-γ cytokine polypeptide comprising the amino acid sequence set forth as the mature protein region of SEQ ID NO:2 and a pharmaceutically acceptable carrier, excipient, or diluent.

25. The adjuvant according to claim 24 further comprising a native avian type I IFN polypeptide.

26. The adjuvant according to claim 24 further comprising a native avian IFN-α polypeptide.

27. The adjuvant according to claim 24 in a form suitable for ingestion by a poultry species.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 1079 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Chicken (Gallus sp.)
      (G) CELL TYPE: T-cell
      (H) CELL LINE: CC8.1h (vii) IMMEDIATE SOURCE:
      (A) LIBRARY: CC8.1h
      (B) CLONE: ChIFN-gamma (ix) FEATURE:
      (A) NAME/KEY: CDS
      (B) LOCATION: 134..625

(ix) FEATURE:
      (A) NAME/KEY: mat_peptide
      (B) LOCATION: 191..625

(ix) FEATURE:

(A) NAME/KEY: 5'UTR
        (B) LOCATION: 1..133

(ix) FEATURE:
        (A) NAME/KEY: 3'UTR
        (B) LOCATION: 626..1079

(xi) SEQUENCE DESCRIPTION: SEQ ID NO:1:

```
GGATCCACTA GTAACGGCCG CCAGTGTGGT GGAATTCAGA AGACATAACT ATTAGAAGCT      60

GAAGCTCACT GAGCTTATAT CTGACATCTC CCAGAAGCTA TCTGAGCATT TGAACTGAGC     120

CATCACCAAG AAG ATG ACT TGC CAG ACT TAC AAC TTG TTT GTT CTG TCT        169
            Met Thr Cys Gln Thr Tyr Asn Leu Phe Val Leu Ser
            -19             -15                 -10

GTC ATC ATG ATT TAT TAT GGA CAT ACT GCA AGT AGT CTA AAT CTT GTT        217
Val Ile Met Ile Tyr Tyr Gly His Thr Ala Ser Ser Leu Asn Leu Val
        -5              1               5

CAA CTT CAA GAT GAT ATA GAC AAA CTG AAA GCT GAC TTT AAC TCA AGT        265
Gln Leu Gln Asp Asp Ile Asp Lys Leu Lys Ala Asp Phe Asn Ser Ser
 10              15              20              25

CAT TCA GAT GTA GCT GAC GGT GGA CCT ATT ATT GTA GAG AAA CTG AAG        313
His Ser Asp Val Ala Asp Gly Gly Pro Ile Ile Val Glu Lys Leu Lys
             30              35              40

AAC TGG ACA GAG AGA AAT GAG AAA AGG ATC ATA CTG AGC CAG ATT GTT        361
Asn Trp Thr Glu Arg Asn Glu Lys Arg Ile Ile Leu Ser Gln Ile Val
         45              50              55

TCG ATG TAC TTG GAA ATG CTT GAA AAC ACT GAC AAG TCA AAG CCG CAC        409
Ser Met Tyr Leu Glu Met Leu Glu Asn Thr Asp Lys Ser Lys Pro His
         60              65              70

ATC AAA CAC ATA TCT GAG GAG CTC TAT ACT CTG AAA AAC AAC CTT CCT        457
Ile Lys His Ile Ser Glu Glu Leu Tyr Thr Leu Lys Asn Asn Leu Pro
 75              80              85

GAT GGC GTG AAG AAG GTG AAA GAT ATC ATG GAC CTG GCC AAG CTC CCG        505
Asp Gly Val Lys Lys Val Lys Asp Ile Met Asp Leu Ala Lys Leu Pro
 90              95              100             105

ATG AAC GAC TTG AGA ATC CAG CGC AAA GCC GCG AAT GAA CTC TTC AGC        553
Met Asn Asp Leu Arg Ile Gln Arg Lys Ala Ala Asn Glu Leu Phe Ser
             110             115             120

ATC TTA CAG AAG CTG GTG GAT CCT CCG AGT TTC AAA AGG AAA AGG AGC        601
Ile Leu Gln Lys Leu Val Asp Pro Pro Ser Phe Lys Arg Lys Arg Ser
             125             130             135

CAG TCT CAG AGG AGA TGC AAT TGC TAATGGCATC TTATGACCTC CTGTGCTCAA       655
Gln Ser Gln Arg Arg Cys Asn Cys
             140             145

CTATTTTAAA TTTTACAATG CACAATTTTT ATGTTGTGAT TTTTTAACTG AGTTTATATA      715

CATTTATTTA TTAATATTTA AGTATTTTAA ATAATTATTT ATATTAAAAA AAAACCAGGC      775

AAACAATGAA AGTATTTATA CCTCCTACTG CTGTGTAAGA AACGGATTGT GGTCTTAAAA      835

TACTGTCTAT CTGTTGTGTG TGGGTTGACT GAAAATACCG AATGAGGTGG ATGTTTACCA      895

GTTTCTGTGT GGGAAATACT GAATTGGAGG TGGATCTGTA CTCAAGAAAA CCCACTCATC      955

CCGGTCAGTC TAGTATTTCT AAATCCAAAT CAAGGAGTGG CTTGTTTAAA GGGAAAAAAT     1015

GTGAGCACTC TCTGACTGGG TCTTAGAGAT TTTACTGATG GTTTGGCATG ACTAAGAATT     1075

TAGG                                                                  1079
```

(2) INFORMATION FOR SEQ ID NO:2:

(i) SEQUENCE CHARACTERISTICS:
        (A) LENGTH: 164 amino acids
        (B) TYPE: amino acid (D) TOPOLOGY: linear (ii) MOLECULE TYPE: protein (xi) SEQUENCE DESCRIPTION: SEQ ID NO:2:

Met Thr Cys Gln Thr Tyr Asn Leu Phe Val Leu Ser Val Ile Met Ile
-19             -15                 -10                 -5

Tyr Tyr Gly His Thr Ala Ser Ser Leu Asn Leu Val Gln Leu Gln Asp
             1              5                  10

Asp Ile Asp Lys Leu Lys Ala Asp Phe Asn Ser Ser His Ser Asp Val
         15              20                  25

Ala Asp Gly Gly Pro Ile Ile Val Glu Lys Leu Lys Asn Trp Thr Glu
         30              35              40                  45

Arg Asn Glu Lys Arg Ile Ile Leu Ser Gln Ile Val Ser Met Tyr Leu
                 50              55                  60

Glu Met Leu Glu Asn Thr Asp Lys Ser Lys Pro His Ile Lys His Ile
             65              70                  75

Ser Glu Glu Leu Tyr Thr Leu Lys Asn Asn Leu Pro Asp Gly Val Lys
             80              85              90

Lys Val Lys Asp Ile Met Asp Leu Ala Lys Leu Pro Met Asn Asp Leu
         95              100             105

Arg Ile Gln Arg Lys Ala Ala Asn Glu Leu Phe Ser Ile Leu Gln Lys
110             115             120                 125

Leu Val Asp Pro Pro Ser Phe Lys Arg Lys Arg Ser Gln Ser Gln Arg
             130             135             140

Arg Cys Asn Cys
             145

(2) INFORMATION FOR SEQ ID NO:3:

(i) SEQUENCE CHARACTERISTICS:
        (A) LENGTH: 1042 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Chicken (Gallus sp.)

(ix) FEATURE:
        (A) NAME/KEY: CDS
        (B) LOCATION: 97..588

(xi) SEQUENCE DESCRIPTION: SEQ ID NO:3:

AGAAGACATA ACTATTAGAA GCTGAAGCTC ACTGAGCTTA TATCTGACAT CTCCCAGAAG        60

CTATCTGAGC ATTTGAACTG AGCCATCACC AAGAAG ATG ACT TGC CAG ACT TAC        114
                                        Met Thr Cys Gln Thr Tyr
                                         1               5

AAC TTG TTT GTT CTG TCT GTC ATC ATG ATT TAT TAT GGA CAT ACT GCA        162
Asn Leu Phe Val Leu Ser Val Ile Met Ile Tyr Tyr Gly His Thr Ala
             10                  15                  20

AGT AGT CTA AAT CTT GTT CAA CTT CAA GAT GAT ATA GAC AAA CTG AAA        210
Ser Ser Leu Asn Leu Val Gln Leu Gln Asp Asp Ile Asp Lys Leu Lys
         25                  30                  35

GCT GAC TTT AAC TCA AGT CAT TCA GAT GTA GCT GAC GGT GGA CCT ATT        258
Ala Asp Phe Asn Ser Ser His Ser Asp Val Ala Asp Gly Gly Pro Ile

```
                40                      45                      50
ATT GTA GAG AAA CTG AAG AAC TGG ACA GAG AGA AAT GAG AAA AGG ATC      306
Ile Val Glu Lys Leu Lys Asn Trp Thr Glu Arg Asn Glu Lys Arg Ile
 55                      60                      65                      70

ATA CTG AGC CAG ATT GTT TCG ATG TAC TTG GAA ATG CTT GAA AAC ACT      354
Ile Leu Ser Gln Ile Val Ser Met Tyr Leu Glu Met Leu Glu Asn Thr
             75                      80                      85

GAC AAG TCA AAG CCG CAC ATC AAA CAC ATA TCT GAG GAG CTC TAT ACT      402
Asp Lys Ser Lys Pro His Ile Lys His Ile Ser Glu Glu Leu Tyr Thr
                 90                      95                     100

CTG AAA AAC AAC CTT CCT GAT GGC GTG AAG AAG GTG AAA GAT ATC ATG      450
Leu Lys Asn Asn Leu Pro Asp Gly Val Lys Lys Val Lys Asp Ile Met
            105                     110                     115

GAC CTG GCC AAG CTC CCG ATG AAC GAC TTG AGA ATC CAG CGC AAA GCC      498
Asp Leu Ala Lys Leu Pro Met Asn Asp Leu Arg Ile Gln Arg Lys Ala
                120                     125                     130

GCG AAT GAA CTC TTC AGC ATC TTA CAG AAG CTG GTG GAT CCT CCG AGT      546
Ala Asn Glu Leu Phe Ser Ile Leu Gln Lys Leu Val Asp Pro Pro Ser
135                     140                     145                     150

TTC AAA AGG AAA AGG AGC CAG TCT CAG AGG AGA TGC AAT TGC              588
Phe Lys Arg Lys Arg Ser Gln Ser Gln Arg Arg Cys Asn Cys
                    155                     160

TAATGGCATC TTATGACCTC CTGTGCTCAA CTATTTTAAA TTTTACAATG CACAATTTTT    648

ATGTTGTGAT TTTTTAACTG AGTTTATATA CATTTATTTA TTAATATTTA AGTATTTTAA    708

ATAATTATTT ATATTAAAAA AAAACCAGGC AAACAATGAA AGTATTTATA CCTCCTACTG    768

CTGTGTAAGA AACGGATTGT GGTCTTAAAA TACTGTCTAT CTGTTGTGTG TGGGTTGACT    828

GAAAATACCG AATGAGGTGG ATGTTTACCA GTTTCTGTGT GGGAAATACT GAATTGGAGG    888

TGGATCTGTA CTCAAGAAAA CCCACTCATC CCGGTCAGTC TAGTATTTCT AAATCCAAAT    948

CAAGGAGTGG CTTGTTTAAA GGGAAAAAAT GTGAGCACTC TCTGACTGGG TCTTAGAGAT   1008

TTTACTGATG GTTTGGCATG ACTAAGAATT TAGG                              1042

(2) INFORMATION FOR SEQ ID NO:4:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: bovine (xi) SEQUENCE DESCRIPTION: SEQ ID NO:4:

Met Lys Tyr Thr Ser Tyr Phe Leu Ala Leu Leu Cys Gly Leu Leu
 1               5                  10                  15

Gly Phe Ser Gly Ser Tyr Gly Gln Gly Gln Phe Phe Arg Glu Ile Glu
                20                  25                  30

Asn Leu Lys Glu Tyr Phe Asn Ala Ser Ser Pro Asp Val Ala Lys Gly
            35                  40                  45

Gly Pro Leu Phe Ser Glu Ile Leu Lys Asn Trp Lys Asp Glu Ser Asp
        50                  55                  60

Lys Lys Ile Ile Gln Ser Gln Ile Val Ser Phe Tyr Phe Lys Leu Phe
65                  70                  75                  80
```

```
Glu Asn Leu Lys Asp Asn Gln Val Ile Gln Arg Ser Met Asp Ile Ile
                 85                  90                  95

Lys Gln Asp Met Phe Gln Lys Phe Leu Asn Gly Ser Ser Glu Lys Leu
            100                 105                 110

Glu Asp Phe Lys Lys Leu Ile Gln Ile Pro Val Asp Asp Leu Gln Ile
        115                 120                 125

Gln Arg Lys Ala Ile Asn Glu Leu Ile Lys Val Met Asn Asp Leu Ser
    130                 135                 140

Pro Lys Ser Asn Leu Arg Lys Arg Lys Arg Ser Gln Asn Leu Phe Arg
145                 150                 155                 160

Gly Arg Arg Ala Ser Thr
                165
```

(2) INFORMATION FOR SEQ ID NO:5:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: non-human primate (xi) SEQUENCE DESCRIPTION: SEQ ID NO:5:

```
Met Lys Tyr Thr Ser Tyr Ile Leu Ala Phe Gln Leu Cys Val Val Leu
1                5                  10                  15

Gly Ser Leu Gly Cys Tyr Cys Gln Asp Pro Tyr Val Lys Glu Ala Glu
                 20                  25                  30

Asn Leu Lys Lys Tyr Phe Asn Ala Gly Asp Ser Asp Val Ala Asp Asn
            35                  40                  45

Gly Thr Leu Phe Leu Asp Ile Leu Arg Thr Trp Arg Glu Glu Gly Asp
        50                  55                  60

Arg Lys Ile Met Gln Ser Gln Ile Ile Ser Phe Tyr Phe Lys Leu Phe
65                  70                  75                  80

Lys Asn Phe Lys Asp Asn Gln Ser Ile Gln Lys Ser Met Glu Thr Ile
                85                  90                  95

Lys Glu Asp Met Asn Val Lys Phe Phe Asn Ser Asn Lys Arg Lys Gln
            100                 105                 110

Asp Asp Phe Glu Arg Leu Thr Asn Tyr Ser Val Asn Asp Leu Asn Val
        115                 120                 125

Gln Arg Lys Ala Ile His Glu Leu Ile Gln Val Met Ala Glu Leu Ser
    130                 135                 140

Pro Ala Pro Lys Ile Gly Lys Arg Arg Arg Ser Gln Thr Leu Phe Arg
145                 150                 155                 160

Gly Arg Arg Ala Ser Gln
                165
```

(2) INFORMATION FOR SEQ ID NO:6:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
    (A) ORGANISM: non-human primate (xi) SEQUENCE DESCRIPTION: SEQ ID NO:6:

```
Met Lys Tyr Thr Ser Tyr Ile Leu Ala Leu Gln Leu Cys Val Leu Leu
1               5                   10                  15

Gly Phe Ser Gly Ser Tyr Gly Gln Gly Pro Phe Lys Glu Ile Glu
            20                  25                  30

Asn Leu Lys Glu Tyr Phe Asn Ala Ser Asn Pro Asp Val Ala Glu Gly
                35                  40                  45

Gly Pro Leu Phe Ile Glu Ile Leu Lys Asn Trp Lys Glu Glu Ser Asp
        50                  55                  60

Arg Lys Ile Ile Gln Ser Gln Ile Val Ser Phe Tyr Phe Lys Leu Phe
65                  70                  75                  80

Glu Asn Phe Lys Asp Asn Gln Val Ile Gln Arg Ser Val Asp Ile Ile
                85                  90                  95

Lys Gln Asp Met Phe Gln Lys Phe Leu Asn Gly Ser Ser Glu Lys Leu
                100                 105                 110

Glu Asp Phe Lys Lys Leu Ile Gln Ile Ser Val Asp Asp Met Gln Ile
            115                 120                 125

Gln Arg Lys Ala Ile Asn Glu Leu Ile Lys Val Met Asn Asp Leu Ser
    130                 135                 140

Pro Lys Ser Asn Leu Ile Lys Arg Lys Arg Ser Gln Asn Leu Phe Arg
145                 150                 155                 160

Gly Arg Arg Ala Ser Met
                165
```

(2) INFORMATION FOR SEQ ID NO:7:

(i) SEQUENCE CHARACTERISTICS:
        (A) LENGTH: 149 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: canine (xi) SEQUENCE DESCRIPTION: SEQ ID NO:7:

```
Ser Leu Gly Cys Tyr Cys Gln Ala Met Phe Phe Lys Glu Ile Glu Asn
1               5                   10                  15

Leu Lys Glu Tyr Phe Asn Ala Ser Asn Pro Asp Val Ser Asp Gly Gly
            20                  25                  30

Ser Leu Phe Val Asp Ile Leu Lys Lys Trp Arg Glu Glu Ser Asp Lys
        35                  40                  45

Thr Ile Ile Gln Ser Gln Ile Val Ser Phe Tyr Leu Lys Leu Phe Asp
    50                  55                  60

Asn Phe Lys Asp Asn Gln Ile Ile Gln Arg Met Ser Asp Thr Ile Lys
65                  70                  75                  80

Glu Asp Met Leu Gly Lys Phe Leu Asn Ser Ser Thr Ser Lys Arg Glu
                85                  90                  95

Asp Phe Leu Lys Leu Ile Gln Ile Pro Val Asn Asp Leu Gln Val Gln
                100                 105                 110
```

Arg Lys Ala Ile Asn Glu Leu Ile Lys Val Met Asn Asp Leu Ser Pro
            115                 120                 125

Arg Ser Asn Leu Arg Lys Arg Lys Arg Ser Gln Asn Leu Phe Arg Gly
        130                 135                 140

Arg Arg Ala Ser Lys
145

(2) INFORMATION FOR SEQ ID NO:8:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: human (xi) SEQUENCE DESCRIPTION: SEQ ID NO:8:

Met Lys Tyr Thr Ser Tyr Ile Leu Ala Phe Gln Leu Cys Ile Val Leu
1                5                  10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Gln
145                 150                 155                 160

Gly Arg Arg Ala Ser Gln
                165

(2) INFORMATION FOR SEQ ID NO:9:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: murine (xi) SEQUENCE DESCRIPTION: SEQ ID NO:9:

```
Met Asn Ala Thr His Cys Ile Leu Ala Leu Gln Leu Phe Leu Met Ala
1               5                   10                  15

Val Ser Gly Cys Tyr Cys His Gly Thr Val Ile Glu Ser Leu Glu Ser
            20                  25                  30

Leu Asn Asn Tyr Phe Asn Ser Ser Gly Ile Asp Val Glu Glu Lys Ser
        35                  40                  45

Leu Phe Leu Asp Ile Trp Arg Asn Trp Gln Lys Asp Gly Asp Met Lys
    50                  55                  60

Ile Leu Gln Ser Gln Ile Ile Ser Phe Tyr Leu Arg Leu Phe Glu Val
65                  70                  75                  80

Leu Lys Asp Asn Gln Ala Ile Ser Asn Asn Ile Ser Val Ile Glu Ser
                85                  90                  95

His Leu Ile Thr Thr Phe Phe Ser Asn Ser Lys Ala Lys Lys Asp Ala
                100                 105                 110

Phe Met Ser Ile Ala Lys Phe Glu Val Asn Asn Pro Gln Val Gln Arg
            115                 120                 125

Gln Ala Phe Asn Glu Leu Ile Arg Val Val His Gln Leu Leu Pro Glu
        130                 135                 140

Ser Ser Leu Arg Lys Arg Lys Arg Ser Arg Cys
145                 150                 155

(2) INFORMATION FOR SEQ ID NO:10:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: porcine (xi) SEQUENCE DESCRIPTION: SEQ ID NO:10:

Met Ser Tyr Thr Thr Tyr Phe Leu Ala Phe Gln Leu Cys Val Thr Leu
1               5                   10                  15

Cys Phe Ser Gly Ser Tyr Cys Gln Ala Pro Phe Phe Lys Glu Ile Thr
            20                  25                  30

Ile Leu Lys Asp Tyr Phe Asn Ala Ser Thr Ser Asp Val Pro Asn Gly
        35                  40                  45

Gly Pro Leu Phe Leu Glu Ile Leu Lys Asn Trp Lys Glu Glu Ser Asp
    50                  55                  60

Lys Lys Ile Ile Gln Ser Gln Ile Val Ser Phe Tyr Phe Lys Phe Phe
65                  70                  75                  80

Glu Ile Phe Lys Asp Asn Gln Ala Ile Gln Arg Ser Met Asp Val Ile
                85                  90                  95

Lys Gln Asp Met Phe Gln Arg Phe Leu Asn Gly Ser Ser Gly Lys Leu
                100                 105                 110

Asn Asp Phe Glu Lys Leu Ile Lys Ile Pro Val Asp Asn Leu Gln Ile
            115                 120                 125

Gln Arg Lys Ala Ile Ser Glu Leu Ile Lys Val Met Asn Asp Leu Ser
        130                 135                 140

Pro Arg Ser Asn Leu Arg Lys Arg Lys Arg Ser Gln Thr Met Phe Gln
145                 150                 155                 160

Gly Gln Arg Ala Ser Lys
```

165

(2) INFORMATION FOR SEQ ID NO:11:

(i) SEQUENCE CHARACTERISTICS:
        (A) LENGTH: 156 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: rattus ssp.

(xi) SEQUENCE DESCRIPTION: SEQ ID NO:11:

```
Met Ser Ala Thr Arg Arg Val Leu Val Leu Gln Leu Cys Leu Met Ala
1               5                   10                  15

Leu Ser Gly Cys Tyr Cys Gln Gly Thr Leu Ile Glu Ser Leu Glu Ser
            20                  25                  30

Leu Lys Asn Tyr Phe Asn Ser Ser Met Asp Ala Met Glu Gly Lys
        35                  40                  45

Ser Leu Leu Leu Asp Ile Trp Arg Asn Trp Gln Lys Asp Gly Asn Thr
50                  55                  60

Lys Ile Leu Glu Ser Gln Ile Ile Ser Phe Tyr Leu Arg Leu Phe Glu
65                  70                  75                  80

Val Leu Lys Asp Asn Gln Ala Ile Ser Asn Asn Ile Ser Val Ile Glu
                85                  90                  95

Ser His Leu Ile Thr Asn Phe Ser Asn Ser Lys Ala Lys Lys Asp
                100                 105                 110

Ala Phe Met Ser Ile Ala Lys Phe Glu Val Asn Asn Pro Gln Ile Gln
            115                 120                 125

His Lys Ala Val Asn Glu Leu Ile Arg Val Ile His Gln Leu Ser Pro
        130                 135                 140

Glu Ser Ser Leu Arg Lys Arg Lys Arg Ser Arg Cys
145                 150                 155
```

(2) INFORMATION FOR SEQ ID NO:12:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: ovine (xi) SEQUENCE DESCRIPTION: SEQ ID NO:12:

```
Met Lys Tyr Thr Ser Ser Phe Leu Ala Leu Leu Leu Cys Val Leu Leu
1               5                   10                  15

Gly Phe Ser Gly Ser Tyr Gly Gln Gly Pro Phe Phe Lys Glu Ile Glu
            20                  25                  30

Asn Leu Lys Glu Tyr Phe Asn Ala Ser Asn Pro Asp Val Ala Lys Gly
        35                  40                  45

Gly Pro Leu Phe Ser Glu Ile Leu Lys Asn Trp Lys Glu Glu Ser Asp
50                  55                  60
```

```
Lys Lys Ile Ile Gln Ser Gln Ile Val Ser Phe Tyr Phe Lys Leu Phe
65                  70                  75                  80

Glu Asn Leu Lys Asp Asn Gln Val Ile Gln Arg Ser Met Asp Ile Ile
                85                  90                  95

Lys Gln Asp Met Phe Gln Lys Phe Leu Asn Gly Ser Ser Glu Lys Leu
            100                 105                 110

Glu Asp Phe Lys Arg Leu Ile Gln Ile Pro Val Asp Asp Leu Gln Ile
        115                 120                 125

Gln Arg Lys Ala Ile Asn Glu Leu Ile Lys Val Met Asn Asp Leu Ser
    130                 135                 140

Pro Lys Ser Asn Leu Arg Lys Arg Lys Arg Ser Gln Asn Leu Phe Arg
145                 150                 155                 160

Gly Arg Arg Ala Ser Met
                165
```

(2) INFORMATION FOR SEQ ID NO:13:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: equine (xi) SEQUENCE DESCRIPTION: SEQ ID NO:13:

```
Met Asn Tyr Thr Ser Phe Ile Leu Ala Phe Gln Leu Cys Ala Ile Leu
1               5                   10                  15

Gly Ser Ser Thr Tyr Tyr Cys Gln Ala Ala Phe Phe Lys Glu Ile Glu
                20                  25                  30

Asn Leu Lys Glu Tyr Phe Asn Ala Ser Asn Pro Asp Val Gly Asp Gly
            35                  40                  45

Gly Pro Leu Phe Leu Asp Ile Leu Lys Asn Trp Lys Glu Asp Ser Asp
50                  55                  60

Lys Lys Ile Ile Gln Ser Gln Ile Val Ser Phe Tyr Phe Lys Leu Phe
65                  70                  75                  80

Glu Asn Leu Lys Asp Asn Gln Val Ile Gln Lys Ser Met Asp Thr Ile
                85                  90                  95

Lys Glu Asp Leu Phe Val Lys Phe Phe Asn Ser Ser Thr Ser Lys Leu
            100                 105                 110

Glu Asp Phe Gln Lys Leu Ile Gln Ile Pro Val Asn Asp Leu Lys Val
        115                 120                 125

Gln Arg Lys Ala Ile Ser Glu Leu Ile Lys Val Met Asn Asp Leu Ser
    130                 135                 140

Pro Lys Ala Asn Leu Arg Lys Arg Lys Arg Ser Gln Asn Pro Phe Arg
145                 150                 155                 160

Gly Arg Arg Ala Leu Gln
                165
```

(2) INFORMATION FOR SEQ ID NO:14:

(i) SEQUENCE CHARACTERISTICS:
        (A) LENGTH: 166 amino acids
        (B) TYPE: amino acid (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: human (xi) SEQUENCE DESCRIPTION: SEQ ID NO:14:

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
                100                 105                 110

Asp Asp Phe Glu Lys Leu Thr Asn Tyr Ser Val Thr Asp Leu Asn Val
            115                 120                 125

Gln Arg Lys Ala Ile His Glu Leu Ile Gln Val Met Ala Glu Leu Ser
        130                 135                 140

Pro Ala Ala Lys Thr Gly Lys Arg Lys Arg Ser Gln Met Leu Phe Arg
145                 150                 155                 160

Gly Arg Arg Ala Ser Gln
                165

(2) INFORMATION FOR SEQ ID NO:15:

(i) SEQUENCE CHARACTERISTICS:
        (A) LENGTH: 193 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: avian (vii) IMMEDIATE SOURCE:
        (B) CLONE: ChIFN-alpha (xi) SEQUENCE DESCRIPTION: SEQ ID NO:15:

Met Ala Val Pro Ala Ser Pro Gln His Pro Arg Gly Tyr Gly Ile Leu
1               5                   10                  15

Leu Leu Thr Leu Leu Leu Lys Ala Leu Ala Thr Thr Ala Ser Ala Cys
            20                  25                  30

Asn His Leu Arg Pro Gln Asp Ala Thr Phe Ser His Asp Ser Leu Gln
        35                  40                  45

Leu Leu Arg Asp Met Ala Pro Thr Leu Pro Gln Leu Cys Pro Gln His
    50                  55                  60

Asn Ala Ser Cys Ser Phe Asn Asp Thr Ile Leu Asp Thr Ser Asn Thr

```
65                  70                  75                  80
Arg Gln Ala Asp Lys Thr Thr His Asp Ile Leu Gln His Leu Phe Lys
                85                  90                  95
Ile Leu Ser Ser Pro Ser Thr Pro Ala His Trp Asn Asp Ser Gln Arg
                100                 105                 110
Gln Ser Leu Leu Asn Arg Ile His Arg Tyr Thr Gln His Leu Glu Gln
            115                 120                 125
Cys Leu Asp Ser Ser Asp Thr Arg Ser Arg Thr Arg Trp Pro Arg Asn
        130                 135                 140
Leu His Leu Thr Ile Lys Lys His Phe Ser Cys Leu His Thr Phe Leu
145                 150                 155                 160
Gln Asp Asn Asp Tyr Ser Ala Cys Ala Trp Glu His Val Arg Leu Gln
                165                 170                 175
Ala Arg Ala Trp Phe Leu His Ile His Asn Leu Thr Gly Asn Thr Arg
                180                 185                 190
Thr
```

(2) INFORMATION FOR SEQ ID NO:16:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:16:

ACTAGATCTC ATACTGCAAG TCTAAAT                      27

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:17:

ACTAAGCTTT TAGCAATTGC ATCTCCTCTG                 30